US010468119B2

(12) United States Patent
Fleishman et al.

(10) Patent No.: US 10,468,119 B2
(45) Date of Patent: Nov. 5, 2019

(54) STABLE PROTEINS AND METHODS FOR DESIGNING SAME

(71) Applicant: Yeda Research and Development Co. Ltd., Rehovot (IL)

(72) Inventors: Sarel Fleishman, Rehovot (IL); Adi Goldenzweig, Rehovot (IL); Dan S. Tawfik, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 256 days.

(21) Appl. No.: 15/259,311

(22) Filed: Sep. 8, 2016

(65) Prior Publication Data

US 2017/0032079 A1    Feb. 2, 2017

Related U.S. Application Data

(63) Continuation-in-part of application No. PCT/IL2016/050812, filed on Jul. 25, 2016.

(60) Provisional application No. 62/337,992, filed on May 18, 2016, provisional application No. 62/197,598, filed on Jul. 28, 2015.

(51) Int. Cl.
| | |
|---|---|
| G16B 15/00 | (2019.01) |
| C12N 9/18 | (2006.01) |
| C12N 9/16 | (2006.01) |
| C12N 9/10 | (2006.01) |
| G16B 30/00 | (2019.01) |
| G16B 35/00 | (2019.01) |
| G16C 20/10 | (2019.01) |
| G16C 20/60 | (2019.01) |
| G16B 15/20 | (2019.01) |

(52) U.S. Cl.
CPC ........... *G16B 15/00* (2019.02); *C12N 9/1007* (2013.01); *C12N 9/16* (2013.01); *C12N 9/18* (2013.01); *C12Y 201/01037* (2013.01); *C12Y 301/01007* (2013.01); *C12Y 301/08001* (2013.01); *G16B 15/20* (2019.02); *G16B 30/00* (2019.02); *G16B 35/00* (2019.02); *G16C 20/10* (2019.02); *G16C 20/60* (2019.02)

(58) Field of Classification Search
None
See application file for complete search history.

(56) References Cited

U.S. PATENT DOCUMENTS

| | | |
|---|---|---|
| 2002/0048772 A1 | 4/2002 | Dahiyat et al. |
| 2002/0110868 A1 | 8/2002 | Dahiyat et al. |
| 2003/0144472 A1 | 7/2003 | Emberly et al. |
| 2005/0064507 A1 | 3/2005 | Shaw |
| 2005/0181358 A1 | 8/2005 | Scholz et al. |
| 2009/0137409 A1 | 5/2009 | Tomso |
| 2010/0076173 A1 | 3/2010 | Stephanopoulos et al. |
| 2012/0014938 A1 | 1/2012 | Yang |
| 2012/0265513 A1 | 10/2012 | Fang et al. |
| 2015/0110836 A1 | 4/2015 | Glanville |

FOREIGN PATENT DOCUMENTS

| | | |
|---|---|---|
| WO | WO 2004/024917 | 3/2004 |
| WO | WO 2017/017673 | 2/2017 |

OTHER PUBLICATIONS

Chen, K. & Arnold, F.H., "Tuning the activity of an enzyme for unusual environments: sequential random mutagenesis of subtilisin E for catalysis in dimethylformamide", PNAS, 1993, 90(12):5618-5622. doi.org/10.1073/pnas.90.12.5618.*
Invitation to Pay Additional Fees dated Jan. 23, 2017 From the International Searching Authority Re. Application No. PCT/IL2016/50812. (2 pages).
International Search Report and the Written Opinion dated Mar. 31, 2017 From the International Searching Authority Re. Application No. PCT/IL2016/50812. (19 Pages).
International Preliminary Report on Patentability dated Feb. 8, 2018 From the International Bureau of WIPO Re. Application No. PCT/IL2016/050812. (10 Pages).
Alcolombri et al. "Directed Evolution of Sulfotransferases and Paraoxonases by Ancestral Libraries", Journal of Molecular Biology, 411(4): 837-853, Available Online Jun. 24, 2011.
Benedix et al. "Predicting Free Energy Changes Using Structural Ensembles", Nature Methods, 6(1): 3-4, Jan. 2009.
Benning et al. "High Resolution X-Ray Structures of Different Metal-Substituted Forms of Phosphotriesterase From Pseudomonas Diminuta", Biochemistry, 40: 2712-2722, Published on Web Jun. 2, 2001.
Binz et al. "Designing Repeat Proteins: Well-Expressed, Soluble and Stable Proteins From Combinatorial Libraries of Consensus Ankyrin Repeat Proteins", 332(2): 489-503, Sep. 12, 2003.
Borgo et al. "Automated Selection of Stabilizing Mutations in Designed and Natural Proteins", Proc. Natl. Acad. Sci. USA, PNAS, 109(5): 1494-1499, Jan. 31, 2012.
Capriotti et al. "I-Mutant2.0: Predicting Stability Changes Upon Mutation From the Protein Sequence or Structure", Nucleic Acids Research, 33(Web Server Issue): W306-W310, 2005.
Cherny et al. "Engineering V-Type Nerve Detoxifying Enzymes Using Computationally Focused Libraries", ACS Chemical Biology, 8(11): 2394-2403, Sep. 16, 2013.
Cheung et al. "Structures of Human Acetylcholinesterase in Complex With Pharmacologically Important Ligands", Journal of Medicinal Chemistry, 55(22): 10282-10286, Oct. 4, 2012.
Connolly "Solvent-Accessible Surfaces of Proteins and Nucleic Acids", Science 221(4612): 709-713, Aug. 19, 1983.
Dvir et al. "Acetylcholinesterase: From 3D Structure to Function", Chemico-Biological Interactions, 187(1-3): 10-22, Available Online Feb. 4, 2010.

(Continued)

Primary Examiner — John S Brusca

(57) ABSTRACT

A method for designing and selecting a protein having a stabilized structure compared to a corresponding wild type protein, and proteins having at least six amino acid substitutions with respect to a corresponding wild type protein, designed for improved thermal stability, improved specific activity and/or improved expression levels, are provided herein.

24 Claims, 6 Drawing Sheets
Specification includes a Sequence Listing.

(56) References Cited

OTHER PUBLICATIONS

Fischer et al. Expression and Reconstitution of Biologically Active Human Acetylcholinesterase From *Escherichia coli*, Cellular and Molecular Neurobiology, 13(1): 25-38, Feb. 1993.
Hoffmann et al. "Single-Molecule Assays for Investigating Protein Misfolding and Aggregation", Physical Chemistry Chemical Physics, 15(21): 7934-7948, Published Online Apr. 23, 2013.
Iwabata et al. "Thermostability of Ancestral Mutants of Caldococcus Noboribetus Isocitrate Dehydrogenase", FEMS Microbiology Letters, 243(2): 393-398, Published Online Jan. 6, 2005.
Jia et al. "Structure of Dnmt3a Bound to Dnmt3L Suggests a Model for De Novo DNA Methylation", Nature, 449(7159): 248-251, Sep. 13, 2007.
Jurkowska et al. "Structure and Function of Mammalian DNA Methyltransferases", ChemBioChem, 12(2): 206-222, Published Online Nov. 29, 2010.
Kellogg et al. "Role of Conformational Sampling in Computing Mutation-Induced Changes in Protein Structure and Stability", Proteins, 79(3): 830-838, Mar. 2011.
Knappik et al. "Fully Synthetic Human Combinatorial Antibody Libraries (HuCAL) Based on Modular Consensus Frameworks and CDRs Randomized With Trinucleotides", Journal of Molecular Biology, 296(1): 57-86, Feb. 11, 2000.
Korkegian et al. "Computational Thermostabilization of an Enzyme", Science, 308: 857-860, May 6, 2005.
Lehmann et al. "Engineering Proteins for Thermostability: The Use of Sequence Alignments Versus Rational Design and Directed Evolution", Current Opinion in Biotechnology, 12(4): 371-375, Aug. 2001.
Lehmann et al. "The Consensus Concept for Thermostability Engineering of Proteins", Biochimica et Biophysica Acta, 1543(2): 408-415, Dec. 29, 2000.
Pokala et al. "Energy Functions for Protein Design: Adjustment With Protein-Protein Complex Affinities, Models for the Unfolded State, and Negative Design of Solubility and Specificity", Journal of Molecular Biology, 347(1): 203-227, Available Online Jan. 20, 2005.
Potapov et al. "Assessing Computational Methods for Predicting Protein Stability Upon Mutation: Good on Average But Not in the Details", Protein Engineering Design & Selection, 22(9): 553-560, Published Online Jun. 26, 2009.
Rees et al. "Some Thermodynamic Implications for the Thermostability of Proteins", Protein Science, 10(6): 1187-1194, Jun. 2001.
Roodveldt et al. "Directed Evolution of Phosphotriesterase From Pseudomonas Diminuta for Heterologous Expression in *Escherichia coli* Results in Stabilization of the Metal-Free State", Protein Engineering Design & Selection, 18(1): 51-58, Published Online Mar. 15, 2005.
Rost "Twilight Zone of Protein Sequence Alignments", Protein Engineering, 12(2): 85-94, 1999.
Schaeffer et al. "Improving the Accuracy of PSI-BLAST Protein Database Searches With Composition-Based Statistics and Other Refinements", Nucleic Acids Research, 29(14): 2994-3005, Jul. 15, 2001.
Schymkowitz et al. "The FoldX Web Server: An Online Force Field", Nucleic Acids Research, 33(Web Server Issue): W382-W388, 2005.
Steipe et al. "Sequence Statistics Reliably Predict Stabilizing Mutations in a Protein Domain", Journal of Molecular Biology, 240(3): 188-192, Jul. 15, 1994.
Sullivan et al. "Stabilizing Proteins From Sequence Statistics: The Interplay of Conservation and Correlation in Triosephosphate Isomerase Stability", Journal of Molecular Biology, 420(4-5): 384-399, Available Online May 1, 2012.
Sullivan et al. "Triosephosphate Isomerase by Consensus Design: Dramatic Differences in Physical Properties and Activity of Related Variants", Journal of Molecular Biology, 413(1): 195-208, Available Online Aug. 4, 2011.
Trudeau et al. "Engineered Thermostable Fungal Cellulases Exhibit Efficiant Synergistic Cellulose Hydrolysis at Elevated Temperatures", Biotechnology and Bioengineering, 111(12): 2390-2397, Published Online Aug. 5, 2014.
Watanabe et al. "Designing Thermostable Proteins: Ancestral Mutants of 3-Isopropylmalate Dehydrogenase Designed by Using a Phylogenetic Tree", Journal of Molecular Biology, 355(4): 664-674, Available Online Nov. 8, 2005.
Supplementary European Search Report and the European Search Opinion dated Mar. 6, 2019 From the European Patent Office Re. Application No. 16829955.0. (11 Pages).

* cited by examiner

STABLE PROTEINS AND METHODS FOR DESIGNING SAME

RELATED APPLICATIONS

This application is a Continuation-in-Part (CIP) of PCT Patent Application No. PCT/IL2016/050812 filed on Jul. 25, 2016, which claims the benefit of priority under 35 USC 119(e) of U.S. Provisional Application No. 62/197,598 filed Jul. 28, 2015 and 62/337,992 filed on May 18, 2016, the contents of which are incorporated herein by reference in their entirety.

SEQUENCE LISTING STATEMENT

The ASCII file, entitled 67561SequenceListing.txt, created on Sep. 8, 2016, comprising 43,504 bytes, and submitted concurrently with the filing of this application, is incorporated herein by reference.

FIELD AND BACKGROUND OF THE INVENTION

The present invention, in some embodiments thereof, relates to computational chemistry and computational protein design and, more particularly, but not exclusively, to proteins designed for stability and a method of computationally designing and selecting an amino-acid sequence having desired properties.

Evolutionary processes have been shown to produce myriad of protein families, the members of which differ by more than 40% in terms of amino acid sequence identity, yet share common folds and sometimes similar functional activity. While fascinating in their simplicity and diversity, such evolutionary process are not regarded as efficient or optimal in terms of the number and type of mutations required to alter a protein sequence in order to alter its function. Yet, when attempted in the laboratory, human rationale and best computational and experimental tools and methodologies generally fail to improve upon the function of a protein even with a relatively small number of site-directed mutations, not to mention more than 10 mutations in a single sequence; such attempts rarely result in a protein that can be expressed or fold correctly.

Most proteins need to independently fold into their native conformation in order to perform their molecular function, and natural selection has acted to stabilize such proteins up to the necessary level required in their respective environments. However, in order to be useful under the stringencies of research, biotechnology, and pharmacology, proteins are required to be produced and function in non-natural conditions that include non-native and heterologous expression systems, elevated temperatures, non-physiological pH, and the presence of proteases, all of which can result in nullified production and activity or reduced protein half-lives.

While proteins hold great potential for extensive use in research, industry and pharmaceutics, their use is often hampered by instability, low denaturation temperature (Tm), low expression levels, low solubility, misfolding, aggregation, lipid encapsulation and short half-life. Computational and experimental techniques for protein stabilization have been in use for decades but predictability is low; typically they misclassify single-point deleterious mutations as stabilizing with a probability of about 20%. In addition, stabilizing mutation may still reduce or even abrogate function as stability and activity trade-off in some cases.

Due to the importance of protein stability, there has been a great number of research endeavors attempting to contribute in this field in the past decades. State of the art strategies involved sequence statistics-based strategies, such as back to consensus/ancestral and other computational algorithms [Steipe, B. et al., *J Mol Biol.*, 1994, 15; 240(3):188-92; Lehmann M. et al., *Biochim Biophys Acta*, 2000, 29; 1543 (2):408-415; Lehmann M. et al., *Curr Opin Biotechnol*, 2001, 12(4):371-5; Knappik, A. et al., *J Mol Biol*, 2000, 296(1):57-86; Binz, H. K. et al., *J Mol Biol*, 2003, 332(2): 489-503; Sullivan, B. J. et al., *J Mol Biol*, 2011, 413(1): 195-208; Sullivan, B. J. et al., *J Mol Biol*, 2012, 420(4-5): 384-99; Iwabata, H. et al., *FEMS Microbiol Lett*, 2005, 243(2):393-8; and Watanabe, K. et al., *J Mol Biol*, 2006, 355(4):664-74]. However, no existing method has been able to predict large combinatorial mutants that do not contain deleterious mutations, which disrupt the protein structure rather than improve any one of its functions [Rees, D. O et al., *Protein Sci*, 2001, 10(6):1187-1194].

Computational algorithms typically use an energy function to predict the change in $\Delta\Delta G$ upon introducing mutation(s). Most currently available computational algorithms aim to predict only single point mutations, and provide a list of mutations that are not necessarily compatible with one another [Schymkowitz, J. et al., *Nucleic Acids Res*, 2005, 33:W382-8; Capriotti, E. et al., *Nucleic Acids Res*, 2005, 33:W306-10; Benedix, A. et al., *Nat Methods*, 2009, 6(1):3-4; and Pokala, N. et al., *J Mol Biol*, 2005, 347(1):203-27].

In general, presently known computational structure stabilization methodologies suffer from poor prediction accuracy of less than 60% [Potapov, V. et al., *Protein Eng Des Sel*, 2009, 22(9):553-60; and Kellogg, D. B. E. et al., *Proteins*, 2011, 79(3):830-8], requiring high-throughput experimental procedures to achieve significantly more stable protein variants. In addition, for large and highly challenging proteins these methods are ineffective.

Rosetta$_{VIP}$ (void identification and packing) has been developed to improve the core packing of poorly packed proteins [Borgo, B. et al., *Proc Natl Acad Sci USA*, 2012, 109(5):1494-9]. The protocol recognizes voids within the protein core and then identifies small sets of mutations that reduce void volumes. This methodology successfully stabilized methionine aminopeptidase from *E. coli*. Another approach suggested a method for combinatorial design that is based on iterations between sequence redesign and backbone minimization, implemented in the Rosetta suite [Korkegian, A. et al., *Science*, 2005, 308(5723):857-60]. This methodology successfully stabilized yeast cysteine deaminase. It is noted that both the mentioned methodologies have been used for relatively small proteins that are generally stable having a wild-type Tm of above 50° C. In addition, both these studies examined each of the individual results and hand-picked selected sub-sets of mutations for in-vitro experiments. In both methods less than 10 mutations were introduced at once.

Additional background art include U.S. Pat. Nos. 4,908, 773 and 7,037,894 and U.S. Patent Application Nos. 20120171693 and 20130281314, which are incorporated herein by reference.

SUMMARY OF THE INVENTION

The invention, according to some embodiments thereof, is directed at designed proteins, having a non-naturally occurring, man-made amino acid sequence, at least to some extent and at least in one polypeptide chain thereof, that are more stable and exhibit several modified characteristics compared to their wild type counterpart. These characteristics are various manifestations of an improved structural stability, such as an increased thermal denaturation temperature, an increased solubility, a lower degree of misfolding and a smaller aggregated protein fraction during recombinant expression, an increased half-life, an increased specific activity, and an increased recombinant expression level, as compared to a corresponding wild type (original) protein.

The invention, according to some embodiments thereof, is also directed at a computational method for providing the non-naturally occurring amino acid sequence of the aforementioned designed proteins. The method is based on structural and ancestral data, and can provide modified amino acid sequences of relatively large proteins (more than 100 amino acids) by introducing therein at least six amino acid substitutions (mutations), relative to the corresponding wild type protein. According to some embodiments, the method is capable of finding stabilizing mutations within the core of the protein (at least 6 Å away from its surface) and further capable of introducing two or more mutations that can interact with each other (functional groups in their side chain can form a bond).

According to an aspect of some embodiments of the present invention there is provided a non-naturally occurring designed protein which includes at least one modified polypeptide chain having at least six amino acid substitutions relative to an original polypeptide chain, wherein the substitutions are modifying the designed protein relative to a corresponding wild type protein, as determined by at least one of:

a thermal denaturation temperature of the designed protein being equal or higher than a thermal denaturation temperature of the wild type protein;

a solubility of the designed protein being equal or higher than a solubility of the wild type protein;

a degree of misfolding of the designed protein being equal or lower than a degree of misfolding of the wild type protein;

a half-life of the designed protein being equal or longer than a half-life of the wild type protein;

a specific activity of the designed protein being equal or higher than a specific activity of the wild type protein; and a recombinant expression level of the designed protein being equal or higher than a recombinant expression level of the wild type protein.

According to some embodiments of the invention, the original polypeptide chain includes at least 100 amino acids.

According to some embodiments of the invention, a shortest distance of Cα of at least one of the amino acid substitutions is at least 6 Å from a water-accessible surface of the designed protein.

According to some embodiments, the position-specific stability scoring of each of the amino acid substitutions is equal or smaller than zero.

According to some embodiments, the position-specific scoring matrix (PSSM) value of each of the amino acid substitutions is at least 0.

According to some embodiments of the invention, at least two of the amino acid substitutions interact with one another such that the interaction stabilizes the modified protein, as determined by a lower free energy term of the modified protein compared to the original protein.

According to an aspect of some embodiments of the present invention there is provided a method of computationally designing a modified polypeptide chain starting from an original polypeptide chain, the method which includes:

Step I—determining unsubstitutable positions and substitutable positions in an amino acid sequence of the original polypeptide chain;

Step II—determining at least one position-specific amino acid alternative for each of the substitutable positions, and determining a position-specific stability scoring for each of the amino acid alternative;

Step III—combinatorially generating a plurality of designed sequences, each of the designed sequences corresponds to a modified polypeptide chain and includes at least one amino acid substitution being one of the at least one position-specific amino acid alternative, and threading each of the designed sequences on a template structure of the original polypeptide chain, to thereby generate a plurality of designed structures;

Step IV—sorting the plurality of designed structures according to a minimized energy scoring, the minimized energy scoring is determined by subjecting each of the designed structures to an energy minimization; and Step V—selecting at least one of the plurality of designed structures, corresponding to the modified polypeptide chain, based on the minimized energy scoring;

to thereby obtain the modified polypeptide chain.

According to some embodiments of the invention, the modified polypeptide chain includes at least six amino acid substitutions relative to the original polypeptide chain.

According to some embodiments of the invention, the original polypeptide chain includes at least 100 amino acids.

According to some embodiments of the invention, the selected modified polypeptide chain corresponds to designed structure having a minimal minimized energy scoring value.

According to some embodiments of the invention, the energy minimization (in Step IV) is a global energy minimization.

According to some embodiments of the invention, the designed sequences are combinatorially generated under an acceptance threshold based on the stability scoring.

According to some embodiments of the invention, determining the unsubstitutable positions and the substitutable positions is based on a sequence alignment of a plurality of amino acid sequences homologous to the original polypeptide chain.

According to some embodiments of the invention, for loop regions, the sequence alignment includes amino acid sequences having sequence length equal to a corresponding loop in the original polypeptide chain.

According to some embodiments of the invention, at least one of the unsubstitutable positions is determined based on the sequence alignment.

According to some embodiments of the invention, the sequence alignment is based on a non-redundant database of sequences.

According to some embodiments of the invention, the plurality of amino acid sequences includes sequences having less than 30% sequence identity with respect to said original polypeptide chain.

According to some embodiments of the invention, the plurality of amino acid sequences is clustered using a threshold of 90-100.%

According to some embodiments of the invention, the amino acid sequences having a coverage of less than 40% and a sequence identity of less than 15% are excluded from said plurality of amino acid sequences.

According to some embodiments of the invention, the amino acid sequences having more than 5% gaps (INDELs) are excluded from said plurality of amino acid sequences.

According to some embodiments of the invention, at least one of the unsubstitutable positions is selected from the group consisting of a highly conserved position, an active-site position, a metal binding position, a ligand binding position, a substrates binding position, a DNA/RNA binding position, a structure stabilizing position and an antigenic determinant position.

According to some embodiments of the invention, determining the position-specific amino acid alternative is dictated by rules.

According to some embodiments of the invention, the rules comprise a position-specific scoring matrix.

According to some embodiments of the invention, the position-specific stability scoring is determined based on an energy minimization.

According to some embodiments of the invention, the position-specific stability scoring is determined based on a local energy minimization.

According to some embodiments of the invention, the local energy minimization is effected for all amino acid residues within a 5 Å shell, namely for amino acid residues of the modified polypeptide chain having at least one atom being less than about 5 Å from at least one atom of the position-specific amino acid alternative.

According to some embodiments of the invention, the template structure is subjected to global energy minimization prior to the threading.

According to some embodiments of the invention, the template structure is an experimentally determined structure.

According to some embodiments of the invention, the template structure is a computationally determined based on an experimentally determined structure of a naturally occurring homolog of the original polypeptide chain.

According to some embodiments of the invention, the energy minimization includes at least one operation selected from the group consisting of bond length optimization, bond angle optimization, backbone dihedral angles optimization, amino acid side-chain packing optimization and rigid-body optimization of the modified polypeptide chain.

According to an aspect of some embodiments of the present invention there is provided a modified polypeptide chain, obtained by the method of computationally designing a modified polypeptide chain starting from an original polypeptide chain presented herein.

According to some embodiments of the invention, the polypeptide chain obtained by the method presented herein comprises at least six amino acid substitutions relative to the original polypeptide chain.

According to some embodiments of the invention, the original polypeptide chain obtained by the method presented herein comprises at least 100 amino acids.

According to an aspect of some embodiments of the present invention there is provided a method of producing the designed protein presented herein, which is effected by:

obtaining an amino acid sequence of the modified polypeptide chain using the method of computationally designing a modified polypeptide chain starting from an original polypeptide chain presented herein; and expressing the designed protein in an expression system; thereby producing the designed protein.

According to some embodiments of the invention, the expression system is a recombinant expression system.

According to some embodiments of the invention, the expression system comprises live cells selected form the group consisting of prokaryotic cells, eukaryotic cells, bacterial cells, fungi cells, yeast cells, algae cells, plant cells, parasite cells, insect cells, animal cells, ovarian cells, fish cells, bird cells and mammalian cells.

According to some embodiments of the invention, the original polypeptide chain includes at least 100 amino acids.

According to some embodiments of the invention, a shortest distance of Cα of at least one of the amino acid substitutions is at least 6 Å from a water-accessible surface of the designed protein.

According to some embodiments of the invention, at least two of the amino acid substitutions interact with one another such that the interaction stabilizes the modified protein, as determined by a lower free energy term of the modified protein compared to the original protein.

According to an aspect of some embodiments of the present invention there is provided a protein having a sequence selected from the group consisting of any combination of at least 6 amino acid substitutions of a sequence space afforded for AChE from human as an original protein and listed in Table 2 presented below, or afforded for PTE from *Pseudomonas diminuta* as an original protein and listed in Table 4 presented below.

According to some embodiments of the invention, the protein is a hybrid protein wherein the combination of amino acid substitutions taken from Table 2 or able 4, is implemented on a protein other than the corresponding original protein, AChE from human or PTE from *Pseudomonas diminuta*, respectively.

According to some embodiments of the invention, the protein is having a sequence selected from the group consisting of RhAChE_m0p9 (SEQ ID No. 2), RhAChE_m0p45 (SEQ ID No. 3), RhAChE_m0p7 (SEQ ID No. 4), RhAChE_m1p2 (SEQ ID No. 5), RhAChE_m2p0 (SEQ ID No. 6), dPTE_m0p45 (SEQ ID No. 8), dPTE_m1p0 (SEQ ID No. 9), and dPTE_m2p0 (SEQ ID No. 10).

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a scaffold" or "at least one scaffold" may include a plurality of scaffolds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-D are simplified illustrations of the output of the single position scanning step and the input of the iterative combinatorial design step of the method provided herein, according to some embodiments of the present invention, wherein FIG. 2A shows the various positions of the original polypeptide chain (SEQ ID No. 12; top row) comprising key residues (see definition hereinbelow; marked by diamonds), unsubstitutable positions (which do not have even a single non-WT amino acid alternative that has a PSSM score equal to or above 0; marked by circles), and substitutable positions (which have at least one non-WT amino acid alternative that has a PSSM score equal to or above 0; marked by squares), and, wherein some of the substitutable positions have stacked thereunder amino acid alternatives that have a position-specific stability scoring below the exemplary permissive acceptance threshold of −0.45 r.e.u, and wherein the variety of alternatives are marked by various shapes according to their position-specific stability scoring, starting at the most permissive threshold, and wherein FIGS. 2B-D show a smaller set of permuted amino acid alternatives since the number of alternatives with position-specific stability scoring below each stricter acceptance threshold value is reduced, according to some embodiments of the present invention;

DESCRIPTION OF SPECIFIC EMBODIMENTS OF THE INVENTION

Figure 1:
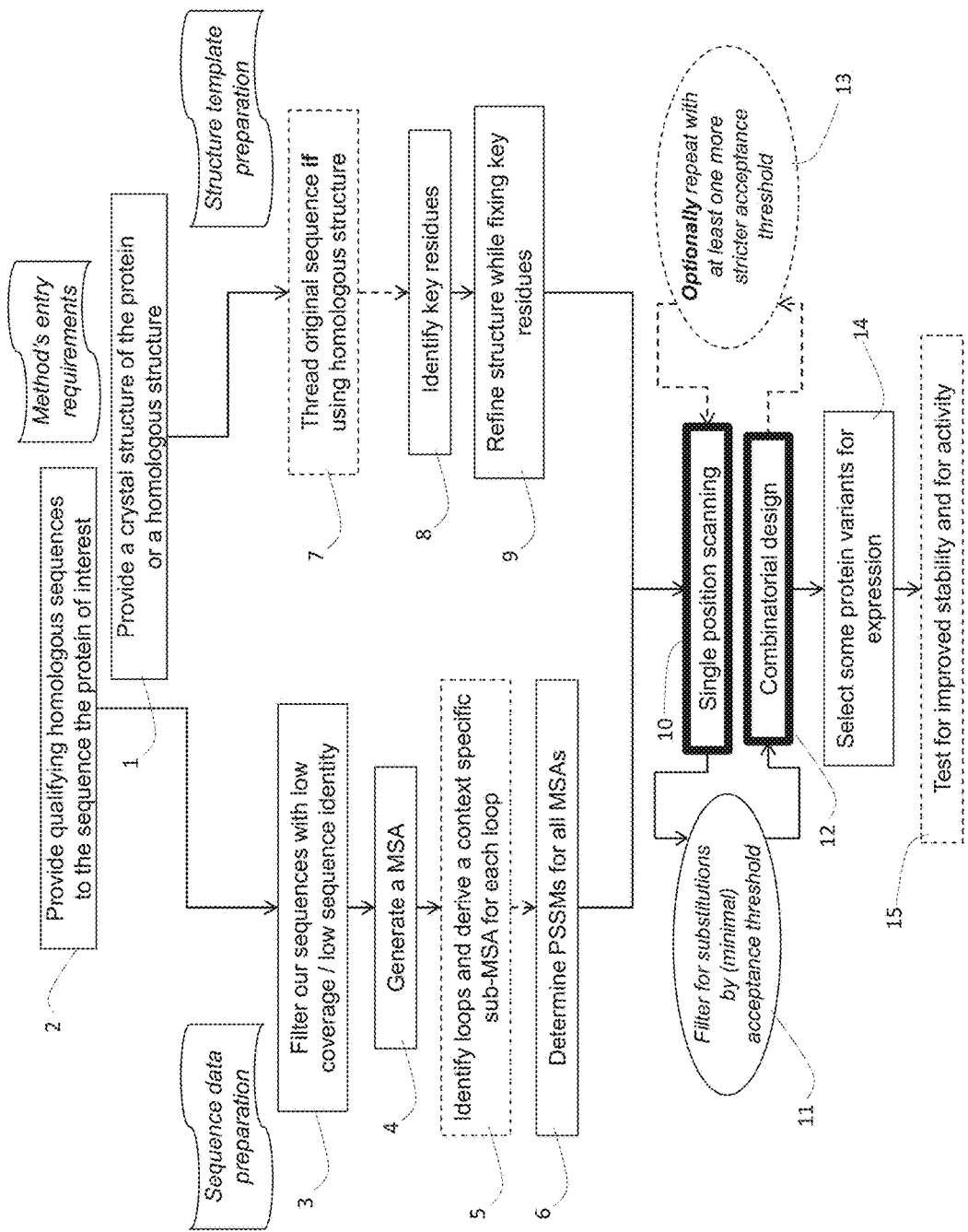
FIG. 1 is a schematic flowchart illustration of an exemplary algorithm for executing the method of computationally designing a modified polypeptide chain starting from an original polypeptide chain, according to some embodiments of the present invention.

The present invention, in some embodiments thereof, relates to computational chemistry and computational protein design and, more particularly, but not exclusively, to proteins designed for stability and a method of computationally designing and selecting an amino-acid sequence having desired properties.

The principles and operation of the embodiments of the present invention may be better understood with reference to the examples and accompanying descriptions.

Before explaining at least one embodiment of the invention in detail, it is to be understood that the invention is not necessarily limited in its application to the details set forth in the following description or exemplified by the Examples.

The invention is capable of other embodiments or of being practiced or carried out in various ways.

Most stabilizing mutations are said to contribute less than −0.5 kcal/mol, or about −0.25 kcal/mol to protein stability, in terms of ΔΔG. Therefore, achieving a significant effect on protein stability requires a combination of numerous mutations. The extent of thermal tolerance of any given protein is an inherent property of its amino acid sequence. As discussed hereinabove, previous studies have established a correlation between a change in protein free energy per residue (ΔΔG/residue) and a change in protein Tm [Rees, D. O et al., *Protein Sci*, 2001, 10(6):1187-1194; and Ku, T. et al., *Comput Biol Chem*, 2009, 33(6):445-50]. This correlation indicates that the number of mutations essential for a significant effect increases with the size of the protein. In light of this, a computational tool that provides a solution to the problem of determining reliable protein mutation for stabilization has a great potential to enable and facilitate the use of proteins in research, industry and therapeutics. However, simultaneous introduction of tens of mutations to a protein sequence without adversely affecting its function requires that none of the mutations is deleterious, namely mutations that have a dramatic destabilizing effect that leads to massive unfolding, misfolding, aggregation and/or precipitation or unproductive expression levels. If the probability of a mutation to be deleterious is around 20%, it means that the probability of a protein with 6 mutations to contain no deleterious mutation is about 26% ($0.8^6$), for 10 mutations to contain no deleterious mutations the probability is less than 11% ($0.8^{10}$), and for a protein with 40 mutations the probability of not having even a single deleterious mutation drops to 0.013%)($0.8^{40}$. The method presented herein, which combines evolutionary-conservation analysis with combinatorial protein sequence design, minimizes the number of predicted false-positive amino acid substitutions.

While conceiving the present invention, the present inventors have hypothesized that for large and structurally sensitive proteins, many point mutations are necessary to achieve measurable stabilization effects. The present inventors have developed a protein stabilization method that provides a fully automated combinatorial solution with numerous mutations per variant (e.g., more than 6 in a protein of more than 100 amino acids). While reducing the present invention to practice, it has been demonstrated that the method is effective and general, and leads to experimental validation using low throughput experiments that can be easily afforded in most facilities.

While further reducing the present invention to practice and comparing its solution to the problem of designing proteins for thermal stability with the solutions provided by other methods, it was observed that the presently provided method for designing a stabilized protein typically results in a modified polypeptide chain having more than 6 amino-acid substitutions with respect to the original (wild type) polypeptide chain, wherein the substitutions have diverse physicochemical properties relative to the wild-type, including, either alone or in various combinations, more polar surfaces, prolines on loops, edge beta-strands, or at helix amino termini, improved packing (for instance, Val substituted with Ile or Phe), and more hydrogen bonds within the structure, improved secondary structure propensity. None of the presently known methods provided variants exhibiting all of the above.

For test cases, the method has been used to provide stabilized variants of three proteins known for their heightened structural sensitivity—human acetylcholinestrase (hAChE), phosphotriesterase (PTE) from *pseudomonas diminuta*, and a mammalian DNA methyltransferase 3 (Dnmt3). Five de novo designed hAChE variants, each having from 17 to 67 point mutations were tested, and all were found to have significantly higher recombinant expression levels versus the wild type (WT) protein, which is a clear indication of improved stability. The most successful designed protein exhibited about 1800-fold higher bacterial expression levels compared to the WT protein. Three PTE designs, having 9, 19 and 28 amino acid substitutions compared to the wild-type PTE were tested and compared to a known improved variant of PTE, PTE-S5 (SEQ ID No. 7) [Roodveldt, C. et al., *Protein Engineering, Design & Selection*, 2005, 18(1), pp. 51-58]. Two of the variant designs exhibited about 10° C. higher tolerance to heat inactivation and increased $Zn^{+2}$ ion affinity, and had slightly higher recombinant expression levels compared to PTE-S5 (SEQ ID No. 7), which is 20-fold higher than wild type PTE. The demonstration of the method for the catalytic domain of human DNA methyl transferase from family 3 (Dnmt3a), was based on a poorly determined experimental structure, yet afforded a designed variant that exhibited about 7 fold higher activity compared to the WT Dnmt3a, as presented in the Example section that follows.

The method presented herein is effectively used to provide modified polypeptide chains starting with an original polypeptide chain, such as found in a corresponding wild type protein, wherein several amino acid residues in the original polypeptide chains have been substituted such that a protein expressed to have the modified polypeptide chains (a variant protein) exhibits improved structural stability compared to the wild type protein. The term "variant", as used herein, refers to a designed protein obtained by employing the method presented herein. Herein and throughout, a terms "amino acid sequence" and/or "polypeptide chain" is used also as a reference to the protein having that amino acid sequence and/or that polypeptide chain; hence the terms "original amino acid sequence" and/or "original polypeptide chain" are equivalent or relate to the terms "original protein" and "wild type protein", and the terms "modified amino acid sequence" and/or "modified polypeptide chain" are equivalent or relate to the terms "designed protein" and "variant".

In some embodiments, the original polypeptide chain, or the original protein, is naturally occurring (wild type; WT) or artificial (man-made non-naturally occurring).

In the context of some embodiments of the present invention, the term "designed" and any grammatical inflections thereof, refers to a non-naturally occurring sequence or protein.

In the context of some embodiments of the present invention, the term "sequence" is used interchangeably with the term "protein" when referring to a particular protein having the particular sequence.

According to an aspect of some embodiments of the present invention, there is provided a method of computationally designing a modified polypeptide chain starting from an original polypeptide chain.

FIG. 1 is a schematic flowchart illustration of an exemplary algorithm for executing the method of computationally designing a modified polypeptide chain starting from an original polypeptide chain, according to some embodiments of the present invention.

Method Requirements and Input Preparation:

The basic requirements for implementing the method for designing modified polypeptide chains for higher stability include:

availability of structural information pertaining to the original polypeptide chain, such as obtained from an experimentally determined crystal structure of the original polypeptide chain, or a crystal structure of a close homolog thereof, having at least 40-60% amino acid sequence identity, or computationally derived structural information based on an experimentally determined structure of a close homolog thereof (Box 1 in FIG. 1); and availability of sequence data derived from at least 20-30 qualifying homologous proteins, whereas the criteria for a qualifying homologous sequence are described below (Box 2 in FIG. 1).

Figure 6:
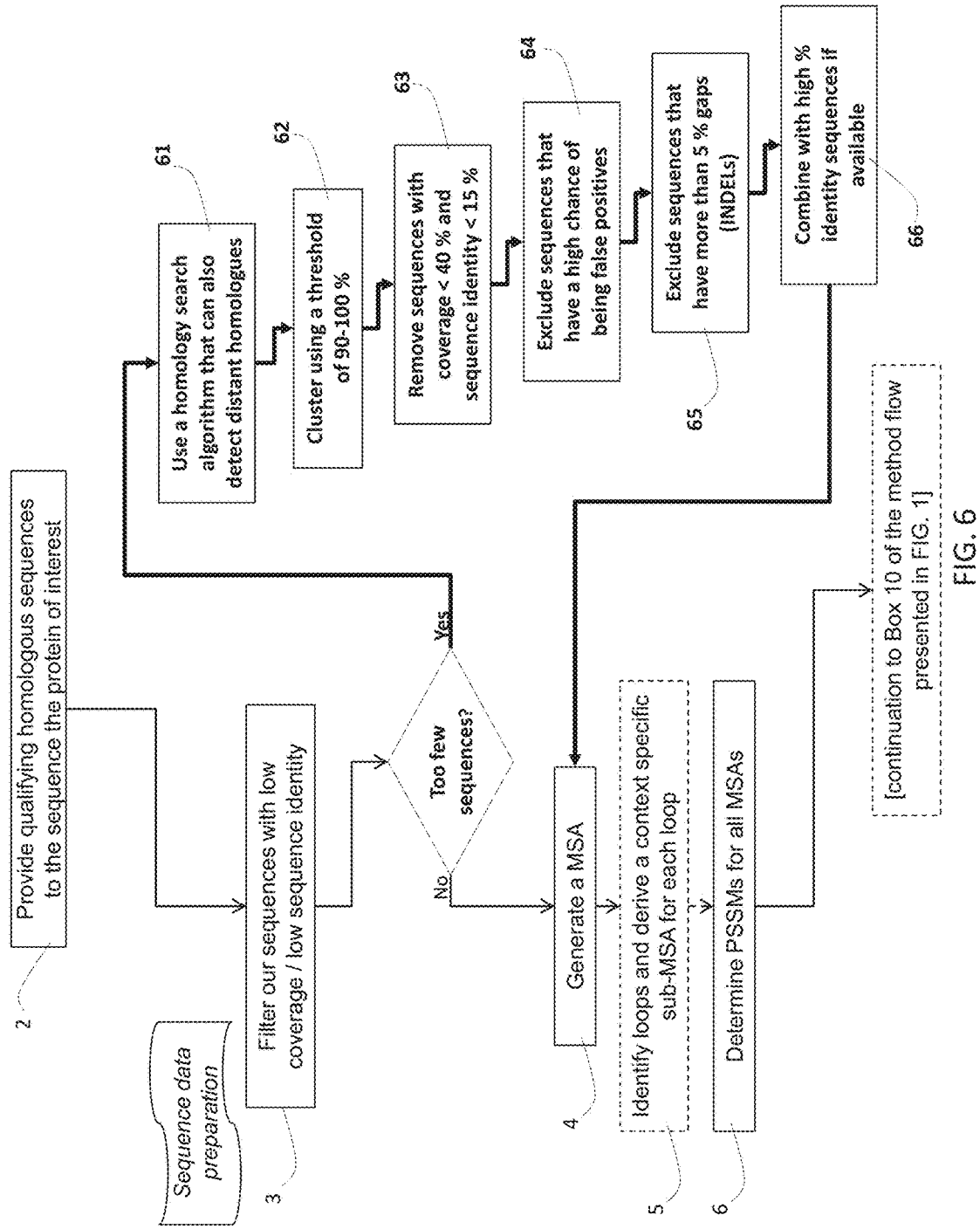
FIG. 6 is a schematic flowchart illustration of an exemplary sub-algorithm of the algorithm presented herein, for treating cases wherein there is a low availability of homologous proteins, and thus low availability of qualifying homologous sequences, according to some embodiments of the present invention.

In some cases of low availability of homologous proteins, the method utilizes a unique approach for selecting qualifying homologous sequences, as described below and presented in FIG. 6.

In the context of embodiments of the present invention, the term "% amino acid sequence identity" or in short "% identity" is used herein, as in the art, to describe the extent to which two amino acid sequences have the same residues at the same positions in an alignment. It is noted that the term "% identity" is also used in the context of nucleotide sequences.

Structural Data Preparation:

According to some embodiments of the invention, the structural information is a set of atomic coordinates of the original polypeptide chain. This set of atomic coordinates is referred to herein as the "template structure", which is used in the method as discussed below. In some embodiments, the template structure is a crystal structure of the original polypeptide chain, and in some embodiments the template structure is a computationally generated structure based on a crystal structure of a close homolog (more than 40-60% identity) of the original polypeptide chain, wherein the amino acid sequence of the original polypeptide chain has been threaded thereon and subjected to weighted fitting to afford energy minimization thereof, as these are discussed below.

In cases where the protein of interest is an oligomer (having several polypeptide chains), the chain of interest, or the original polypeptide chains to be modified, is defined in the template structure. In the case of hetero-oligomers, it is required to select the chain that will undergo the sequence design procedure. To design more than one chain, the method is used separately for each original polypeptide chain. For homo-oligomers it is advantageous to select the original polypeptide chain containing having more or better quality structural data. For example, in some homo-oligomers, binding ions may be discernible crystallographycally in some of the chains and less so in others. In addition, it is advantageous to define key residues related to function and activity, as discussed hereinbelow.

Structure Refinement:

According to some embodiments, prior to its use in the method presented herein, the template structure is subjected to a global energy minimization, afforded by weighted fitting thereof, as discussed below.

According to some embodiments of the present invention, the template structure is optionally refined by energy minimization prior to using its coordinates, while fixing the conformations of key residues, as defined hereinbelow (Box 9 in FIG. 1). Structure refinement is a routine procedure in computational chemistry, and typically involves weight fitting based on free energy minimization, subjected to rules, such as harmonic restraints.

The term "weight fitting", according to some embodiments of any of the embodiment of the present invention, refers to a one or more computational structure refinement procedures or operations, aimed at optimizing geometrical, spatial and/or energy criteria by minimizing polynomial functions based on predetermined weights, restraints and constrains (constants) pertaining to, for example, sequence homology scores, backbone dihedral angles and/or atomic positions (variables) of the refined structure. According to some embodiments, a weight fitting procedure includes one or more of a modulation of bond lengths and angles, backbone dihedral (Ramachandran) angles, amino acid side-chain packing (rotamers) and an iterative substitution of an amino acid, whereas the terms "modulation of bond lengths and angles", "modulation of backbone dihedral angles", "amino acid side-chain packing" and "change of amino acid sequence" are also used herein to refer to, inter alia, well known optimization procedures and operations which are widely used in the field of computational chemistry and biology. An exemplary energy minimization procedure, according to some embodiments of the present invention, is the cyclic-coordinate descent (CCD), which can be implemented with the default all-atom energy function in the Rosetta™ software suite for macromolecular modeling. For a review of general optimization approaches, see for example, "*Encyclopedia of Optimization*" by Christodoulos A. Floudas and Panos M. Pardalos, Springer Pub., 2008.

According to some embodiments of the present invention, a suitable computational platform for executing the method presented herein, is the Rosetta™ software suite platform, publically available from the "Rosetta@home" at the Baker laboratory, University of Washington, U.S.A. Briefly, Rosetta™ is a molecular modeling software package for understanding protein structures, protein design, protein docking, protein-DNA and protein-protein interactions. The Rosetta software contains multiple functional modules, including RosettaAbinitio, RosettaDesign, RosettaDock, RosettaAntibody, RosettaFragments, RosettaNMR, RosettaDNA, RosettaRNA, Ro settaLig and, RosettaSymmetry, and more.

Weight fitting, according to some embodiments, is effected under a set of restraints, constrains and weights, referred to as rules. For example, when refining the backbone atomic positions and dihedral angles of any given polypeptide segment having a first conformation, so as to drive towards a different second conformation while attempting to preserve the dihedral angles observed in the second conformation as much as possible, the computational procedure would use harmonic restraints that bias, e.g., the Cα positions, and harmonic restraints that bias the backbone-dihedral angles from departing freely from those observed in the second conformation, hence allowing the minimal conformational change to take place per each structural determinant while driving the overall backbone to change into the second conformation.

In some embodiments, a global energy minimization is advantageous due to differences between the energy function that was used to determine and refine the source of the template structure, and the energy function used by the method presented herein. By introducing minute changes in backbone conformation and in rotamer conformation through minimization, the global energy minimization relieves small mismatches and small steric clashes, thereby lowering the total free energy of some template structures by a significant amount.

In some embodiments, energy minimization may include iterations of rotamer sampling (repacking) followed by side chain and backbone minimization. An exemplary refinement protocol is provided in Korkegian, A. et al., *Science,* 2005.

As used herein, the terms "rotamer sampling" and "repacking" refer to a particular weight fitting procedure wherein favorable side chain dihedral angles are sampled, as defined in the Rosetta software package. Repacking typically introduces larger structural changes to the weight fitted structure, compared to standard dihedral angles minimization, as the latter samples small changes in the residue conformation while repacking may swing a side chain around a dihedral angle such that it occupies an altogether different space in the protein structure.

In some embodiments, wherein the template structure is of a homologous protein, the query sequence is first threaded on the protein's template structure using well established computational procedures (Box 7 in FIG. 1). For example, when using the Rosetta software package, according to some embodiments of the present invention, the first two iterations are done with a "soft" energy function wherein the atom radii are defined to be smaller. The use of smaller radius values reduces the strong repulsion forces resulting in a smoother energy landscape and allowing energy barriers to be crossed. The next iterations are done with the standard Rosetta energy function. A "coordinate constraint" term may be added to the standard energy function to "penalize" large deviations from the original Cα coordinates. The coordinate constraint term behaves harmonically (Hooke's law), having a weight ranging between about 0.05-0.4 r.e.u (Rosetta energy units), depending on the degree of identity between the query sequence and the sequence of the template structure. During refinement, key residues are only subjected to small range minimization but not to rotamer sampling.

A coordinate constraint weight may be imposed on the refinement procedure. As presented hereinbelow, a value of 0.4 has been found to be a useful coordinate constraint weight, as determined in a benchmark study (see, Example 1 hereinbelow).

Sequence Data Preparation:

Once an original polypeptide chain has been identified, and a corresponding template structure has been provided, the method requires assembling a database of qualifying homologous amino acid sequences related to the amino acid sequence of the original polypeptide chain. The amino acid sequence of the original polypeptide chain can be extracted, for example, from a FASTA file that is typically available for proteins in the protein data bank (PDB), or provided otherwise. The search for qualifying homologous sequences is done, according to some embodiments of the present invention, in the non-redundant (nr) protein database, using the sequence of the original polypeptide chain as a search query. Such nr-database typically contains manually and automatically annotated sequences and is therefore much larger than databases that contain only manually annotated sequences.

A non-limiting examples of protein sequence databases include INSDC EMBL-Bank/DDBJ/GenBank nucleotide sequence databases, Ensembl, FlyBase (for the insect family Drosophilidae), H-Invitational Database (H-Inv), International Protein Index (IPI), Protein Information Resource (PIR-PSD), Protein Data Bank (PDB), Protein Research Foundation (PRF), RefSeq, *Saccharomyces* Genome Database (SGD), The *Arabidopsis* Information Resource (TAR), TROME, UniProtKB/Swis s-Prot, UniProtKB/Swis s-Prot protein isoforms, UniProtKB/TrEMBL, Vertebrate and Genome Annotation Database (VEGA), WormBase, the European Patent Office (EPO), the Japan Patent Office (JPO) and the US Patent Office (USPTO).

A search in a nr-database yields variable results depending on the search query (amino-acid sequence of the original polypeptide chain). For proteins with lacking sequence data, results may include less than 10 hits. For proteins common to all life kingdoms the results may include thousands of hits. For most proteins hundreds to thousands of hits are expected upon search in a nr-database. In all databases, including a nr-database and despite its name, there may be redundancy to some extent, and hits may be found in groups of identical sequences. The redundancy problem is addressed during the sequence data editing, as described hereinbelow.

In some embodiments of the invention, the obtained sequence data is optionally filtered and edited as follows (Box 3 in FIG. 1):

(a) Redundant sequences are clustered into a single representative sequence. The clustering is carried out with a threshold of 0.97, meaning that all sequences that share at least 97% identity among themselves are clustered into a single representative sequence that is the average of all the sequences contributing to the cluster;

(b) Sequences for which the alignment length is less than 60% of the search query length are excluded; and (c) Sequences that exhibit less than about 28% to 34% identity cutoff with respect to the search query are excluded, following guidelines such as provided elsewhere [Rost, B., *Protein Eng*, 1999, 12(2):85-94].

The exact choice of the minimal identity parameter depends on the richness of the sequence data. Hence, according to some embodiments of the invention, if the number of sequence hits afforded under a strict threshold is about 50 or less, a less strict threshold may be used (lower % identity). The effect of threshold tuning of the identity parameter is demonstrated in the design of a phosphotriesterase from *pseudomonas diminuta*, where lowering the threshold from 30% to 28% identity increased the number of qualifying homologous sequences from 45 to 95 (see, Examples section hereinbelow).

In some embodiments of the invention, the cutoff for electing qualifying homologous sequences for a multiple sequence alignment is more than 20%, 25%, 30%, 35%, 40%, or more than 50% identity with respect to the original polypeptide chain.

It is noted that the method is not limited to any particular sequence database, search method, identity determination algorithm, and any set of criteria for qualifying homologous sequences. However, the quality of the results obtained by use of the method depends to some extent on the quality of the input sequence data.

Once an assembly of qualifying homologous sequences is obtained, a multiple sequence alignment (MSA) is generated (Box 4 in FIG. 1), typically by using a designated multiple sequence alignment algorithm, such as that implemented in MUSCLE [Edgar, R. C., *Nucleic Acids Res*, 2004, 32(5): 1792-1797]. Alternatively, a Basic Local Alignment Search Tool (BLAST) can be used to generate MSA files.

Cases of Low Availability of Homologous Proteins:

Generally, adding sequences exhibiting a % identity below 20% to a MSA having dozens of homologous sequences of higher % identity may contribute diversity to the alignment; however, adding such kind of low % identity sequences increases the risk of errors (false positives) significantly while not necessarily improving diversity by much, since most of this diversity will probably be covered by the high homology sequences that were already part of the MSA. On the other hand, when the protein of interest is poorly represented in the sequence database, using a low % identity homolog becomes an advantage rather than a risk.

In some cases the protein of interest is poorly represented in the currently available protein sequence databases in terms of the number of non-redundant homologous sequences. For example, in case that a sequence homology search finds only one homologous sequence having 60% sequence identity to the protein of interest, that means that the method is limited to zero amino acid substitutions in 60% of the sequence positions, and out of the remaining 40% it would have been difficult to identify a position with more than few amino acid alternatives.

In such cases, the present inventors have envisioned several scenarios where standard sequence homology search methods might result in low sequence diversity within the space of homologous sequences (e.g., less than 50%, less than 40%, less than 30%, less than 25% (the "twilight zone") or less than 20% sequence identity with respect to the amino acid sequence of the protein of interest). An example for such a scenario is where the fold of the protein of interest (the target protein, also referred to herein as the original polypeptide chain) is unique or phylogenetically restricted to particular genera or phyla, or the protein function has emerged in recent millennia and the protein of interest therefore has few homologues. It was envisioned by the present inventors that in such or other cases of low sequence diversity, the following steps could be taken to increase the sequence diversity used by presently provided method, while minimizing the risk of introducing unrelated sequences.

An exemplary sub-algorithm for treating such cases is described below. The general rational behind this sub-algorithm is to increase the number of homologous sequences in the MSA as much as possible while minimizing the risk of including non-related sequences; for example, accounting for the fact that the fold of the protein of interest is unique and/or phylogenetically distant from typical organisms interrogated by sequencing efforts.

Step 1 (Box 61 in FIG. 6): search for low-sequence identity homologous sequences (e.g., less than 50%, less than 40%, less than 30%, less than 25% or less than 20% sequence identity; preferably less than 30% identity) in any given sequence database by using an algorithm that specializes in detection of distant homologues (e.g., CSI-BLAST; see, PMIDs: 19234132, 18004781);

Step 2 (Box 62 in FIG. 6): cluster the results from Step 1 using a clustering threshold 90-100% (see, e.g., PMID: 11294794);

Step 3 (Box 63 in FIG. 6): remove sequences with coverage below 40% relative to that of the original polypeptide chain (protein of interest), and sequence identity of less than 15%;

Step 4 (Box 64 in FIG. 6): inspect the annotation and source organism of each sequence in the list resulting from Step 3, and exclude sequences that have a high chance of being false positives. Non-limiting examples are hits that have no molecular-function annotation (typically these are annotated as "hypothetical protein"), sequences from genera or phyla other than the protein of interest's genus or phylum, or proteins that are annotated with functions that are different from the function of the protein of interest;

Step 5 (Box 65 in FIG. 6): Exclude sequences that have more than 5%, more than 4%, more than 3%, more than 2%, more than 1%, or more than 0.5% gaps (insertions or deletions, known by the acronym INDELs), preferably less than 5% gaps in a pairwise alignment with the original polypeptide chain (see, e.g., PMID: 18048315);

Step 6 (Box 66 in FIG. 6): Combine sequences resulting from Step 5 with high sequence identity sequences (i.e., more than 30% sequence identity to the protein of interest) that were collected and processed using any sequence identity search protocol, and generate a multiple-sequence alignment (MSA). This MSA can then be used as input by the method presented herein (see, Box 4 in FIG. 1 and FIG. 6) even if it contains few (less than 3-10) sequences.

A more specific yet non-limiting example is described below:

Step I: Use the CSI-BLAST search algorithm instead of BLASTP to identify homologs. The use of an alternative sequence search algorithm to find distant homologues, such as using CSI-BLAST (context-specific iterative BLAST) with 3 iterations instead of BLASTP is advantageous in some cases since CSI-BLAST constructs a different substitution matrix to calculate alignment scores. The CSI-BLAST matrix is context specific (i.e., each position probabilities depend also on 12 neighboring amino acids), thus it finds 50% more homologous sequences than BLAST at the same error rate. The iterative use means that this process is repeated and at the end of each round the substitution matrix is updated according the sequence information from homologues collected up to that point.

Step II: Use minimal sequence identity thresholds of 19% and 15% for strict and permissive alignments respectively. Lowering the minimal sequence identity threshold to 15% (permissive alignment) and 19% (strict alignment) while using BLASTP may be meaningless since BLASTP is tuned to find sequences with higher sequence identity to the target. Secondly, these thresholds are chosen according to the results obtained from the CSI-BLAST search; hence these thresholds are set after the CSI-BLAST search and depend on outcome; specifically, the thresholds may need to be adjusted to obtain more true positive or fewer false positive hits, where true positive are hits with a functional annotation and phylogenetic origin that correspond to the requirements of Step III, below.

Step III: Exclude sequences from genera or phyla other than the one corresponding to the protein of interest if it is expected that protein target's fold or function are unique to the genus of phylum of the target protein. If this expectation holds, proteins from genera and phyla outside those of the target protein are likely to be false-positive hits; that is, proteins that adopt different folds or function.

Step IV: Use an INDEL fraction of up to 1% for sequences sharing below 19% sequence identity, in pairwise alignment with the query. In the treatment of gaps/INDELs the CSI-BLAST pairwise alignment INDELS fraction may be required to be up to 1% for sequence with minimal % identity below 19%. The rationale is that for low-homology sequences sharing such a small sequence identity to the query, the risk of inserting false positives in the MSA is too high, but a small INDEL fraction indicates that these are likely to be true hits.

Step V: Use sequence coverage threshold for hits relative to the target protein in the alignment to 50%. It is likely that all the sequences that passed the criteria set forth in Steps II, III and IV will exhibit a coverage of more than 50%; however, if the coverage threshold is set to 60%, as typically practiced in the art, most of the sequences would be filtered out.

Step VI: Generate MSA for the remaining sequences as typically practiced in the art.

Variable Loop Regions:

BLAST algorithms may provide results that include sequences with different lengths. The differences typically stem from different lengths in loop regions, and loops with different lengths may reflect different biochemical context. As a result, MSA columns representing loop positions may contain aligned residues from loops with different length, thus possibly degrading the data with information from different biochemical context, possibly irrelevant to the biochemical context of the protein of interest. A BLAST hit may therefore contain relevant information at some positions while containing non-relevant information in other positions. To minimize the level of irrelevant sequence information for each loop, the secondary structure of the original protein is identified and a context specific sub-MSA file is created for each loop region, and the sub-MSA contains only loop sequences with the same length.

Secondary structure identification is done through identification of hydrogen bond patterns in the structure and this is termed "dictionary of protein secondary structure" (DSSP). There are several software packages available that offer such analysis, such as, for example, a Rosetta™ module for loop identification.

The output of the secondary structure identification procedure is typically a string (i.e., an output string) that has the same length as the template structure, wherein each character represents a residue in a secondary structure element that may be either H, E or L, denoting an amino acid forming a part of either an α-helix, a β-sheet or a loop.

According to some embodiments of the invention, the amino acid sequence of the loop regions in the structure of the original protein is processed as follows:

(a) Loops in the template structure are identified by automatic or manual inspection of a structure model, and/or by any secondary-structure analyzing algorithms.

(b) The positions representing each loop on the output string are determined including loop stems (two additional amino acids at each end of the loop). To account for the stems, two positions are added to each of the loop's ends, unless the loop is at one of the main-chain termini. According to some embodiments of the invention, it is advantageous to include the stems in the loop definition since stems anchoring different loops may potentially exhibit different conformations and form different contacts among themselves or with the loop residues, and it is advantageous that the sequence data used as input in the method presented would represent that.

For example, if the secondary structure output string is:
LLLHHHHHHHLLLLLHHHHHLLLEEEE
then the loop regions are defined at positions 1-5, 9-17 and 19-25 (bold characters).

(c) The positions that represent each loop are identified in the query sequence in the MSA. The loop positions in the MSA may be different than the loop positions in the original string from the previous step since in the MSA the query is aligned to other sequences and may therefore contain both amino acid characters and hyphens, representing gaps.

(d) After the loop positions were located on the query sequence in the MSA, a character pattern is defined for each loop. For example, a pattern may comprise "X" character to represent an amino acid and "-" (hyphen) to represent a gap.

(e) Lastly, a context specific sub-MSA file is generated for each loop excluding all sequences that do not share the same character pattern for that loop, namely context specific sub-MSA contains sequences wherein the loop has the same length, gaps included.

For example, positions 4-10 in a hypothetical original protein are recognized as a loop with the hypothetical sequence "APTESVV" including stems. The loop is identified on the query protein in the MSA file and the pattern is found to be "A--PTESVV". The context specific sub-MSA file that will be generated for this loop with all the sequences in the MSA file will contain the pattern "X--XXXXX".

Thus, according to some embodiments of the present invention, for loop regions, the sequence alignment comprises amino acid sequences having sequence length equal to a corresponding loop in the original polypeptide chain. Accordingly, sequence alignments, which are relevant in the context of loop regions, are referred to herein as "context specific sub-MSA" (Box 5 in FIG. 1).

Rules for Substitutions:

In some embodiments of the present invention, a set of restraints, constrains and weights are used as rules that govern some of the computational procedures. In the context of some embodiments of the present invention, these rules are applied in the method presented herein to determine which of the positions in the original polypeptide chain will be allowed to permute (be substituted), and to which amino acid alternative. These rules may also be used to preserve, at least to some extent, some positions in the sequence of the original polypeptide chain.

One of the rules employed in amino acid sequence alterations stem from highly conserved sequence patterns at specific positions, which are typically exhibited in families of structurally similar proteins. According to some embodiments of the present invention, the rules by which a substitution of amino acids is dictated during a sequence design procedure include position-specific scoring matrix values, or PSSMs (Box 6 in FIG. 1).

A "position-specific scoring matrix" (PSSM), also known in the art as position weight matrix (PWM), or a position-specific weight matrix (PSWM), is a commonly used representation of recurring patterns in biological sequences, based on the frequency of appearance of a character (monomer; amino acid; nucleic acid etc.) in a given position along the sequence. Thus, PSSM represents the log-likelihood of observing mutations to any of the 20 amino acids at each position. PSSMs are often derived from a set of aligned sequences that are thought to be structurally and functionally related and have become widely used in many software tools for computational motif discovery. In the context of amino acid sequences, a PSSM is a type of scoring matrix used in protein BLAST searches in which amino acid substitution scores are given separately for each position in a protein multiple sequence alignment. Thus, a Tyr-Trp substitution at position A of an alignment may receive a very different score than the same substitution at position B, subject to different levels of amino acid conservation at the two positions. This is in contrast to position-independent matrices such as the PAM and BLOSUM matrices, in which the Tyr-Trp substitution receives the same score no matter at what position it occurs. PSSM scores are generally shown as positive or negative integers. Positive scores indicate that the given amino acid substitution occurs more frequently in the alignment than expected by chance, while negative scores indicate that the substitution occurs less frequently than expected. Large positive scores often indicate critical functional residues, which may be active site residues or residues required for other intermolecular or intramolecular interactions. PSSMs can be created using Position-Specific Iterative Basic Local Alignment Search Tool (PSI-BLAST) [Schäffer, A.A. et al., *Nucl. Acids Res.*, 2001, 29(14), pp. 2994-3005], which finds similar protein sequences to a query sequence, and then constructs a PSSM from the resulting alignment. Alternatively, PSSMs can be retrieved from the National Center for Biotechnology Information Conserved Domains Database (NCBI CDD) database, since each conserved domain is represented by a PSSM that encodes the observed substitutions in the seed alignments. These CD records can be found either by text searching in Entrez Conserved Domains or by using Reverse Position-Specific BLAST (RPS-BLAST), also known as CD-Search, to locate these domains on an input protein sequence.

In the context of some embodiments of the present invention, a PSSM data file can be in the form of a table of integers, each indicating how evolutionary conserved is any one of the 20 amino acids at any possible position in the sequence of the designed protein. As indicated hereinabove, a positive integer indicates that an amino acid is more probable in the given position than it would have been in a random position in a random protein, and a negative integer indicates that an amino acid is less probable at the given position than it would have been in a random protein. In general, the PSSM scores are determined according to a combination of the information in the input MSA and general information about amino acid substitutions in nature, as introduced, for example, by the BLOSUM62 matrix [Eddy, S. R., *Nat Biotechnol*, 2004, 22(8):1035-6].

In general, the method presented herein can use the PSSM output of a PSI-BLAST software package to derive a PSSM for both the original MSA and all sub-MSA files. A final PSSM input file, according to some embodiments of the present invention, includes the relevant lines from each PSSM file. For sequence positions that represent a secondary structure, relevant lines are copied from the PSSM derived from the original full MSA. For each loop, relevant lines are copied from the PSSM derived from the sub-MSA file representing that loop. Thus, according to some embodiments of the present invention, a final PSSM input file is a quantitative representation of the sequence data, which is incorporated in the structural calculations, as discussed hereinbelow.

According to some embodiments of the present invention, MSA and PSSM-based rules determine the unsubstitutable positions and the substitutable positions in the amino acid sequence of the original polypeptide chain, and further determine which of the amino acid alternatives will serve as candidate alternatives in the single position scanning step of the method, as discussed hereinbelow.

Key Residues:

The method, according to some embodiments of the present invention, allows the incorporation of information about the original polypeptide chain and/or the wild type protein. This information, which can be provided by various sources, in incorporated into the method as part of the rules by which amino acid substitutions are governed during the design procedure. Albeit optional, the addition of such information is advantageous as it reduces the probability of the method providing results which include folding- and/or function-abrogating substitutions. In the examples presented in the Example section below, valuable information about activity has been employed successfully as part of the rules.

To decrease the probability of sequences leading to misfolding during the sequence design process, residues that are known to be involved in structure stabilization, such as, residues that have an impact on correct folding (e.g., cysteines involved in disulfide bridges), necessary conformation change and allosteric communication with a functional site, and residues involved in posttranslational modifications, may be identified as "key residues" (Box 8 in FIG. 1).

To further decrease the probability to reduce or abolish function during the sequence design process, residues that are known to be involved in any desired function or affect a desired attribute, may be identified as key residues. Positions occupied by key residues are regarded as unsubstitutable positions, and are fixed as the amino acid that occurs in the original polypeptide chain.

The term "key residues" refer to positions in the designed sequence that are defined in the rules as fixed (invariable), at least to some extent. Sequence positions which are occupied by key residues constitute a part of the unsubstitutable positions.

Information pertaining to key residues can be extracted, for example, from the structure of the original polypeptide chain (or the template structure), or from other highly similar structures when available. Exemplary criteria that can assist in identifying key residues, and support reasoning for fixing an amino-acid type or identity at any given position, include:

For enzymes catalyzing reactions of substrate molecules in an active site, key residues may be selected within a radius of about 5-8 Å around the substrate binding site, as may be inferred from complex crystal structures comprising a substrate, a substrate analog, an inhibitor and the like.

For metal binding proteins, key residues may be selected within about 5-8 Å around a metal atom.

Key residues may be selected within about 5-8 Å from any protein interface that involves the chain of interest in an oligomers, as interacting chains are oftentimes involved in dimerization interfaces, binding ligands or protein-substrates interactions.

Key residues may be selected within about 5-8 Å from DNA/RNA chains interacting with the protein of interest.

For proteins involved in immunogenicity, key residues may be selected within about 5-8 Å from the epitope region.

It is noted that the shape and size of the space within which key residues are selected is not limited to a sphere of a radius of 5-8 Å; the space can be of any size and shape that corresponds to the sequence, function and structure of the original protein.

It is further noted that specific key residues may be provided by any external source of information (e.g., a researcher).

When the template structure, the PSSM file (which is based on the full MSA and any optional context specific sub-MSA), and the identification of key residues, unsubstitutable positions and the substitutable positions are provided, the method presented herein can use these data to provide the modified polypeptide chain starting from the original polypeptide chain.

Main Method Steps:

According to some embodiments of the present invention, the method presented herein includes a step that determines which of the positions in the amino-acid sequence of the original polypeptide chain will be subjected to amino-acid substitution and which amino acid alternatives will be assessed. (referred to herein as substitutable positions), and in which positions in the amino acid sequence of the original polypeptide chain the amino-acid will not be subjected to amino-acid substitution (referred to herein as unsubstitutable positions).

In a second step, (that is the single position scanning step), a position-specific stability score is given to each of the allowed amino acid alternatives at each substitutable position (see definition of substitutable positions hereinabove). A comprehensive list of amino acid alternatives that have a position-specific stability score below −0.45 r.e.u. (i.e., are predicted to be stabilizing) is referred to herein as the "sequence space". This list is used as input for another design method step, which includes a combinatorial generation of all, or some, of the possible sequences (designed sequences), using all or some of the position-specific amino acid alternatives.

It is noted that the detailed description of the method presented herein is using some terms, units and procedures with are common or unique to the Rosetta™ software package, however, it is to be understood that the method is capable of being implemented using other software modules and packages, and other terms, units and procedures are therefore contemplated within the scope of the present invention.

According to some embodiments of the invention, advantageous of the method presented herein also stem from the following factors:

(a) The method provides combinatorially generated modified polypeptide chain (protein variants) containing tens of amino-acid substitutions (mutations). In one exemplary case, the method provided a variant with 67 mutations (see hAChE results), while none of the presently known methods even attempts to provide such a broad combinatorial solution.

(b) The procedure by which substitutable positions and amino-acid alternatives are determined in preparation for the combinatorial step ensures that each mutation is independently predicted to be stabilizing. A strict acceptance threshold may be used to reduce the probability of false positive mutations. A low rate of false positives is essential to allow a significant and reliable combinatorial design, and this low rate is partially achieved through a single position scanning step, as discussed hereinbelow.

(c) The reliance on a combination of two orthogonal sources of information-structure based energy calculations and sequence data calculations. The combination of both calculations enables them to compensate for biases common to each source of information. The weighted combination of these two sources of information improves the accuracy of the method presented herein. In addition, the sequence data contains information pertaining to key residues and therefore contributes in avoiding folding- and function-abrogating substitutions.

Preliminary results indicate that the method, according to some embodiments of the present invention, captures optimal sequences that other methods specifically search for, such as mutations to prolines in loop regions, supercharging (increasing the number of charged residues), promoting mutations that afford salt bridges, hydrogen bonds and tighter packing. Such substitutions are suggested by the method presented herein solely by using total energy calculations without aiming a specific type of mutation.

Single Position Scanning

According to some embodiments of the present invention, the step of determining the amino-acid alternatives which can substitute the amino-acid at each of the substitutable positions in the amino acid sequence of the original polypeptide chain, is referred to herein as "single amino acid sequence position scanning", or "single position scanning" (Box 10 in FIG. 1). This step of the method, according to some embodiments of the present invention presented herein, is carried out by individually scanning each of the predefined amino acid alternatives at each of the substitutable positions in the original polypeptide chain, using the PSSM scores as described hereinabove. The single position scanning step is conducted in order to determine which amino acid alternatives are favorable per each scanned substitutable position, by determining the change in free energy (e.g., in Rosetta energy units, or r.e.u) upon placing each of the amino-acid alternatives at the scanned position. The rate at which free energy is changed is correlated to a stability score, which is referred to herein as "a position-specific stability scoring".

A substitutable position is defined by:
i. not being a key position; and
ii. having at least one amino acid alternative that has a PSSM score equal to, or greater than 0 (zero).

At each substitutable position only amino acids having a non-negative PSSM score (i.e. equal to or greater than 0), are subjected to the single position scanning step. This sequence-based restriction, together with restrictions resulting from key residues (functional), typically reduces the scanning space from all positions in the sequence to a fewer positions, and further reduces the scanning space at each of these positions from 20 amino acid alternatives to about 1-10 alternatives. The single position scanning step iterates over the polypeptide chain positions while skipping key residues and unsubstitutable positions, and for each substitutable position it iterates only over the amino acid alternatives that have a PSSM score equal to or greater than 0 to determine their position specific stability score.

For example, in some positions, the original amino acid is conserved such that that all other amino acid alternatives receive a negative PSSM score, leading to a sampling space of 1; as a result, this position will no longer be considered substitutable. In other positions the sequence alignment shows greater variability, meaning that this position is not conserved; however, even for such positions the variability of possible amino acid ranges from about 1 to 10, as indicated by the PSSM score, and not all 20 amino acid alternatives.

Once a set of substitutable positions and their corresponding amino acid alternatives has been determined, a position-specific stability scoring is determined for each alternative. In some embodiments, for each alternative, including the original amino acid at that position, the position-specific stability scoring is determined by subjecting a single substitution variant of the template structure (SSVTS), differing from the initial template structure by having the alternative amino acid in place of the original amino acid, to a global energy minimization, as this term is defined herein, and the difference in total free energy ($\Delta G$) with respect to that of the (refined) template structure is recorded as the position-specific stability scoring for that amino acid alternative.

In some embodiments, the position-specific stability scoring is determined by subjecting the SSVTS to a local energy minimization. In such embodiments, which are advantageous in the sense of computational costs, the position-specific stability scoring is determined for each amino acid alternative, including the original amino acid at that position, by defining a weight fitting shell around the position within which all residues are subjected to a local energy minimization (weight fitting within the weight fitting shell) to determine the lowest energy arrangement for each amino acid within the shell. In case a position within the shell is occupied by a key residue, the key residue is not subjected to amino acid substitution refinement, and is subjected only to small range energy minimization without repacking. In some embodiments, the weight fitting shell has a radius of about 5 Å; however, other sizes and shapes of weight fitting shells are contemplated within the scope of the method presented herein.

According to some embodiments of the present invention, the local energy minimization is effected for amino acid residues of the modified polypeptide chain having at least one atom being less than about 5 Å from at least one atom of the position-specific amino acid alternative, thereby defining a 5 Å weight fitting shell. According to some embodiments, the weight fitting shell is defined as a 6 Å shell, a 7 Å shell, an 8 Å shell, a 9 Å shell or a 10 Å shell, while greater shells are contemplated within the scope of some embodiments of the present invention.

For any form of energy minimization procedure, implemented in the context of embodiments of the present invention, sequence data is incorporated as part of the energy calculations. The energy function contains the standard physico-chemical energy terms, such as used in the RosettaDesign software suite, and two additional terms: one is the coordinate constraint used also at the template structure refinement (see above), and the second is a PSSM-related term, which is the PSSM score (value) multiplied by a weight factor. A PSSM-related weight factor can be determined, for example, in a benchmark study. The value of −0.4 was determined as demonstrated in the benchmark study presented in Example 1 hereinbelow, and further validated in another benchmark study, presented in Example 2 hereinbelow).

According to some embodiments of the present invention, the PSSM score (value) of each of the amino acid alternatives (or amino acid substitutions) is at least zero.

When using the Rosetta™ suite, of each amino acid alternative, the position-specific stability scoring is determined by calculating the total free energy of the SSVTS with respect to the template structure, and the position-specific stability scoring is expressed in r.e.u.

According to some embodiments of the present invention, the position-specific stability scoring of each of the amino acid alternatives (or amino acid substitutions) is equal or smaller than zero. It is noted that a negative ΔΔG value means that the total free energy of a tested entity is lower than the total free energy of the reference entity, and thus the tested entity is considered "more relaxed energetically", or more stable energetically. In the context of embodiments of the present invention, negative position-specific stability scoring is correlated with lower ΔG of folding, which typically indicate higher structure stabilization; however, in order to reduce the probability to incorporate deleterious mutations in the final designed sequence, a minimal (least negative) acceptance threshold is imposed; thereby only amino acid alternatives that have ΔΔG values lower than this acceptance threshold will be permitted into the next step of the method (Box 11 in FIG. 1).

As used herein, the term "acceptance threshold" refers to a free energy difference ΔΔG value, which is used to determine if a given amino acid alternative, having a given position-specific stability scoring (also expressed in ΔΔG units), will be used in the combinatorial design step of the method presented herein.

Typically, the minimal and thus most permissive (least negative ΔΔG value) acceptance threshold can be determined in a benchmark study, such as those presented in the Examples section hereinbelow. In the presented studies it was found that a minimal acceptance threshold of −0.45 r.e.u is permissive enough to provide sufficient substitutable positions with sufficient amino acid alternatives substantially without introducing false positive substitutions. It is noted herein that the method, according to some embodiments of the invention, is not limited to any particular minimal acceptance threshold, and other values are contemplated within the scope of the invention.

The single position scanning step of the method (Box 10 in FIG. 1) generates a limited list of possible amino acid substitutions, referred to herein as a "sequence space", as this term is defined hereinbelow. For each acceptance threshold the output list contains all amino acid alternatives that had a ΔΔG value (i.e. position-specific stability score) more negative than the acceptance threshold (lists from stricter thresholds are subsets of lists from more permissive thresholds; see, FIGS. 2A-D). The lists serve as input for the next and final combinatorial step of the method, and each list constitutes a "sequence space", as this term is defined hereinbelow. Briefly, a sequence space is a subset of substitutions, each predicted to improve structural stability, which is greatly reduced in size compared to the theoretical space of all possible substitutions at any given position, which is $20^n$, wherein 20 is the number of naturally occurring amino acids and n is the number of positions in the polypeptide chain).

Combinatorial Design

The next step of the method presented herein, according to embodiments of the present invention, is a combinatorial design of the entire amino acid sequence of the modified polypeptide chain, wherein numerous amino acid substitutions are simultaneously introduced to the sequence of the original polypeptide chain. A combinatorial design step is performed independently for each acceptance threshold that was defined in the previous single-position scanning step. As demonstrated in the Examples section below, this combinatorial design step typically converges for each acceptance threshold.

During the combinatorial step only amino acid alternatives that passed the given acceptance threshold are allowed to permute at the corresponding substitutable positions. In other words, for each such position only amino acid alternatives that have a position-specific stability scoring more negative than the given acceptance threshold are sampled combinatorially. All other residues are subjected only to repacking and conformational free energy minimization. The combinatorial step yields a final variant with a combination of mutations that are all compatible with one another.

In a single combinatorial design iteration per one acceptance threshold value (Box 12 in FIG. 1), the method converges to generate a single modified polypeptide chain. The modified polypeptide chain includes numerous amino acid substitutions (typically between 2%-15% of the polypeptide chain), and represents a specific combination of substitutions selected from the sequence space.

According to some embodiments, a separate combinatorial design iteration is effected for each of a series of acceptance thresholds, wherein for each iteration, only amino acid alternatives that passed the next acceptance threshold in the series are allowed to permute at the corresponding substitutable positions (Box 13 in FIG. 1).

Figure 2A:
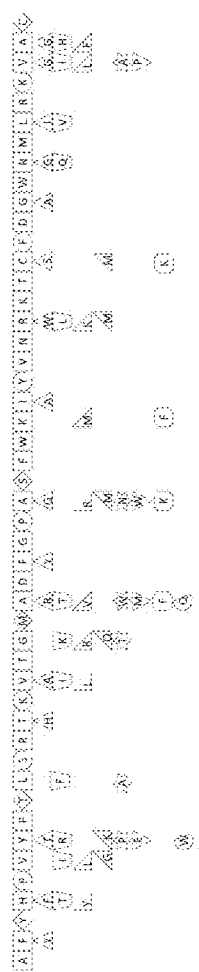
Figure 2B:
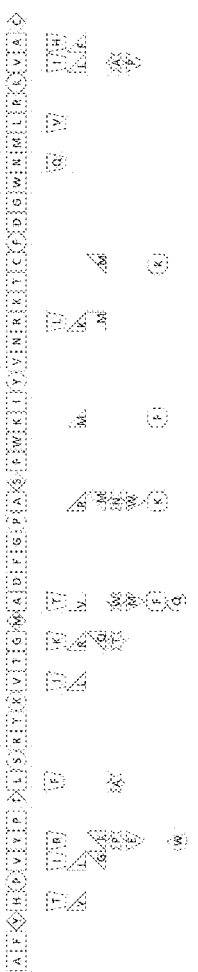
Figure 2C:
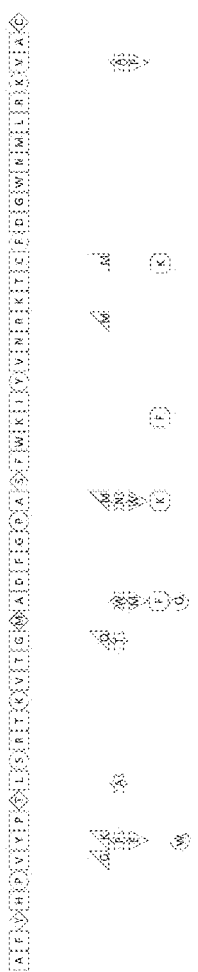
Figure 2D:
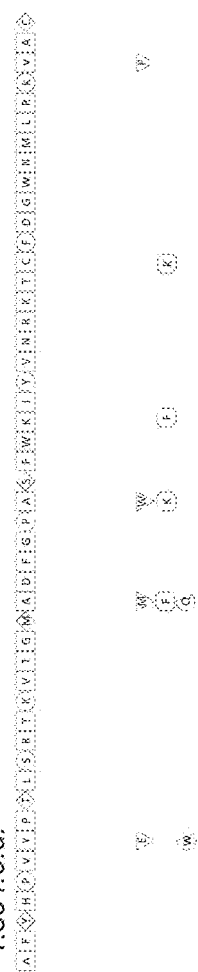

FIGS. 2A-D are simplified illustrations of the output of the single position scanning step and the input of the iterative combinatorial design step of the method provided herein, according to some embodiments of the present invention, wherein FIG. 2A shows the input for a combinatorial step iteration based on the exemplary acceptance threshold of −0.45 r.e.u, wherein the various positions of the original polypeptide chain (SEQ ID No. 12; top row) comprise positions that did not have even a single non-WT amino acid alternative that had position-specific stability score below the exemplary acceptance threshold of −0.45 r.e.u, and are therefore defined as unsubstitutional positions during the combinatorial design step (marked by diamonds, circles, and squares if the latter do not have any other shapes stacked thereunder), and substitutable positions during the combinatorial step (for which at least one amino acid alternative passed the single position scanning step; marked by squares with other shapes stacked thereunder representing the amino acid alternatives that passed the exemplary acceptance threshold). FIGS. 2B-D represent the inputs for combinatorial step iterations based on stricter thresholds and therefore show smaller sets of combinatorially permuted amino acid alternatives, as the input is being reduced for each stricter acceptance threshold value, according to some embodiments of the present invention. For example, amino acid alternatives marked as triangles are amino acid alternatives that have a position-specific stability scoring below the exemplary permissive acceptance threshold of −0.45 r.e.u, but above the next stricter acceptance threshold of −0.75 r.e.u, according to some embodiments of the present invention.

Thereafter, each of the combinatorially generated designed sequences, obtained at each combinatorial design iteration, is threaded on the template structure to thereby generate a plurality of designed structures. While the SSVTS single substitution, the each of the designed structures has multiple substitutions, and thus referred to herein as a multiple substitution variant of the template structure (MSVTS).

Thereafter, each of the designed structures is subjected to a global energy minimization, based on the rules presented hereinabove, and a minimized energy scoring is determined to each of the designed structures relative to the total free energy of the template structure. According to some embodiments of the present invention, the designed structures are sorting according to the minimized energy scoring.

According to some embodiments, the global energy minimization at the combinatorial design step is similar to the template structure refinement procedure in terms of the weight fitting routines and rules (repacking and backbone minimization using the same coordinate constraint and the same PSSM-related energy terms).

While reducing the present invention to practice, an acceptance threshold value of −0.45 r.e.u has been found to be sufficiently permissive in terms of providing a sequence space that has a high probability to include optimal stabilized sequences while minimizing almost to zero the risk of false positives. While further reducing the present invention to practice, it has been found that most single amino acid substitutions reduce the total free energy by up to −2 r.e.u independently. Therefore, use of an acceptance threshold much stricter (lower; more negative) than −2 r.e.u may not provide a sufficiently broad sequence space to be used as input in the following combinatorial step to allow the generation of an optimal variant with a significant stability advantage. In the range between −0.45 r.e.u and −2 r.e.u, an arbitrary set of 7 acceptance threshold values represents an effective sampling set, since there is little value in sampling the acceptance threshold value range in increments of less than about 0.2-0.25 r.e.u. The experimental synthesis and validation of up to seven designed variants is generally considered time- and cost-affordable.

According to some embodiments of the invention, the combinatorial design step is repeated (reiterated) using several different acceptance thresholds, e.g., starting with the most permissive value of −0.45 r.e.u and continuing using stricter (lower) values for subsequent iteration. For example, the acceptance thresholds used in each iteration may be −0.45, −0.75, −1.0, −1.25, −1.5, −1.8, −2.0 r.e.u.

A combinatorial design approach is advantageous since it substantially avoids incidents wherein substitutions that passed the single position scanning may still be incompatible with one another, due to several reasons. For example:

(a) if two substitutions in the output list from the single position step are close to each other in the protein chain, the amino acid alternatives may clash sterically.

(b) If a set of substitutions from neutral/positive amino acids to negative amino acid alternatives is introduced at once, it may interrupt with the charge/polarity balance at a certain region of the modified polypeptide chain, leading to misfolding and reduced solubility.

(c) A substitution that is not the top-scoring substitution in its position with respect to the original sequence, may become more favorable than the top scoring substitution when introduced simultaneously with another substitution(s).

For example, in a hypothetical single position scanning, original position A101 is found to be substitutable with both V and T alternatives. V had a position-specific stability scoring of −1.5 r.e.u while T had a position-specific stability scoring of −0.67 r.e.u. Taken independently, an A101V substitution seems to be a more favorable substitution. However, original position K108 is structurally proximal to original position A101, and K108 is found to be substitutable with N alternative. According to some embodiments of the invention, the combination of substitutions A101T and K108N may be found more favorable in the combinatorial step, since the two substitutions are capable of forming a hydrogen bond (involving the T hydroxyl group), while T alternative in position 101 would not form a hydrogen bond with the original K108, due to conformational constraints, compared to N alternative in that same 108 position. Thus, while being less favorable in the context of the original polypeptide chain, the A101T substitution becomes more favorable when introduced during combinatorial step together with the K108N substitution.

For each combinatorial design iteration, the final output is a single MSVTS that is expected to be significantly more stable than the original polypeptide chain. It is noted herein that the combinatorial design step, coming after the single position scanning, is highly convergent, namely, if repeated several times using the same sequence space, this step provides either an identical final sequences or very similar (degenerate) sequences and therefore, according to some embodiments of the presented invention, one trajectory of a combinatorial design step per acceptance threshold is performed. The number of substitutions typically varies between 2-12% of the protein full length. Since the method presented herein uses multiple combinatorial design iterations, each for a different acceptance threshold value based on the single position scanning, the method provides several different sets of MSVTS, one for each acceptance threshold value. The MSVTS obtained using the strictest threshold (e.g., −2.0 r.e.u) will contain the smallest number of substitutions, and MSVTS obtained using the most permissive threshold (e.g., −0.45 r.e.u) will contain the largest number of mutations. While the combinatorial step provides MSVTSs that are predicted to exhibit significant improvement in one or more of the desired properties, some other combinations of substitutions, taken from the sequence spaces defined in the previous step, may lead to even more optimal MSVTSs.

According to some embodiments of the present invention, the method is implemented effectively for original polypeptide chains that comprise more than 100 amino acids (aa). In some embodiments, the original polypeptide chains comprise more than 110 aa, more than 120 aa, more than 130 aa, more than 140 aa, more than 150 aa, more than 160 aa, more than 170 aa, more than 180 aa, more than 190 aa, more than 200 aa, more than 210 aa, more than 220 aa, more than 230 aa, more than 240 aa, more than 250 aa, more than 260 aa, more than 270 aa, more than 280 aa, more than 290 aa, more than 300 aa, more than 350 aa, more than 400 aa, more than 450 aa, more than 500 aa, more than 550 aa, or more than 600 amino acids.

According to some embodiments of the present invention, the method presented herein provides modified polypeptide chains (MSVTS) having more than 5 amino acid substitutions (mutations), more than 6 substitutions, more than 7 substitutions, more than 8 substitutions, more than 9 substitutions, more than 10 substitutions, more than 11 substitutions, more than 12 substitutions, more than 13 substitutions, more than 14 substitutions, more than 15 substitutions, more than 16 substitutions, more than 17 substitutions, more than 18 substitutions, more than 19 substitutions, more than 20 substitutions, more than 25 substitutions, more than 30 substitutions, more than 35 substitutions, more than 40 substitutions, more than 45 substitutions, more than 50 substitutions, more than 60 substitutions, more than 70 substitutions, more than 80 substitutions or more than 90 amino acid substitutions compared to the starting original polypeptide chain.

Sequence Space:

According to some embodiments of the present invention, after filtering key residues and imposing a free energy acceptance threshold, the number of substitutable positions in a given sequence is greatly reduced, thereby providing a wide yet manageable combinatorial sequence space from which designed sequences can be selected, instead of the theoretical unmanageable space of $20^n$. Thus, the term "sequence space" refers to a set of substitutable positions, each having at least one optional substitution over the WT amino acid at the given position.

A sequence space is therefore a result of a certain acceptance threshold; each acceptance threshold produces a different sequence space, where sequence spaces defined by stricter acceptance thresholds are contained within larger sequence spaces defined by more permissive acceptance thresholds. As discussed hereinabove, in order to avoid false positives the acceptance threshold can be small and should be negative, wherein –2 r.e.u is considered to be highly restrictive (strict) and –0.45 r.e.u is highly permissive. The sequence space obtained by using acceptance threshold of –0.45 r.e.u will inevitably be larger (permissive) than a sequence space obtained by using acceptance threshold of –2.00 r.e.u (strict). Experimental use of the method presented herein to produce actual proteins has shown that an intermediate acceptance threshold produces an optimal sequence space. In fact, the sequence space is a sub-space of the broader space defined by the PSSM rules.

An exemplary and general mean to present a sequence space is in a list of sequence positions based on the wild-type sequence numbering, $P_1$, $P_2$, P3, . . . , Pn, wherein each position is either designated as a key residue, namely an amino acid as found in the WT, $AA_{WT}$, or a position that can take any one amino acid from a limited list comprising at least one alternative amino acid based on the PSSM and energy minimization analysis, $AA_m$, wherein m is a number denoting one of the naturally occurring amino acids, e.g., A=1, R=2, N=3, D=4, C=5, Q=6, E=7, G=8, H=9, L=10, I=11, K=12, M=13, F=14, P=15, S=16, T=17, W=18, Y=19 and V=20 (aa numbering is arbitrary and used herein to demonstrate a general representation of a sequence space.

For example, the sequence space can be presented as:

$P_1$: $AA_{WT}$, $AA_5$, $AA_8$, and $AA_{12}$;

$P_2$: $AA_{WT}$;

$P_3$: $AA_{WT}$ and $AA_{16}$;

$P_4$: $AA_{WT}$, $AA_1$, $AA_3$, $AA_6$, $AA_{10}$, and $AA_{14}$;

$P_5$: $AA_{WT}$, $AA_4$, $AA_8$, and $AA_{11}$;

. . .

$Pn$: $AA_{WT}$, $AA_m$, $AA_m$, $AA_m$, $AA_m$, and $AA_m$, ;

whereas in this general example, $P_1$ has four alternative amino acids, $P_2$ is a key residue and so forth.

According to some embodiments of the present invention, the sequence space can be further limited by imposing a stricter acceptance threshold, or expanded by imposing a more permissive acceptance threshold. In general, the value of −0.45 r.e.u has been found to be adequately permissive; however sequence space based on an acceptance threshold larger than −0.45 r.e.u (e.g., −0.2 r.e.u) or based on an acceptance threshold smaller than −2.00 r.e.u (e.g., −2.1 r.e.u) are also contemplated.

In the context of embodiments of the present invention, any non-naturally occurring designed protein which is homologous to an original protein as defined herein (e.g., at least 20% or at least 30% sequence identity), and having a choice of any 6 or more substitutions relative to the wild-type sequence that are selected from a sequence space as defined herein, is a product of the method presented herein, and is therefore contemplated within the scope of the present invention.

In the Examples section that follows below, a sequence space based on acceptance threshold of −0.45 r.e.u is presented for some of the exemplary proteins on which the method has been demonstrated. Any designed sequence having any choice of any 6 or more substitutions relative to the wild-type sequence that are selected from the presented sequence space, and that exhibits at least one of:

a thermal denaturation temperature being equal or higher than the thermal denaturation temperature of the wild type protein;

a solubility being equal or higher than the solubility of the wild type protein;

a degree of misfolding being equal or lower than the degree of misfolding of the wild type protein;

a half-life being equal or longer than the half-life of the wild type protein;

a specific activity being equal or higher than the specific activity of the wild type protein; and/or a recombinant expression level being equal or higher than the recombinant expression level of the wild type protein, is contemplated within the scope of the present invention.

It is noted herein that embodiments of the present invention encompass any and all the possible combinations of amino acid alternatives in any given sequence space afforded by the method presented herein (all possible variants stemming from the sequence space as defined herein).

It is further noted that in some embodiments of the present invention, the sequence space resulting from implementation of the method presented herein on an original protein, can be applied on another protein that is different than the original protein, as long as the other protein exhibits at least 30%, at least 40%, or at least 50% sequence identity and higher. For example, a set of amino acid alternatives, taken from a sequence space afforded by implementing the method presented herein on a human protein, can be used to modify a non-human protein by producing a variant of the non-human protein having amino acid substitutions at the sequence-equivalent positions. The resulting variant of the non-human protein, referred to herein as a "hybrid variant", would then have "human amino acid substitutions" (selected from a sequence space afforded for a human protein) at positions that align with the corresponding position in the human protein. In some embodiments of the present invention, any such hybrid variant, having at least 6 substitutions that match amino acid alternatives in any given sequence space afforded by the method presented herein (all possible variants stemming from the sequence space as defined herein), is contemplated and encompassed in the scope of the present invention.

Selection of Variants for Experimental Testing:

According to some embodiments of the present invention, the method presented herein provides a low throughput/low cost solution for obtaining stabilized proteins with other improved functional features. Thus, the method is configured to converge at a relatively small number of modified polypeptide chains (MSVTS), depending on the number of acceptance threshold iterations used in the combinatorial design step (discussed above).

As discussed hereinabove, selecting at least one of the plurality of designed structures (MSVTS), each corresponding to a modified polypeptide chain, is based on the minimized energy scoring calculated for that MSVTS. According to some embodiments of the present invention, the selection of a modified polypeptide chain is based on a minimal value for the minimized energy scoring which was calculated for the corresponding designed structure (Box 14 in FIG. 1).

For example, when using 7 acceptance threshold values, 1-5 modified polypeptide chains are selected. The selection of MSVTS may follow several criteria, according to some embodiments of the present invention, such as:

1) a −0.45 r.e.u acceptance threshold-based modified polypeptide chains may be selected since it is the most permissive in terms of the number of amino acid substitutions, and therefore holds the potential to achieve the most dramatic effect on the desired properties. In rare cases where the number of substitutions in such modified polypeptide chain is higher than 10% of the full length of the polypeptide chain, the −0.75 r.e.u acceptance threshold-based modified polypeptide chain may be selected instead.

2) The other 1-4 variants may be selected according to the acceptance thresholds that maximize the difference between the selected variants. In many cases two consecutive acceptance thresholds values afford similar variants; thus, selecting variants from non-consecutive acceptance thresholds affords a more diverse set of variants 3) It has been observed that at a certain acceptance threshold value the number of mutations drops significantly. This behavior is not linear and is different in different protein cases; hence, selection of variants in which the number of mutations is less than 2% of the protein length is less desired.

4) In some cases, especially for short polypeptide chains or polypeptide chains for which the constraints were stricter (many key residues), the MSVTS output, based on the most permissive acceptance threshold, may already contain a number of mutations that is less than 5% of the protein length. In such a case only 1-2 modified polypeptide chains may be selected for further studies. For other cases, where the polypeptide chain is large and/or constraints are moderate, 3-5 modified polypeptide chains may be selected for further studies, depending on the user's preference and experimental abilities.

It is noted that a dramatic change in the protein's characteristics (e.g., stability) is not necessarily desired, and a modest change may be sufficient. In addition, there might be a need to keep the sequence as close as possible to that of the original polypeptide chain, for any reason (e.g., immunological considerations and the like); therefore few variants with varied number and type of substitutions are typically selected for further studies.

Additional Features of the Method:

Use of the method presented herein is contemplated also for multi-chain proteins, according to some embodiments of the present invention. In such cases, rather than defining the residues at the chain-chain interface as key residues (fixed residues), the method is implemented by using symmetry considerations for homo-oligomers, or standard rigid-body sampling (docking) calculations for each of the chains in a hetero-oligomer Use of the method presented herein is contemplated also for executing the single position scanning step with pairs of near-by positions. This feature broadens the mutation space and allows the introduction of pairs or higher-order sets of stabilizing amino acid substitutions (as in epistatic mutations), where individual substitutions would be destabilizing, and is expected to the introduction of more stabilizing substitutions at the protein core.

A Non-naturally Occurring Designed Protein:

As discussed hereinabove and demonstrated in the Examples section that follows below, the method presented herein is general and effective in providing amino acid sequences of polypeptide chains that have been modified thereby such that a protein that includes such a modified polypeptide chain is more stable, compared to a wild type protein that includes the original polypeptide chain corresponding to the modified polypeptide chain.

According to an aspect of some embodiments of the present invention, there is provided a non-naturally occurring designed protein which includes at least one modified polypeptide chain, wherein the substitutions are modifying the designed protein relative to the corresponding wild type protein, as determined by at least one of:

a thermal denaturation temperature of the designed protein being equal or higher than a thermal denaturation temperature of the wild type protein;

a solubility of the designed protein being equal or higher than a solubility of the wild type protein;

a degree of misfolding of the designed protein being equal or lower than a degree of misfolding of the wild type protein;

a half-life of the designed protein being equal or longer than a half-life of the wild type protein;

a specific activity of the designed protein being equal or higher than a specific activity of the wild type protein; and a recombinant expression level of the designed protein being equal or higher than a recombinant expression level of the wild type protein.

According to some embodiments of the present invention, the modified polypeptide chain in the designed protein has at least six amino acid substitutions relative to the original polypeptide chain in the corresponding wild type protein. In some embodiments, the modified polypeptide chain comprises more than 5 amino acid substitutions (mutations), more than 6 substitutions, more than 7 substitutions, more than 8 substitutions, more than 9 substitutions, more than 10 substitutions, more than 11 substitutions, more than 12 substitutions, more than 13 substitutions, more than 14 substitutions, more than 15 substitutions, more than 16 substitutions, more than 17 substitutions, more than 18 substitutions, more than 19 substitutions or, more than 20 amino acid substitutions, more than 25 substitutions, more than 30 substitutions, more than 35 substitutions, more than 40 substitutions, more than 45 substitutions, more than 50 substitutions, more than 60 substitutions, more than 70 substitutions, more than 80 substitutions or more than 90 substitutions relative to the original polypeptide chain.

According to some embodiments of the present invention, the original polypeptide chain comprises more than 100 amino acids (aa). In some embodiments, the original polypeptide chain comprises more than 110 aa, more than 120 aa, more than 130 aa, more than 140 aa, more than 150 aa, more than 160 aa, more than 170 aa, more than 180 aa, more than 190 aa, more than 200 aa, more than 210 aa, more than 220 aa, more than 230 aa, more than 240 aa, more than 250 aa, more than 260 aa, more than 270 aa, more than 280 aa, more than 290 aa, or more than 300 amino acids, more than 350 aa, more than 400 aa, more than 450 aa, more than 500 aa, more than 550 aa, or more than 600 amino acids.

According to some embodiments of the present invention, the original polypeptide chain comprises more than 100 amino acids (aa) and the corresponding modified polypeptide chain comprises more than 5 amino acid substitutions (mutations), more than 6 substitutions, more than 7 substitutions, more than 8 substitutions, more than 9 substitutions, more than 10 substitutions, more than 11 substitutions, more than 12 substitutions, more than 13 substitutions, more than 14 substitutions, more than 15 substitutions, more than 16 substitutions, more than 17 substitutions, more than 18 substitutions, more than 19 substitutions or, more than 20, more than 25 substitutions, more than 30 substitutions, more than 35 substitutions, more than 40 substitutions, more than 45 substitutions, more than 50 substitutions, more than 60 substitutions, more than 70 substitutions, more than 80 substitutions or more than 90 amino acid substitutions relative to the original polypeptide chain.

According to some embodiments of the present invention, the original polypeptide chain comprises more than 120 amino acids (aa) and the corresponding modified polypeptide chain comprises more than 5 amino acid substitutions (mutations), more than 6 substitutions, more than 7 substitutions, more than 8 substitutions, more than 9 substitutions, more than 10 substitutions, more than 11 substitutions, more than 12 substitutions, more than 13 substitutions, more than 14 substitutions, more than 15 substitutions, more than 16 substitutions, more than 17 substitutions, more than 18 substitutions, more than 19 substitutions or, more than 20, more than 25 substitutions, more than 30 substitutions, more than 35 substitutions, more than 40 substitutions, more than 45 substitutions, more than 50 substitutions, more than 60 substitutions, more than 70 substitutions, more than 80 substitutions or more than 90 amino acid substitutions relative to the original polypeptide chain.

According to some embodiments of the present invention, the original polypeptide chain comprises more than 140 amino acids (aa) and the corresponding modified polypeptide chain comprises more than 5 amino acid substitutions (mutations), more than 6 substitutions, more than 7 substitutions, more than 8 substitutions, more than 9 substitutions, more than 10 substitutions, more than 11 substitutions, more than 12 substitutions, more than 13 substitutions, more than 14 substitutions, more than 15 substitutions, more than 16 substitutions, more than 17 substitutions, more than 18 substitutions, more than 19 substitutions or, more than 20, more than 25 substitutions, more than 30 substitutions, more than 35 substitutions, more than 40 substitutions, more than 45 substitutions, more than 50 substitutions, more than 60 substitutions, more than 70 substitutions, more than 80 substitutions or more than 90 amino acid substitutions relative to the original polypeptide chain.

According to some embodiments of the present invention, the original polypeptide chain comprises more than 160 amino acids (aa) and the corresponding modified polypeptide chain comprises more than 5 amino acid substitutions (mutations), more than 6 substitutions, more than 7 substitutions, more than 8 substitutions, more than 9 substitutions, more than 10 substitutions, more than 11 substitutions, more than 12 substitutions, more than 13 substitutions, more than 14 substitutions, more than 15 substitutions, more than 16 substitutions, more than 17 substitutions, more than 18 substitutions, more than 19 substitutions or, more than 20, more than 25 substitutions, more than 30 substitutions, more than 35 substitutions, more than 40 substitutions, more than 45 substitutions, more than 50 substitutions, more than 60 substitutions, more than 70 substitutions, more than 80 substitutions or more than 90 amino acid substitutions relative to the original polypeptide chain.

According to some embodiments of the present invention, the original polypeptide chain comprises more than 180 amino acids (aa) and the corresponding modified polypeptide chain comprises more than 5 amino acid substitutions (mutations), more than 6 substitutions, more than 7 substitutions, more than 8 substitutions, more than 9 substitutions, more than 10 substitutions, more than 11 substitutions, more than 12 substitutions, more than 13 substitutions, more than 14 substitutions, more than 15 substitutions, more than 16 substitutions, more than 17 substitutions, more than 18 substitutions, more than 19 substitutions or, more than 20, more than 25 substitutions, more than 30 substitutions, more than 35 substitutions, more than 40 substitutions, more than 45 substitutions, more than 50 substitutions, more than 60 substitutions, more than 70 substitutions, more than 80 substitutions or more than 90 amino acid substitutions relative to the original polypeptide chain.

According to some embodiments of the present invention, the original polypeptide chain comprises more than 200 amino acids (aa) and the corresponding modified polypeptide chain comprises more than 5 amino acid substitutions (mutations), more than 6 substitutions, more than 7 substitutions, more than 8 substitutions, more than 9 substitutions, more than 10 substitutions, more than 11 substitutions, more than 12 substitutions, more than 13 substitutions, more than 14 substitutions, more than 15 substitutions, more than 16 substitutions, more than 17 substitutions, more than 18 substitutions, more than 19 substitutions or, more than 20, more than 25 substitutions, more than 30 substitutions, more than 35 substitutions, more than 40 substitutions, more than 45 substitutions, more than 50 substitutions, more than 60 substitutions, more than 70 substitutions, more than 80 substitutions or more than 90 amino acid substitutions relative to the original polypeptide chain.

According to some embodiments of the present invention, the original polypeptide chain comprises more than 500 amino acids (aa) and the corresponding modified polypeptide chain comprises more than 5 amino acid substitutions (mutations), more than 6 substitutions, more than 7 substitutions, more than 8 substitutions, more than 9 substitutions, more than 10 substitutions, more than 11 substitutions, more than 12 substitutions, more than 13 substitutions, more than 14 substitutions, more than 15 substitutions, more than 16 substitutions, more than 17 substitutions, more than 18 substitutions, more than 19 substitutions, more than 20 substitutions, more than 30 substitutions, more than 40 substitutions, more than 50 substitutions, more than 60 substitutions, more than 70 substitutions or more than 80 amino acid substitutions relative to the original polypeptide chain.

The uniqueness, robustness and generality of the method of computationally designing a modified polypeptide chain starting from an original polypeptide chain, according to some embodiments of the invention presented herein, can be identified in several characteristics of the modified polypeptide which the method can generate (e.g., fingerprints of the method). For example, a designed protein afforded according to some embodiments of the method presented herein, is characterized by amino acid substitution in the core of the protein, which are typically more complicated to design and more often than not result in deleterious mutation when designed by presently known computational protein modification methods. According to some embodiments of the present invention, the shortest distance of Cα of at least one of the amino acid substitutions in the designed protein is at least 6 Å from the water-accessible surface thereof. The depth of the amino acid substitution, as defined herein, can be greater than 6 Å, whereas the water-accessible surface is determined computationally as known in the art [Connolly, M. L., Science, 1983, 221:709-713; and Lins, L. et al., Protein Sci, 2003, 12(7):1406-1417].

Another characteristic of a designed protein produced by the method provided herein is manifested in pairs of substitutions that act cumulatively or synergistically in stabilizing the designed protein. According to some embodiments of the present invention, at least two of the amino acids of the substituted amino acids in the designed protein interact with one another such that the interaction stabilizes the modified protein, as determined by a lower free energy term of the modified protein compared to the original protein, however, these combinations of interacting amino acid substitutions are seen only in some variants afforded by this method, as discussed hereinabove (see, compatible pairs and compatible sets of amino acid substitutions). The joint contribution to the stability of the protein stems from chemical and/or physical interactions based on proximity and orientation of some atoms in the substituted amino acids that lead to a bond formation. According to some embodiments of the present invention, a bond is defined as any one of a covalent bond (about 250 kJ/mol for a disulfide bond), electrostatic (ionic) bond (about 10-50 kJ/mol), van der Waals interaction (about 0.4-4.0 kJ/mol), hydrogen bond (about 12-30 kJ/mol), hydrophobic Interaction (about 40 kJ/mol), or aromatic stacking interaction (about 8-12 kJ/mol or 2-3 kcal/mol), and the like, as these are known in the art. According to some embodiments of the invention, a bond can contribute to the stability of the protein in a degree proportional to the energy of the bond.

It is noted that the method does not require that the substitutions interact in order to stabilize the designed protein. Thus, according to some embodiments of the invention, compatible pairs, or compatible sets of amino acid substitutions, do not interact with one another.

Characterization of a Non-naturally Occurring Designed Protein:

The designed protein can be characterized by several functional and structural attributes, such as Tm, specific activity, expression level in a given expression system, and any other criterion that correlates to its functional and structural stability. These attributes can be compared to those of the corresponding wild type (WT) protein to assess whether the modified polypeptide chain is an improved variant of the original polypeptide chain (Box 15 in FIG. 1).

The experimental protein characterization tests that can determine whether the designed protein has an improved property compared to the wild type protein, may include, for example, an assay indicative of a change in stability. For example, if the method is used to provide a solution to a problem of low expression levels, the assay should indicate the relative amount of protein in equal sized samples of the WT protein versus the designed proteins. Alternatively and additionally, an assay may compare the specific activity of the WT protein versus the designed proteins.

The improved stability of the designed protein, according to some embodiments of the present invention, may be tested by any methodology for determining protein stability, such as improved thermal stability manifested by a higher thermal denaturation temperature (Tm), improved expression levels, improved solubility, lowered misfolding levels, lower aggregation levels, increased half-life, and the like.

According to some embodiments of the present invention, the modification of the designed protein relative to the corresponding wild type protein, is determined by thermal shift assays, wherein the thermal denaturation temperature of the designed protein is higher than the thermal denaturation temperature of the wild type protein or at least equal thereto.

According to some embodiments of the present invention, stability of proteins can be assessed and determined, for example, by thermal shift assays. Thermal shift assays are typically effected by techniques such as, for example, a temperature-melt assay, heat-inactivation assay, a guanidinium-melt assay, differential scanning calorimetry (DSC), circular dichroism (CD), fluorescent spectroscopy, small-angle X-ray scattering (SAXS) and differential scanning fluorimetry (DSF), as these are known and used in the art.

One property which is indicative of an improvement of a designed protein is its solubility, which is indicative of a correct fold and a balanced distribution of charged residues on its surface.

According to some embodiments of the present invention, the modification of the designed protein relative to the corresponding wild type protein, is determined by the ratio of correctly folded to misfolded protein molecules, wherein the degree of misfolding of the designed protein is lower than the degree of misfolding of the wild type protein or at least equal thereto.

As known in the art, misfolded proteins tend to form aggregates, due to reduced solubility thereof, hence any type of protein solubility assay, as known to any person of ordinary skills in the art, would serve well to compare the degree of misfolding of the designed protein relative to the degree of misfolding of the wild type.

According to some embodiments of the present invention, the modification of the designed protein relative to the corresponding wild type protein, is determined by solubility assays, wherein the solubility of the designed protein is higher than the solubility of the wild type protein or at least equal thereto.

Additional technique that can be used to compare the degree of misfolding of the designed protein compared to the corresponding wild type, include single-molecule assays for investigating protein misfolding and aggregation [Hoffmann, A. et al., Phys Chem Chem Phys, 2013, 15(20:7934-48], such as single-molecule fluorescence spectroscopy, single-molecule force spectroscopy and nanopore analysis. Briefly, single-molecule fluorescence spectroscopy is based on measuring the time-dependent fluorescence from individual molecules, typically in the context of confocal or total internal reflection microscopy. Single-molecule force spectroscopy uses a force probe to apply tension as a denaturant to the molecule of interest, wherein structural changes in response to the force, such as unfolding, are monitored by measuring changes in the end-to-end extension of the molecule. Typically the force is applied between two specific points on the protein defined by the attachments to the force probes, including the atomic force microscope (AFM), optical tweezers, and magnetic tweezers. Nanopore analysis involve introduction of nanopores into a lipid membrane (typically using a pore-forming protein such as a-hemolysin) or a solidstate membrane (typically using silicon nanofabrication); a voltage clamp applied across the membrane drives an ionic current through the nanopore; as protein molecules associate with the pore or translocate through it, the current level is reduced; since different structures can modulate the current in different ways, information can be gained about the protein's conformational distribution in the sample.

Specific activity of a protein can serve as a measure for the relative potion of a correctly folded and stable protein. According to some embodiments of the present invention, the modification of the designed protein relative to the corresponding wild type protein is determined by specific activity, wherein the specific activity of the designed protein is higher than the specific activity of the wild type protein or at least equal thereto.

For example, the specific activity of an enzyme can be determined by an enzymatic activity assay, and the specific activity of a binding protein can be determined by a binding assay. Briefly, the specific activity of a protein is typically expressed per milligram of total protein (expressed in μmol min−1 mg−1). Specific activity gives a measurement of active portion of a stable protein in a mixture of misfolded and other proteins. It is the amount of product formed by a protein in a given amount of time under given conditions per milligram of total proteins. Specific activity is equal to the rate of reaction multiplied by the volume of reaction divided by the mass of total protein. The SI unit is katal kg−1, but a more practical unit is μmol mg−1 min−1. In the case of enzymes, specific activity is a measure of enzyme processivity, at a specific (usually saturating) substrate concentration, and is usually constant for a pure enzyme. For elimination of errors arising from differences in cultivation batches and/or misfolded enzyme etc., an active site titration needs to be done. This is a measure of the amount of active enzyme, calculated by, e.g., titrating the amount of active sites present by employing an irreversible inhibitor. The specific activity should then be expressed as μmol min−1 mg−1 active enzyme. If the molecular weight of the enzyme is known, the turnover number, or μmol product sec−1 μmol−1 of active enzyme, can be calculated from the specific activity. The turnover number can be visualized as the number of times each enzyme molecule carries out its catalytic cycle per second.

In the context of a recombinant expression system, a protein's stability can be expressed in the amount of correctly folded and active fraction of the protein in the total expressed protein, in any given recombinant expression system. According to some embodiments of the present invention, the modification of the designed protein relative to the corresponding wild type protein, is determined by a recombinant expression level, wherein the recombinant expression level of the designed protein is higher than the recombinant expression level of the wild type protein or at least equal thereto, as can be assessed by comparing design with WT in activity assays in normalized lysates, and/or by SDS-gels of their supernatant fractions, and/or by the size of aggregated protein fraction, and other means for assessing the amount of soluble, correctly folded and active recombinant protein expression.

Still in the context of a recombinant expression system, a protein's stability can be expressed in the protein's half-life. According to some embodiments of the present invention, the modification of the designed protein relative to the corresponding wild type protein, is determined by half-life assays, wherein the half-life of the designed protein is higher than the half-life of the wild type protein or at least equal thereto.

Different proteins are degraded at different rate. Abnormal and misfolded proteins are quickly degraded, whereas the rate of degradation of normal proteins may vary widely depending on their functions. Enzymes at important metabolic control points may be degraded much faster than those enzymes whose activity is largely constant under all physiological conditions. The N-end rule states that the N-terminal amino acid of a protein determines its half-life (likelihood of being degraded). The rule applies to both eukaryotic and prokaryotic organisms, but with different strength. However, only rough estimations of protein half-life can be deduced from this 'rule', as N-terminal amino acid modification can lead to variability and anomalies, whilst amino acid impact can also change from organism to organism. Other degradation signals, known as degrons, can also be found in sequence. The N-end rule may partially determine the half-life of a protein, and proteins with segments rich in proline, glutamic acid, serine, and threonine (the so-called PEST proteins) have short half-life. Other factors suspected to affect degradation rate include the rate deamination of glutamine and asparagine and oxidation of cystein, histidine, and methionine, the absence of stabilizing ligands, the presence of attached carbohydrate or phosphate groups, the presence of free α-amino group, the negative charge of protein, and the flexibility and stability of the protein. Protein's half-life can be assayed by a variety of techniques, such as pulse-chase analysis and cycloheximide blocking [Zhou, P., *Methods Mol Biol*, Clifton, N.J. Publisher, 2004, 284:67-77].

Expression and/or activity level of the designed proteins, according to some embodiments of the invention, can be determined using methods known in the arts, some examples of which are presented hereinbelow.

Enzyme linked immunosorbent assay (ELISA) method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Radio-immunoassay (RIA) method involves precipitation of the protein of interest (i.e., the designed protein) with a specific antibody and radiolabeled antibody binding protein (e.g., protein A labeled with $I^{125}$) immobilized on a precipitable carrier such as agarose beads. The number of counts in the precipitated pellet is proportional to the amount of protein of interest. In an alternate version of the RIA, a labeled protein of interest and an unlabelled antibody binding protein are employed. A sample containing an unknown amount of protein of interest is added in varying amounts. The decrease in precipitated counts from the labeled protein of interest is proportional to the amount of substrate in the added sample.

Fluorescence activated cell sorting (FACS) method involves detection of a protein of interest in situ in cells by specific antibodies. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical analysis involves detection of a protein of interest in situ in fixed cells by specific antibodies. The specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain.

In situ activity assay involves the use of a chromogenic substrate, which is applied on the cells containing an active enzyme and the enzyme catalyzes a reaction in which the substrate is decomposed to produce a chromogenic product visible by a light or a fluorescent microscope.

In vitro activity assays measure the activity of a particular enzyme in a protein mixture extracted from the cells. The activity can be measured in a spectrophotometer well using colorimetric methods or can be measured in a non-denaturing acrylamide gel (i.e., activity gel). Following electrophoresis the gel is soaked in a solution containing a substrate and colorimetric reagents. The resulting stained band corresponds to the enzymatic activity of the protein of interest. If well calibrated and within the linear range of response, the amount of enzyme present in the sample is proportional to the amount of color produced. An enzyme standard is generally employed to improve quantitative accuracy.

Production of Non-naturally Occurring Designed Protein:

The amino acid sequences of the selected modified polypeptide chains can be used to produce the corresponding proteins, using any protein synthesizer or a biologic recombinant expression system. Thus, according to another aspect of some embodiments of the present invention, there is provided a method of producing a designed protein, as defined and presented hereinabove, which is carried out by:

obtaining an amino acid sequence of a modified polypeptide chain using the method of computationally designing a modified polypeptide chain starting from an original polypeptide chain, according to some of any of the embodiments of the present invention; and expressing the designed protein in any available protein expression system to thereby produce the designed protein.

A product of the method presented herein, according to some embodiments of the present invention, is a set of amino-acid sequences, which are selected for expression and further characterization, and optionally further optimization by directed evolution using experimental in vitro and/or in vivo procedures.

Most generally a designed protein or modified polypeptide chains of a protein can be reverse-translated and reverse-transcripted into a DNA segment encoding the protein or fragment, referred to herein as a genetic template. This genetic template can then be synthesized using established methodologies which are publically and commercially available. 5' and 3' fragments that allow for restriction-ligation reaction or homologous recombination into commonly used pET or other protein-expression plasmids are added to the genetic template through standard PCR extension. The genetic template can then be restricted using compatible restriction enzymes into the expression plasmid or incorporated into the expression plasmid through homologous recombination. Standard expression organisms (bacteria, yeast, phage, insect, plant or mammalian cells) are transformed with the compatible gene-encoding plasmid and expression is induced.

Given the size and complexity of the designed protein, according to some embodiments of the present invention, chemical synthesis is typically not a viable option for expressing an amino-acid sequence afforded by the method presented herein. Instead, living cells and their cellular machinery can be harnessed as biologic expression systems to build and construct the designed proteins based on corresponding genetic templates.

Unlike proteins, the genetic template (DNA) of the designed protein of interest is relatively simple to construct synthetically or in vitro using well established recombinant DNA techniques. Therefore, DNA templates of specific amino acid sequences afforded by the method presented herein, with or without add-on reporter or affinity tag sequences, can be constructed as templates for designed recombinant protein expression.

Strategies for recombinant protein expression are well known in the art, and typically involve transfecting cells with a DNA vector that contains a genetic template of interests and then culturing the cells so that they transcribe and translate the designed protein. Typically, the cells are then lysed to extract the expressed protein for subsequent purification. Both prokaryotic and eukaryotic in vivo protein expression systems are widely used. The selection of the system depends on the type of protein, the requirements for functional activity and the desired yield.

Bacterial expression systems are most widely used for producing proteins since bacteria are easy to culture, grow quickly and produce high yields of a designed recombinant protein. However, multi-domain eukaryotic proteins expressed in bacteria often are non-functional because the cells are not equipped to accomplish the required post-translational modifications or molecular folding.

According to some embodiments of the present invention, the method presented herein is suitable for providing variant protein sequences that are characterized by increased expression in recombinant bacterial expression systems. As known in the art, recombinant bacterial expression systems are the most desired for protein production due to their high yield and low cost.

Mammalian in vivo expression systems usually produce functional protein with some notable limitations. Cell-free protein expression is the in vitro synthesis of protein using translation-compatible extracts of whole cells. In principle, whole cell extracts contain all the macromolecules components needed for transcription, translation and even post-translational modification. These components include RNA polymerase, regulatory protein factors, transcription factors, ribosomes, and tRNA. When supplemented with cofactors, nucleotides and the specific gene template, these extracts can synthesize proteins of interest in relative ease.

Although typically not sustainable for large scale production, cell-free protein expression systems have several advantages over traditional in vivo systems. Cell-free systems enable protein labeling with modified amino acids, as well as expression of designed proteins that undergo rapid proteolytic degradation by intracellular proteases. Also, with the cell-free method, it is simpler to express many different proteins simultaneously (e.g, testing designed protein by expression on a small scale from many different recombinant DNA templates).

In some embodiments of the present invention, the structural fold of the designed protein is that of an antibody. Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

In some embodiments of the present invention, the common structural fold of the designed protein is that of a fragment of an antibody. Antibody fragments according to some embodiments of the invention can be prepared by proteolytic hydrolysis of the antibody or by expression in E. coli or mammalian cells (e.g., Chinese hamster ovary cell culture or other protein expression systems) of DNA encoding the fragment. Antibody fragments can be obtained using a proteolytic enzyme, such as pepsin or papain, for digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Nucleic acid construct corresponding to the designed protein, according to some embodiments of the invention, can be utilized to transform mammalian cells.

As described hereinabove, the polynucleotide of some embodiments of the invention can be used, preferably cloned into the nucleic acid construct of some embodiments of the invention, for genetically directing the production of a designed protein, according to some embodiments of the invention, in the transformed host cell of some embodiments of the invention.

The polynucleotide of some embodiments of the invention can be introduced into cells by any one of a variety of known methods within the art. Such methods can be found generally described in Sambrook et al., [Molecular Cloning: A Laboratory Manual, Cold Springs Harbor Laboratory, New York (1989, 1992)]; Ausubel et al., [Current Protocols in Molecular Biology, John Wiley and Sons, Baltimore, Md. (1989)]; Chang et al., [Somatic Gene Therapy, CRC Press, Ann Arbor, Mich. (1995)]; Vega et al., [Gene Targeting, CRC Press, Ann Arbor Mich. (1995)]; Vectors [A Survey of Molecular Cloning Vectors and Their Uses, Butterworths, Boston Mass. (1988)] and Gilboa et al. [Biotechniques 4 (6): 504-512 (1986)] and include, for example, stable or transient transfection, lipofection, electroporation and infection with recombinant viral vectors. For example, see U.S. Pat. No. 4,866,042 for vectors involving the central nervous system and also U.S. Pat. Nos. 5,464,764 and 5,487,992 for positive-negative selection methods for inducing homologous recombination.

An advantageous approach for introducing a polynucleotide of some embodiments of the invention into cells is by using a viral vector. Viral vectors offer several advantages including higher efficiency of transformation, and targeting to, and propagation in, specific cell types. Viral vectors can also be modified with specific receptors or ligands to alter target specificity through specific cell receptors, such as neuronal cell receptors (for example, refer to Kaspar BK. et al., 2002. Mol Ther. 5:50-6).

Retroviral vectors represent one class of vectors suitable for use with some embodiments of the invention. Defective retroviruses are routinely used in transfer of genes into mammalian cells [for review see Miller, A. D., Blood 76: 271 (1990)]. A recombinant retrovirus including a polynucleotide encoding a designed protein, according to some embodiments of the invention, can be constructed using well known molecular techniques. Portions of the retroviral genome can be removed to render the retrovirus replication defective and the replication defective retrovirus can then packaged into virions, which can be used to infect target cells through the use of a helper virus and while employing standard techniques. Protocols for producing recombinant retroviruses and for infecting cells in-vitro or in-vivo with such viruses can be found in, for example, Ausubel et al., [eds, Current Protocols in Molecular Biology, Greene Publishing Associates, (1989)]. Retroviruses have been used to introduce a variety of genes into many different cell types, including neuronal cells, epithelial cells endothelial cells, lymphocytes, myoblasts, hepatocytes and bone marrow cells.

Another suitable expression vector may be an adenovirus vector. The adenovirus is an extensively studied and routinely used gene transfer vector. Key advantages of an adenovirus vector include relatively high transduction efficiency of dividing and quiescent cells, natural tropism to a wide range of epithelial tissues and easy production of high titers [Russel, W. C. [J. Gen. Virol. 81: 57-63 (2000)]. The adenovirus DNA is transported to the nucleus, but does not integrate thereinto. Thus the risk of mutagenesis with adenoviral vectors is minimized, while short term expression is particularly suitable for treating cancer cells. Adenoviral vectors used in experimental cancer treatments are described by Seth et al. [Adenoviral vectors for cancer gene therapy. In: P. Seth (ed.) Adenoviruses: Basic biology to Gene Therapy, Landes, Austin, Tex., (1999) pp. 103-120].

A suitable viral expression vector may also be a chimeric adenovirus/retrovirus vector which combines retroviral and adenoviral components. Such vectors may be more efficient than traditional expression vectors for transducing tumor cells [Pan et al., Cancer Letters 184: 179-188 (2002)].

A specific example of a suitable viral vector for introducing and expressing the polynucleotide sequence of some embodiments of the invention in an individual is the adenovirus-derived vector Ad-TK. This vector expresses a herpes virus thymidine kinase (TK) gene for either positive or negative selection and includes an expression cassette for desired recombinant sequences. This vector can be used to infect cells that have an adenovirus receptor which includes most cancers of epithelial origin (Sandmair et al., 2000. Hum Gene Ther. 11:2197-2205).

Features that limit expression to particular cell types can also be included. Such features include, for example, promoter and regulatory elements that are specific for the desired cell type. Secretion signals generally contain a short sequence (7-20 residues) of hydrophobic amino acids. Secretion signals are widely available and are well known in the art, refer, for example to von Heijne [J. Mol. Biol. 184:99-105 (1985)] and Lej et al., [J. Bacteriol. 169: 4379 (1987)].

The recombinant vector can be administered in several ways. If viral vectors are used the procedure can take advantage of their target specificity and consequently, such vectors do not have to be administered locally. However, local administration can provide a quicker and more effective treatment. Administration of viral vectors can also be performed by, for example, intravenous or subcutaneous injection into a subject. Following injection, the viral vectors will circulate until they recognize host cells with appropriate target specificity for infection.

Nucleic acid construct corresponding to the designed protein, according to some embodiments of the invention, can be utilized to transform plant cells. The term "plant" as used herein encompasses whole plants, a grafted plant, ancestors and progeny of the plants and plant parts, including seeds, shoots, stems, roots (including tubers), rootstock, scion, and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantee, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium rectum*, *Echinochloa pyramidalis*, *Ehraffia* spp., *Eleusine coracana*, *Eragrestis* spp., *Erythrina* spp., *Eucalypfus* spp., *Euclea schimperi*, *Eulalia vi/losa*, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffus*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesli*, *Lotus* spp., *Macrotyloma axillare*, *Malus* spp., *Manihot esculenta*, *Medicago saliva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativam*, *Podocarpus totara*, *Pogonarthria fleckii*, *Pogonaffhria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys vefficillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, trees. Alternatively algae and other non-Viridiplantae can be used for the methods of some embodiments of the invention.

Constructs useful in the method of producing the designed protein in a plant, according to some embodiments of the invention, may be constructed using recombinant DNA technology well known to persons skilled in the art. The gene constructs may be inserted into vectors, which may be commercially available, suitable for transforming into plants and suitable for expression of the gene of interest in the transformed cells. The genetic construct can be an expression vector wherein said nucleic acid sequence is operably linked to one or more regulatory sequences allowing expression in the plant cells.

In a particular embodiment of some embodiments of the invention the regulatory sequence is a plant-expressible promoter.

As used herein the phrase "plant-expressible" refers to a promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ.

Nucleic acid sequences of the modified polypeptide chain, according to some embodiments of the invention, may be optimized for any expression system, including plant expression. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N [(Xn−Yn)/Yn]2/N, where Xn refers to the frequency of usage of codon n in highly expressed plant genes, where Yn to the frequency of usage of codon n in the gene of interest and N refers to the total number of codons in the gene of interest. A table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization tables such as those provided on-line at the Codon Usage Database through the NIAS (National Institute of Agrobiologic al Sciences) DNA bank in Japan (http://www(dot) kazusa(dot)or(dot)jp/codon/). The Codon Usage Database contains codon usage tables for a number of different species, with each codon usage table having been statistically determined based on the data present in Genbank.

Plant cells may be transformed stabley or transiently with the nucleic acid constructs of some embodiments of the invention. In stable transformation, the nucleic acid molecule of some embodiments of the invention is integrated into the plant genome and as such it represents a stable and inherited trait. In transient transformation, the nucleic acid molecule is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledenous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Although stable transformation is presently preferred, transient transformation of leaf cells, meristematic cells or the whole plant is also envisaged by some embodiments of the invention.

Transient transformation can be effected by any of the direct DNA transfer methods described above or by viral infection using modified plant viruses. Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667

(BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of some embodiments of the invention is demonstrated by the above references as well as in U.S. Pat. No. 5,316,931.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

In addition to the above, the nucleic acid molecule of some embodiments of the invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Uses of the Designed Protein:

The designed proteins, produced by the method presented herein, according to some embodiments of the invention, can be used, without limitation, for:

Increasing the protein yields at any recombinant protein expression system;

Enabling various recombinant protein heterologous expression systems to produce designed proteins, which otherwise would not express the corresponding wild type protein or express it poorly;

Providing proteins with improved industrial- and research-related properties, such as thermally stable enzymes and binding proteins and the like;

Enabling expression of proteins in research or industry that typically can only be expressed with solubility tags, such as MBP tag;

Improving the serum-half-life of antibodies, binding proteins, enzymes and other proteins used for diagnostic, therapeutic and other purposes in vivo;

Increasing the yield of properly folded active antibodies, binding proteins, enzymes and other proteins, thereby reducing the amount of administered protein in diagnostic, therapeutic and other purposes in vivo; and Improving the affinity or activity of the target protein for its substrate.

It is expected that during the life of a patent maturing from this application many relevant methods for designing de novo stabilized proteins based on sequence and structural information found in naturally occurring proteins will be developed, and the scope of the phrase "a method of computationally designing a modified polypeptide chain starting from an original polypeptide chain" is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Benchmark 1—Method Parameterization

The method presented herein was tested for prediction accuracy against experimentally validated data, and parameterized several computational expressions including the minimal acceptance threshold, the weight of the PSSM energy term and the coordinate constraint weight.

For this purpose a dataset of 23 "back to consensus" mutations in triosephosphate isomerase (TIM) from *Saccharomyces cerevisiae* were tested, based on a recently published study [Sullivan, B. J. et al., *J Mol Biol*, 2012, 420(4-5):384-99, which is referred to herein as "the 2012 study" and is incorporated herein by reference]. In the 2012 study there were 240 aligned positions in the TIM family, out of which 43% of the positions deviate between *S. cerevisiae* TIM and the consensus sequence. Of these 103 positions, 23 individual consensus mutations that vary in solvent exposure, secondary structure, conservation, and evolutionary substitution frequency were chosen for expression to further understand the consensus mutation phenomenon and its role in stabilization in the 2012 study.

Dividing the 23 mutations of the 2012 study into three groups, there were 11 stabilizing mutations (7 increased the protein Tm by more than 1° C.), 5 were neutral or slightly destabilizing mutations (a change of less than ±0.5° C. in Tm) and 7 were very destabilizing (4 of which were deleterious and resulted in nullified expression).

In order to compare the prediction power thereof to the experimental results of the 2012 study, the method presented herein, according to some embodiments of the present invention, was implemented in all steps except the combinatorial design step, and the results compared the single position energy values (position-specific stability scoring) to the experimentally measured Tm found in the 2012 study.

Figure 3:
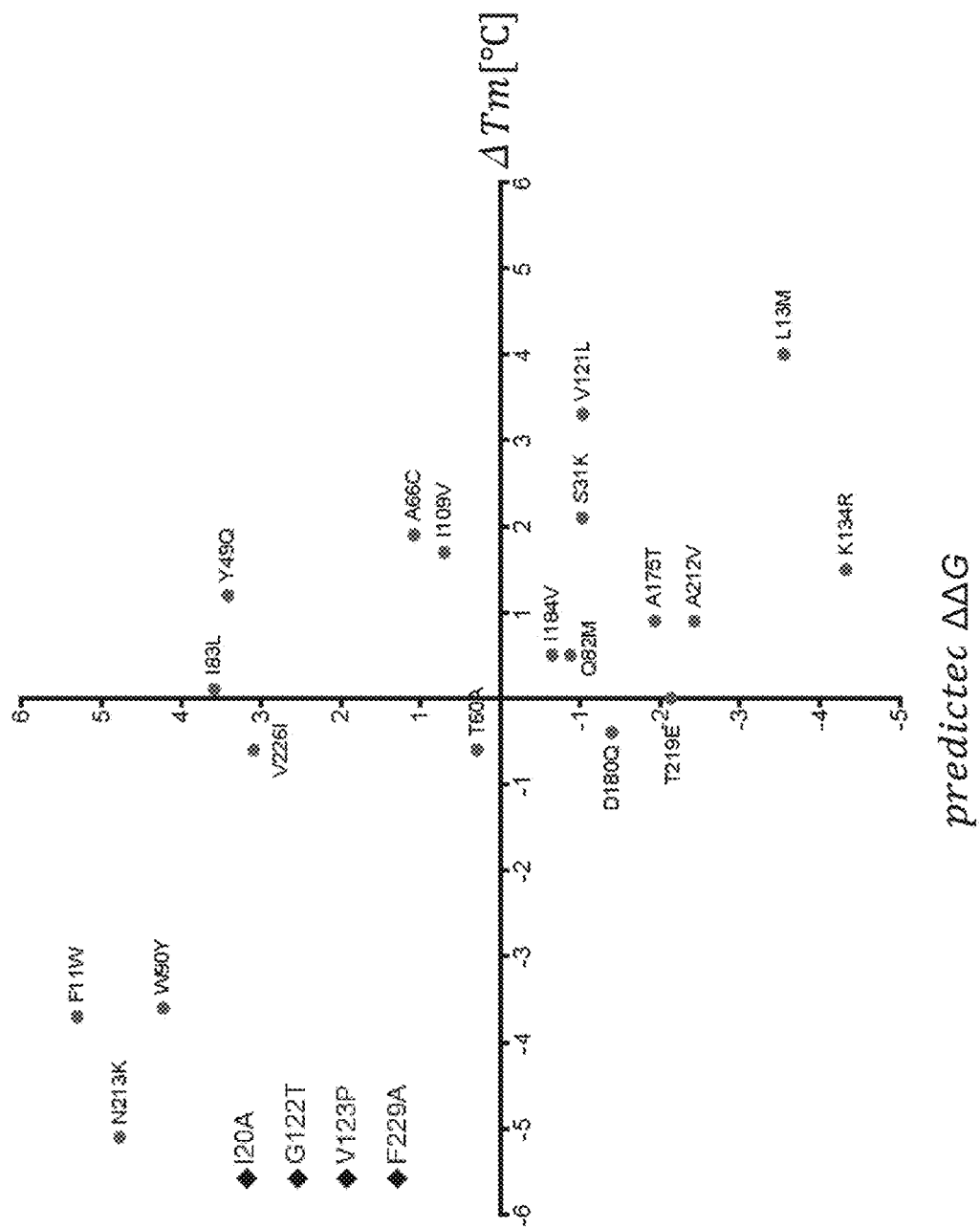
FIG. 3 is a graphical representation of a comparison between the predictions afforded by using the method presented herein (y-axis), and the experimentally measured Tm values obtained in the 2012 study (x-axis), wherein the x-axis represents the change in Tm ($\Delta$Tm), and the y-axis represents the predictions afforded by the method presented herein in Rosetta energy units
Figure 4:
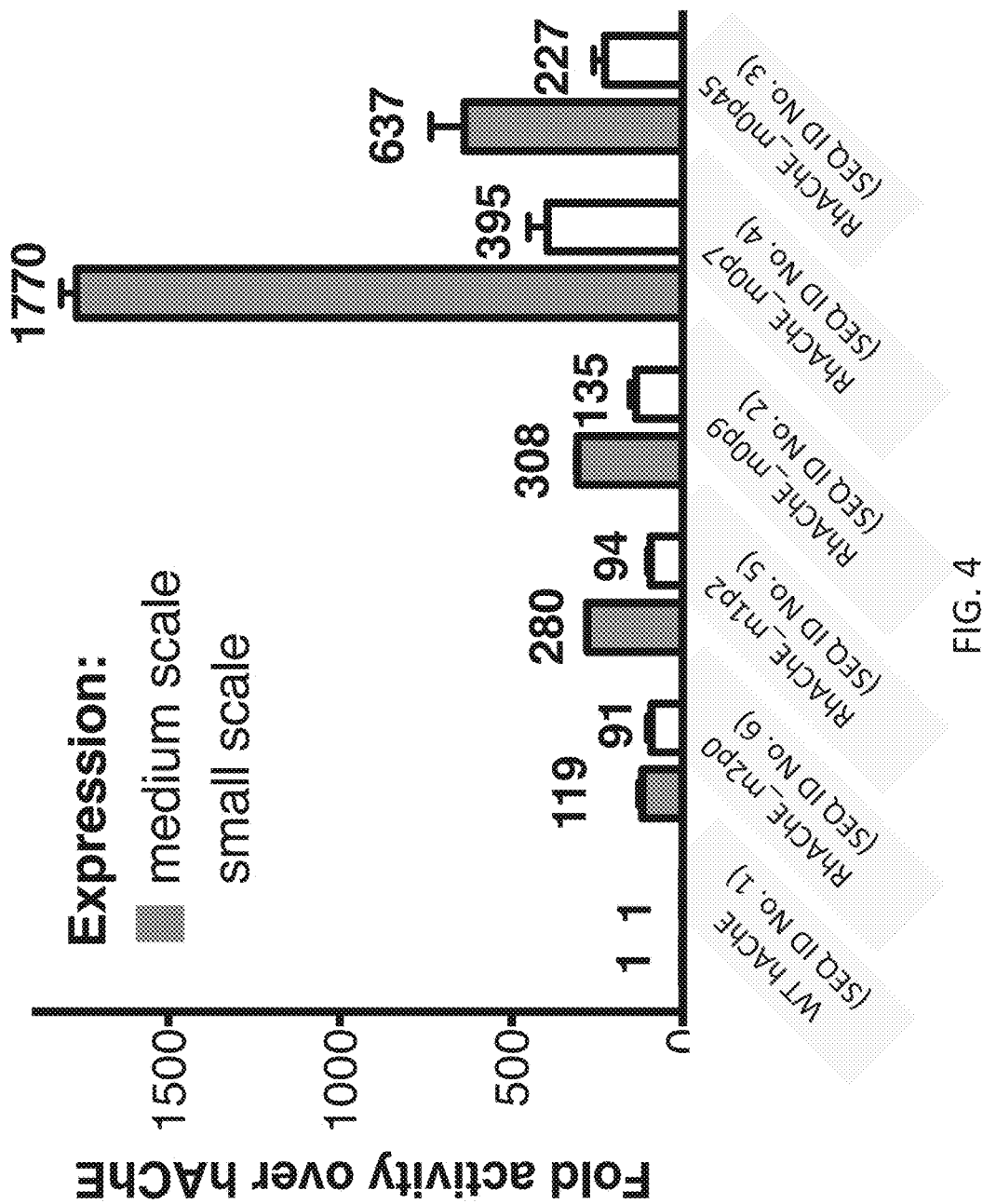
FIG. 4 presents a bar plot showing the activity levels of five exemplary AChE stabilized variants, normalized to the activity of WT hAChE, as measured in crude bacterial lysates that were derived from 250 ml flasks ("medium scale") or 0.5 ml E. coli cultures grown in a 96-well plate ("small scale"), and showing a higher activity levels in all exemplary designed variants that reflect higher levels of soluble, functional enzyme compared to the wild-type.

FIG. 3 is a graphical representation of a comparison between the position-specific stability scoring obtained by the method presented herein (y-axis), and the experimentally measured Tm values obtained in the 2012 study (x-axis), wherein an increase in Tm ($\Delta$Tm) reflects an introduction of a stabilizing mutation, and negative energy ($\Delta$E) values reflect method-identified substitutions that are predicted to be stabilizing.

As can be seen in FIG. 3, four mutations resulted in non-detectable expression (deleterious mutations) and therefore their $\Delta$Tm could not be measured (listed on the upper-left quarter of FIG. 3, and marked by black diamonds to reflect the fact that the method correctly predicted all four mutations to be extremely destabilizing). The lower left quadrant represents false-positive predictions. It is noted that the lower-left quadrant is essentially empty of any significantly destabilizing mutation. D180Q is the only destabilizing mutation that was erroneously predicted to be stabilizing and it is only slightly destabilizing with a $\Delta$Tm of −0.4° C. Two mutations (T219E and I83L) fall between $\Delta$Tm values of −0.3° C. to +0.3° C. and are regarded as experimental error ("noise").

As can further be seen in FIG. 3, the method correctly predicted all 7 very destabilizing mutations, which means that the method practically exhibited zero false positives in this benchmark. Out of the 11 stabilizing mutations, 8 were correctly predicted. This means that the low false positive rate does not stem from an inherent tendency of the method to prefer the WT identity but rather it reflects accurately the experimental results. Least accurate was the prediction of mutations with values around zero, reflecting neutral or close to neutral mutations.

These trends were similar for method uses under different coordinate constraint weights and PSSM weights, however the best correlation was achieved for a coordinate constraint weight of 0.4 and a PSSM energy term weight of 0.4 and they were selected for general use of the method with other proteins. It is noted that these weights, which were calibrated within the Rosetta software suite for biomolecular modeling and design, are non-limiting examples and other terms, determined otherwise, are contemplated within the scope of the present invention.

Example 2

Benchmark 2—Method Validation

Following the parameterization of the method presented hereinabove, the predictive ability of the method was tested on another case for which experimental data are available. This benchmark test was conducted to further evaluate the predictions reliability and the parameters adequacy to ensure that no overfitting was introduced inadvertently.

For this purpose, a dataset of experimentally tested mutations in fungal endoglucanase 5 (PDB ID 3QR3) [Trudeau, D. L. et al., *Biotechnol Bioeng*, 2014, 111(12), pp. 2390-7; incorporated herein by reference and referred to herein as "the 2014 study"] were used as a benchmark that is unrelated to the 2012 study discussed hereinabove. In the 2014 study only a final variant with 16 mutations is discussed. For this benchmark the raw data of the 2014 study were used, including all experimentally tested mutations. The 2014 study used a variety of sequence and modeling based stabilization approaches to predict mutations that would improve stability and protein yields. Among these mutations was a subset of mutations predicted by "back to consensus" analysis, a subset predicted by FoldX [Schymkowitz, J. et al., *Nucleic Acids Res*, 2005, 33:W382-8], a subset of mutations to proline, and other.

The 2014 study tested each mutation experimentally according to the following steps:

a) Mutants were cloned into yeast in a secretion vector;

b) In an initial screen the enzyme hydrolysis activity was tested in supernatant at 73° C.;

c) Mutants showing activity lower than WT were abandoned, while mutants showing WT level activity or higher were expressed and purified in a bacterial system; and d) The latter mutants were tested for thermal stability using inactivation assays: samples were incubated in a range of temperatures for 10 minutes, then cooled to 60° C. (the optimal temperature for this enzyme and the substrate used) and then tested for activity for 2 hours. For each of these mutants the 2014 study reports a temperature value representing the delta in the temperature of 50% residual activity compared to the WT enzyme ($\Delta T_{50}$).

Out of 275 predicted mutations of the 2014 study, only 34 were found to be experimentally stabilizing (a mutation is defined as stabilizing if it results in a $\Delta T_{50}$ above 0.3° C.). 231 mutations were found to be experimentally destabilizing (under this category are all mutations that resulted in a $\Delta T_{50}$ below −0.3° C. and mutations that did not pass the initial screening. The latter group probably includes destabilizing mutations as well as mutations that disrupt the enzymes function. 10 mutations were defined as being close to neutral (measured $\Delta T_{50}$ values were between −0.3° C. and 0.3° C.) and were excluded from further analysis.

The method presented herein was implemented for the fungal endoglucanase 5 (PDB ID 3QR3) using the aforementioned weights and steps, and the position-specific stability scoring results from the single position scanning step, expressed in r.e.u, were compared to the experimental data and presented in Table 1 below. The computational position-specific stability scoring was used to predict the effects of each mutation on free energy ($\Delta\Delta G_{calc}$). Amino acid substitutions were predicted to be stabilizing if they showed $\Delta\Delta G_{calc} < -0.45$ r.e.u., and destabilizing otherwise.

TABLE I

| Substitutions | Stabilize | Destabilize | Total |
|---|---|---|---|
| True prediction | 12 (35%) | 230 (99.6%) | 242 |
| False prediction | 22 (65%) | 1 (0.4%) | 23 |
| Total | 34 | 231 | 265 |

As can be seen in Table 1, the method presented herein correctly classified nearly all destabilizing amino acid substitutions (99.6%) and 35% of the stabilizing mutations with p-value smaller than $10^{-4}$ according to two-tailed Fischer's exact test.

In this benchmark experiment the method was implemented using a minimal acceptance threshold of $-0.45$ r.e.u; however, if an overly-permissive acceptance threshold of zero were used, the method would have correctly predicted four additional stabilizing mutations (overall 47% true positives), and would have also predicted eight additional false-positives (i.e., overall 96% true negatives).

These results demonstrate the advantage of using a minimal acceptance threshold below zero despite the loss of some stabilizing substitutions (false negatives). It should be noted that the sequence space and final combinatorial variants predicted by the method for this protein, contain mutations that were not predicted in the 2014 study, and that these mutations strengthen the hypothesis that there is more than a single solution for protein stabilization.

Example 3

Design for Stabilization of hAChE

As a demonstration of the strength and generality of the method for stabilizing proteins presented herein, a challenging test case in the form of the structurally sensitive and highly studied enzyme, human acetylcholinesterase (hAChE), was chosen.

Acetycholinesterase (AChE) hydrolyses the neurotransmitter acetylcholine to terminate synaptic transmission. Its activity is essential for proper function of nerve and muscle tissues. The enzyme is a target for nerve agents that irreversibly inhibit its enzymatic activity. The enzyme is notorious for its poor stability upon heterologous expression in prokaryotic cells. Common expression systems are HEK-293 cell line and insect cell lines. Attempts to express the protein in bacterial systems yielded an extremely small soluble fraction hampering the use of the protein in research and therapeutics [Fischer, M. et al., Cell Mol Neurobiol, 1993, 13(1):25-38].

The method presented herein was implemented on human AChE (hAChE; PDB ID 4EY7) without the sub-MSA preparation to stabilize the enzyme. PSSM scores were derived from a MSA having 165 AChE homologous sequences. Residues surrounding the active site (see hereinbelow) and residues within the dimerization interface were identified as key residues, which are determined and treated as described hereinabove.

AChE's active site is located at the bottom of a deep gorge that penetrates half way (20 Å) into the enzyme, and mutations along the gorge were shown to reduce ACh-hydrolysis rates by up to 1,000-fold. To increase the stability and expression levels of hAChE without altering its activity, restrictions on the allowed sequence space of the newly designed hAChE were imposed: in all Rosetta modeling simulations, a complex structure of hAChE with the reversible inhibitor E2020 bound in the active site gorge was used and the side-chain conformations of amino acids within 8 Å E2020, which spans the full length of the active-site gorge, had to remain as in the native hAChE structure, namely identified as key residues. The single position scanning step (that included the imposed key residues described above) led to a dramatically reduced sequence space (referring here to the minimal acceptance threshold of $-0.45$ r.e.u based sequence space) available for design. The reduced sequence space led to convergence of combinatorial sequence optimization to identical, or nearly identical, sequences for any given acceptance threshold ($\Delta\Delta G_{calc}$ cutoff in r.e.u); this convergence, which is not usual in computational design, is a prerequisite for reproducibility and usage by non-experts.

Table 2 presents the sequence space of amino acid substitutions resulting from a single position scanning step imposing an acceptance threshold of $-0.45$ r.e.u, using the derived PSSM described above, and imposing the active-site constraints described above. The sequence space presents 81 amino acid substitution positions, each with at least one optional substitution over the WT amino acid at the given position.

TABLE 2

Sequence Space for hAChE

| No. | Position (numbering according to PDB ID 4EY7) | Sequence space (WT aa first from the left) | RhAChE_m0p9 (SEQ ID No. 2) | RhAChE_m0p45 (SEQ ID No. 3) | RhAChE_m0p7 (SEQ ID No. 4) | RhAChE_m1p2 (SEQ ID No. 5) | RhAChE_m2p0 (SEQ ID No. 6) |
|---|---|---|---|---|---|---|---|
| 1. | 9 | L/V/I | | I | | | |
| 2. | 11 | T/D | | | | | |
| 3. | 12 | V/T | T | T | T | T | |
| 4. | 16 | R/K | | K | | | |
| 5. | 17 | L/I/V | | I | | | |
| 6. | 23 | K/M/T | M | T | T | | |
| 7. | 25 | P/I/T | | I | | | |
| 8. | 33 | L/Y | | | | | |

TABLE 2-continued Sequence Space for hAChE

| No. | Position (numbering according to PDB ID 4EY7) | Sequence space (WT aa first from the left) | RhAChE_m0p9 (SEQ ID No. 2) | RhAChE_m0p45 (SEQ ID No. 3) | RhAChE_m0p7 (SEQ ID No. 4) | RhAChE_m1p2 (SEQ ID No. 5) | RhAChE_m2p0 (SEQ ID No. 6) |
|---|---|---|---|---|---|---|---|
| 9. | 42 | M/I/V | V | V | V | V | |
| 10. | 48 | L/R | R | R | R | R | R |
| 11. | 54 | Q/R | | R | | | |
| 12. | 60 | V/L/W | W | W | W | W | W |
| 13. | 66 | Q/P | | | | | |
| 14. | 67 | S/N | N | N | N | N | N |
| 15. | 81 | E/P | | P | | | |
| 16. | 91 | E/D/N/P | N | P | N | | |
| 17. | 109 | T/K | K | K | K | | |
| 18. | 110 | S/N | N | N | N | | |
| 19. | 112 | T/A/L/V | A | A | A | V | |
| 20. | 115 | L/M | M | M | M | M | M |
| 21. | 127 | A/S | S | S | S | S | S |
| 22. | 140 | Q/R | R | R | R | R | |
| 23. | 141 | A/E/T/V | T | E | T | | |
| 24. | 144 | T/L/V | V | V | V | V | V |
| 25. | 159 | L/F | | | | | |
| 26. | 160 | A/Y | | | | | |
| 27. | 161 | L/F | | | | | |
| 28. | 187 | V/I | I | I | I | I | I |
| 29. | 196 | S/N | | N | | | |
| 30. | 211 | M/F | | | | | |
| 31. | 226 | V/I | I | I | I | I | I |
| 32. | 234 | G/A/C | A | A | A | A | A |
| 33. | 238 | T/Y | | Y | Y | | |
| 34. | 240 | G/S/T | S | S | S | S | S |
| 35. | 241 | M/R | | R | R | | |
| 36. | 242 | G/D/E/Q | E | E | E | E | |
| 37. | 249 | T/K/L | | L | L | | |
| 38. | 253 | H/D/E/K/N/Q/R | K | K | K | K | K |
| 39. | 275 | T/N | | N | N | | |
| 40. | 278 | A/P | P | | P | P | |
| 41. | 280 | V/D/E/Q | E | E | E | | |
| 42. | 282 | V/L | | | | | |
| 43. | 306 | D/S | | S | | | |
| 44. | 309 | S/P/T | P | P | P | P | |

TABLE 2-continued

Sequence Space for hAChE

| No. | Position (numbering according to PDB ID 4EY7) | Sequence space (WT aa first from the left) | RhAChE_m0p9 (SEQ ID No. 2) | RhAChE_m0p45 (SEQ ID No. 3) | RhAChE_m0p7 (SEQ ID No. 4) | RhAChE_m1p2 (SEQ ID No. 5) | RhAChE_m2p0 (SEQ ID No. 6) |
|---|---|---|---|---|---|---|---|
| 45. | 318 | A/K/N/T | N | N | N | N | |
| 46. | 322 | H/K | K | K | K | K | |
| 47. | 325 |

TABLE 2-continued

Sequence Space for hAChE

| No. | Position (numbering according to PDB ID 4EY7) | Sequence space (WT aa first from the left) | RhAChE_m0p9 (SEQ ID No. 2) | RhAChE_m0p45 (SEQ ID No. 3) | RhAChE_m0p7 (SEQ ID No. 4) | RhAChE_m1p2 (SEQ ID No. 5) | RhAChE_m2p0 (SEQ ID No. 6) |
|---|---|---|---|---|---|---|---|
| 80. | 528 | A/H | | H | | H | |
| 81. | 542 | A/M | | M | | | |

As can be reckoned from Table 2, the method produced a wide yet manageable sequence space of amino acid substitutions from which a large number of designed sequences can be selected to produce a stabilized hAChE protein variants. Five final combinatorial steps of the method, each based on a different acceptance threshold (see hereinbelow) led to five variants, each based on a different acceptance threshold. The acceptance thresholds from the most permissive to the strictest were −0.45 r.e.u, −0.7 r.e.u, −0.9 r.e.u, −1.2 r.e.u and -2.0 r.e.u. Combinatorial design under these acceptance thresholds yielded design variants with 67, 51, 43, 30 and 17 amino acid substitutions, respectively.

It is noted herein that embodiments of the present invention encompass any and all the possible combinations of amino acid alternatives presented in Table 2 (all possible variants stemming from the sequence space presented herein).

The designed AChE mutations are scattered throughout the enzyme, and show typical characteristics of stabilizing amino acid substitutions, including improved core packing, higher backbone rigidity, increased surface polarity, more hydrogen bonds and salt bridges and improved secondary structure propensity. All five exemplary designed AChE variants, RhAChE_m0p9 (SEQ ID No. 2), RhAChE_m0p45 (SEQ ID No. 3), RhAChE_m0p7 (SEQ ID No. 4), RhAChE_m1p2 (SEQ ID No. 5) and RhAChE_m2p0 (SEQ ID No. 6), exhibited improved structural stability manifested in significantly higher bacterial expression levels and in higher thermal stability. The designed protein obtained under the acceptance threshold −0.7 r.e.u, referred to herein as "RhAChE_m0p7" (SEQ ID No. 4), exhibited the highest bacterial expression levels compared to WT hAChE (SEQ ID No. 1). RhAChE_m0p7 (SEQ ID No. 4) exhibited about 1800-fold higher bacterial expression level in medium scale, and about 400-fold higher bacterial expression level in small scale, compared to comparable bacterial expression of WT hAChE (SEQ ID No. 1).

WT hAChE (SEQ ID No. 1), RhAChE_m0p9 (SEQ ID No. 2), RhAChE_m0p45 (SEQ ID No. 3), RhAChE_m0p7 (SEQ ID No. 4), RhAChE_m1p2 (SEQ ID No. 5) and RhAChE_m2p0 (SEQ ID No. 6), were expressed in E. coli SHuffle T7 Express cells as Trx-AChE fusion at their N-terminus. The E. coli SHuffle T7 Express cells enhance formation of disulfide bonds necessary for proper formation of the folded structure. Clarified cell lysates were tested for hydrolytic activity of acetylthiocholine to acetate and thiocholine. Thiocholine cleaves 5,5'-dithiobis-(2-nitrobenzoic acid) (Ellman's reagent or DTNB) to give 2-nitro-5-thiobenzoate (TNB$^-$), which ionizes to the yellow TNB$^{2-}$ dianion in water at neutral and alkaline pH, allowing simple quantification of hydrolysis activity by measurement of the solution absorbance at 412 nm (i.e., the Ellman's Assay). For the inactivation temperature determination, samples were incubated at increasing temperatures for 30 minutes, then cooled at 4° C. for 10 minutes, and then assayed for activity (AChE hydrolysis) at room temperature.

Table 3 summarizes the experimental comparison between WT hAChE (SEQ ID No. 1) and the five AChE stabilized exemplary variants. Column 3 of Table 3 presents the activity levels as measured in crude lysates of cells expressing the stabilized AChE variants from 250 ml E. coli cultures, normalized against the activity levels of WT hAChE (SEQ ID No. 1) expressed in the same bacterial cells. Since AChE is a diffusion-limit enzyme, increased activity of the stabilized variants is directly proportional to an increase in soluble bacterial expression levels. The results are based on average initial rate of acetylthiocholine hydrolysis ($V_0$) of each protein, whereas higher activity is associated with an equivalent increase in the fraction of soluble and well-folded protein, which infer stability.

Columns 4 and 5 of Table 3 present the thermal stabilities of WT hAChE (SEQ ID No. 1) and of the five stabilized AChE variants, as manifested in heat inactivation assays, where Column 4 of Table 3 presents values measured in crude lysates, and Column 5 of Table 3 presents values as measured for purified fractions. The enzyme samples were incubated at varying temperatures, cooled down, and tested for AChE activity, and inactivation temperature is the temperature at which 50% of activity is retained/lost. It should be noted that WT hAChE (SEQ ID No. 1) is extremely hard to purify from bacterial lysates due to its very low expression levels and therefore, the value reported for the purified WT hAChE (SEQ ID No. 1) is based on expression in mammalian HEK293 cells.

Column 6 of Table 3 presents the inactivation-rate constants by the nerve agent VX that are nearly identical between the WT hAChE (SEQ ID No. 1) and the stabilized variants, and Columns 7-9 of Table 3 present the hydrolysis rates of ACh by WT hAChE (SEQ ID No. 1) and by the stabilized variants.

TABLE 3

| AChE variant | No. of aa substitutions | Normalized activity | Inactivation temp. (° C.) | | $k_i$ ($S_P$-VX) × $10^7$ ($M^{-1}min^{-1}$) | $K_M$ (mM) | $k_{cat}$ × $10^5$ ($min^{-1}$) | $k_{cat}/K_M$ × $10^9$ ($M^{-1}min^{-1}$) |
|---|---|---|---|---|---|---|---|---|
| | | | Lysate | Purified | | | | |
| WT hAChE (SEQ ID No. 1) (HEK293) | — | — | — | 50 ± 0.3 | 7.92 ± 0.15 | 0.087 ± 0.01 | 3.8 ± 0.2 | 4.37 ± 0.6 |

TABLE 3-continued

| AChE variant | No. of aa substitutions | Normalized activity | Inactivation temp. (° C.) Lysate | Inactivation temp. (° C.) Purified | $k_i$ ($S_P$-VX) × $10^7$ ($M^{-1}min^{-1}$) | ACh hydrolysis $K_M$ (mM) | ACh hydrolysis $k_{cat}$ × $10^5$ ($min^{-1}$) | ACh hydrolysis $k_{cat}/K_M$ × $10^9$ ($M^{-1}min^{-1}$) |
|---|---|---|---|---|---|---|---|---|
| WT hAChE (SEQ ID No. 1) (bacterial) | — | 1 | 44 ± 0.3 | ND | ND | ND | ND | ND |
| RhAChE_m2p0 (SEQ ID No. 6) | 17 | 119 ± 20 | 60 ± 0.4 | ND | 6.48 ± 0.71 | 0.050 ± 0.006 | 4.36 ± 0.1 | 8.72 ± 1.1 |
| RhAChE_m1p2 (SEQ ID No. 5) | 30 | 280 ± 40 | 61 ± 0.2 | 67 ± 0.3 | ND | ND | ND | ND |
| RhAChE_m0p9 (SEQ ID No. 2) | 42 | 308 ± 44 | 62 ± 0.3 | 69 ± 0.3 | 2.65 ± 0.52 | 0.177 ± 0.01 | 4.35 ± 0.1 | 2.46 ± 0.2 |
| RhAChE_m0p7 (SEQ ID No. 4) | 51 | 1770 ± 258 | 62 ± 0.2 | 66 ± 1.2 | 7.60 ± 0.34 | 0.071 ± 0.007 | 2.73 ± 0.07 | 3.85 ± 0.4 |
| RhAChE_m0p45 (SEQ ID No. 3) | 67 | 637 ± 134 | 61 ± 0.2 | 69 ± 0.6 | 6.47 ± 0.82 | 0.104 ± 0.01 | 3.16 ± 0.01 | 3.04 ± 0.3 |

As can be seen in Table 3, all five exemplary stabilized AChE variants exhibit higher bacterial expression levels, ranging from about 100-fold to about 1800-fold higher levels compared to the expression level of WT hAChE (SEQ ID No. 1). As can further be seen in Table 3, all five exemplary stabilized AChE variants show significantly higher thermal stability, i.e., the temperature at which 50% of the protein activity is retained/lost, ranging from about 16° C. to 19° C. higher heat inactivation temperature compared to the wild-type in both lysates and in purified samples. As can be seen in Table 3, all exemplary variants hydrolyze Ach at rates that are within a 2-fold margin relative to WT hAChE (SEQ ID No. 1), excluding RhAChE_m1p2 (SEQ ID No. 5) for which the rates were not determined (ND) due to technical reasons, indicating that the catalytic gorge of AChE stabilized variants is practically identical to the WT hAChE (SEQ ID No. 1), as desired, despite multiple mutations introduced thereto (17-67 mutations).

FIG. 4 is a bar plot representation of values reported in Column 3 of in Table 3, showing activity levels of the five exemplary AChE stabilized variants, normalized to the activity of WT hAChE (SEQ ID No. 1) as measured in crude bacterial lysate. Crude lysates were derived from 250 ml flasks ("medium scale" in FIG. 4) or 0.5 ml *E. coli* cultures grown in a 96-well plate ("small scale" in FIG. 4). The higher activity levels in all designed variants: RhAChE_m2p0 (SEQ ID No. 6); RhAChE_m1p2 (SEQ ID No. 5) RhAChE_m0p9 (SEQ ID No. 2); RhAChE_m0p7 (SEQ ID No. 4); RhAChE_m0p45 (SEQ ID No. 3), reflect higher levels of soluble, functional enzyme compared to WT hAChE (SEQ ID No. 1).

As can be seen in FIG. 4, the variant RhAChE_m0p7 (SEQ ID No. 4) exhibited about 1800-fold higher activity than the WT hAChE (SEQ ID No. 1) expressing cells.

Another conclusion that can be made from this experiment is the finding that a variant obtained under a medium-level acceptance threshold is characterized as more stable compared to variants obtained under stricter and more permissive acceptance thresholds.

All AChE variants hydrolyzed ACh at rates that are within a 2-fold margin relative to WT hAChE (SEQ ID No. 1), and displayed inactivation-rate constants by the nerve agent VX that are nearly identical to WT hAChE (SEQ ID No. 1), with the largest deviation observed for RhAChE_m0p9 (SEQ ID No. 2), which exhibited a 2.5-fold lower inactivation rate. These observations of nearly identical activity profile of the designed and wild-type AChE suggested that the designed enzymes' active site is essentially identical to that of WT hAChE (SEQ ID No. 1). To verify this, crystallization trials were conducted using RhAChE_m0p7 (SEQ ID No. 4), variant that exhibited the highest bacterial-expression yields. Large crystals formed within a few days of the beginning of trials and more reproducibly, and RhAChE_m0p7's (SEQ ID No. 4) structure was solved at 2.6 Å resolution, thus yielding, the first structure of an AChE expressed in a prokaryote (data not shown). The structure of RhAChE_m0p7 (SEQ ID No. 4) was very similar to that of WT hAChE (SEQ ID No. 1), with a C60 root-mean-square deviation (rmsd) of 0.37 Å for 450 aligned positions (out of 528 positions). Active-site residues aligned particularly well, with an all-atom rmsd of only 0.125 Å. Thus, despite 51 mutations relative to wild type, about 2,000-fold gain in bacterial expression levels, and 20° C. higher heat tolerance, RhAChE_m0p7 (SEQ ID No. 4) is virtually indistinguishable in its active site from hAChE, and could therefore serve in future structural studies of inhibitors that target the AChE active site.

Example 4

Design for Stabilization of Phosphotriesterase (PTE)

As another demonstration of the strength and generality of the method for stabilizing proteins presented herein, another challenging test case in the form of the structurally sensitive and highly studied enzyme, phosphotriesterase (PTE) from *Pseudomonas diminuta*, was chosen.

PTE was first identified in the 1980s in bacteria isolated from sites contaminated with parathion, the first widely used organophosphate pesticide. Although these compounds were introduced to the environment only in the 1950s, the enzyme's catalytic rate approaches diffusion limit, raising intriguing questions about its pathway of rapid evolution from a natural enzyme to a parathion degrading one. The enzyme attracts significant attention since it has also been shown to catalyze the detoxification of chemical nerve agents such as sarin and VX. However, WT PTE marginal stability impeded its research until a more stable variant, PTE-S5 (SEQ ID No. 7), with three mutations was generated by directed evolution [Roodveldt, C. et al., Protein Eng Des Sel, 2005, 18(1):51-8]. PTE is a metalloenzyme having two active-site $Zn^{+2}$ ions structurally associated with the protein that are important to maintain the enzyme in the functional conformation. While the recombinant expression levels of PTE-S5 (SEQ ID No. 7) have increased compared to the recombinant expression levels of the WT, the resulting protein exhibited a significant decrease in metal affinity—a major practical drawback for applications in conditions in which $Zn^{+2}$ cannot be supplemented. Moreover, introduction of function-altering mutations destabilized the enzyme, as is often the case for laboratory-evolved enzymes [Tokuriki, N. et al., *PLoS Comput. Biol.*, 2008, 4, 35-37] hampering any further engineering of the protein.

In this example, wild-type PTE (PDB ID 1HZY), was subjected to the method presented herein. The BLAST analysis against a non-redundant protein database using a minimal sequence identity cutoff of 34% yielded a relatively small and redundant MSA. This was an expected result for a recently evolved enzyme that has only a few similar homologous proteins. Hence, to enrich the sequence data the identity cutoff was reduced to 28%, which significantly improved diversity yielding an MSA that was derived from qualifying 95 homologous sequences with varying diversities from one another.

Residues surrounding the catalytic active site pocket at up to 8 Å from the bound ligand, residues within 5 Å from the $Zn^{+2}$ ions, as well as residues within the homodimer interface (5 Å from chain B), were identified as key restudies and were therefore not allowed to permute or repack but were allowed minimize during the various method steps (refinement, single position scanning and combinatorial design).

Table 4 presents the sequence space of amino acid substitutions resulting from the single position scanning step using the derived PSSM, imposing the key residues described above and imposing an acceptance threshold of −0.45 r.e.u. The sequence space has 40 amino acid substitution positions, each with at least one optional substitution over the WT amino acid at the given position.

TABLE 4

Sequence Space for PTE

| No. | Position (numbering according to PDB ID 1HZY) | Sequence space (WT aa first from the left) | dPTE_m0p45 (SEQ ID No. 8) | dPTE_m1p0 (SEQ ID No. 9) | dPTE_m2p0 (SEQ ID No. 10) |
|---|---|---|---|---|---|
| 1. | 38 | N/M | | | |
| 2. | 49 | A/L | L | | |
| 3. | 54 | T/M | M | M | |
| 4. | 73 | F/W | | | |
| 5. | 77 | K/D | D | D | D |
| 6. | 80 | A/I | | | |
| 7. | 82 | K/R | | | |
| 8. | 96 | R/D | D | | |
| 9. | 99 | V/I | | | |
| 10. | 111 | S/E/Q | E | E | |
| 11. | 113 | L/I | | | |
| 12. | 116 | V/I | | | |
| 13. | 117 | S/A | A | | |
| 14. | 118 | R/E | E | E | E |
| 15. | 147 | T/I/V | | | |
| 16. | 166 | G/A | | | |
| 17. | 180 | Q/E | | | |
| 18. | 182 | L/K/R | R | R | |
| 19. | 184 | L/F | | | |
| 20. | 185 | K/R | R | R | R |
| 21. | 193 | A/E | E | | |
| 22. | 198 | V/I | | | |
| 23. | 203 | A/C/D/E/H/N | D | D | D |
| 24. | 211 | Q/E | E | | |
| 25. | 214 | A/D/E/K/Q/R | D | D | |

TABLE 4-continued

Sequence Space for PTE

| No. | Position (numbering according to PDB ID 1HZY) | Sequence space (WT aa first from the left) | dPTE_m0p45 (SEQ ID No. 8) | dPTE_m1p0 (SEQ ID No. 9) | dPTE_m2p0 (SEQ ID No. 10) |
|---|---|---|---|---|---|
| 26. | 222 | S/D/N/P | D | D | D |
| 27. | 231 | S/A | A | | |
| 28. | 238 | S/D/E | D | D | D |
| 29. | 242 | A/E | E | | |
| 30. | 269 | S/A | A | A | |
| 31. | 274 | I/L/T | L | L | |
| 32. | 293 | M/A/E/I/T/V | A | A | V |
| 33. | 294 | K/D/E | D | D | |
| 34. | 327 | F/H | H | | |
| 35. | 330 | L/E | E | | |
| 36. | 343 | Q/D/E | D | D | |
| 37. | 347 | A/D/E/T/R | D | E | |
| 38. | 348 | G/A/M/N/Q/T | T | T | T |
| 39. | 350 | T/M | M | M | |
| 40. | 352 | T/D/E | E | D | E |

The method was used to select 3 designed sequences (stabilized PTE variants) from the above sequence space. Three final combinatorial steps of the method, each based on a different acceptance threshold (see hereinbelow) led to three exemplary variants, each based on a different acceptance threshold. The acceptance thresholds from the most permissive to the strictest were −0.45 r.e.u, −1.0 r.e.u and −2.0 r.e.u. Combinatorial design under these acceptance thresholds yielded the designed variants with 28, 19 and 9 amino acid substitutions, respectively. The three designs were name coded dPTE_m0p45 (SEQ ID No. 8); dPTE_m1p0 (SEQ ID No. 9); and a dPTE_m2p0 (SEQ ID No. 10). The three exemplary PTE variants were cloned, fused to a maltose-binding protein tag, expressed in GG48 E. coli cells to maintain a high internal zinc concentration, and purified as previously described [Cherny, I. et al., ACS Chem Biol, 2013, 8(11):2394-403]. Since WT PTE is not stable and has low bacterial recombinant expression levels, the performance of the expressed variants was instead compared to those of the stable variant PTE-S5 (SEQ ID No. 7) that displays about 20-fold higher expression levels compared to wild-type PTE.

It is noted herein that embodiments of the present invention encompass any and all the possible combinations of amino acid alternatives presented in Table 4 (all possible variants stemming from the sequence space presented herein).

Table 5 presents stability and kinetic parameters of PTE variants, wherein normalized activity is the increase in activity in crude E. coli lysates in multiples of the activity of PTE-S5 (SEQ ID No. 7). "$T_{1/2}$ chelator" refers to the half time of residual activity following metal chelation using 50 μM 1,10 phenanthroline, and $K_M$ and $k_{cat}$ refer to the kinetic parameters with respect to the turnover of the organophosphate agent paraoxon. $T_{1/2}$ chelator and kinetic parameters were obtained only for dPTE_m1p0, the stabilized variant that showed the highest increase in heat inactivation temperature (assay definition and details are identical to Example 3 presented hereinabove)

TABLE 5

| Variant | No. of aa sub's vs. WT | Normalized activity | Inactivation temp. (° C.) Lysate | Inactivation temp. (° C.) Purified | $T_{1/2}$ chelator (min) | $K_M$ (mM) | $k_{cat} \times 10^5$ (min$^{-1}$) | $k_{cat}/K_M \times 10^9$ (min$^{-1}$M$^{-1}$) |
|---|---|---|---|---|---|---|---|---|
| PTE-S5 (SEQ ID No. 7) | 3 | 1 | 50.9 ± 0.7 | 52.4 ± 0.2 | 7.5 ± 0.3 | 0.101 ± 0.023 | 0.970 ± 0.076 | 0.96 ± 0.33 |
| dPTE_m0p45 (SEQ ID No. 8) | 28 | 2.3 | 47.0 ± 1.3 | ND | ND | ND | ND | ND |
| dPTE_m1p0 (SEQ ID No. 9) | 19 | 6.1 | 59.2 ± 0.7 | 62.0 ± 0.2 | 51.2 ± 5.1 | 0.060 ± 0.014 | 0.70 ± 0.05 | 1.17 ± 0.35 |
| dPTE_m2p0 (SEQ ID No. 10) | 9 | 2.0 | 54.7 ± 3.2 | ND | ND | ND | ND | ND |

As can be seen in Table 5, the PTE variants displayed increased levels of soluble, functional enzyme compared to the reference protein PTE-S5 (SEQ ID No. 7), even though the reference protein already exhibits 20-fold increased expression levels compared to WT PTE. Two of the three variants showed about 10° C. higher tolerance to heat inactivation relative to PTE-S5 (SEQ ID No. 7) with no significant change in activity with PTE's substrate paraoxon. Another noteworthy outcome of stabilization design was increased metal affinity—while directed evolution of wild-type PTE for higher expression, namely PTE-S5 (SEQ ID No. 7), led to a significant decrease in metal affinity, which is a major practical drawback for applications in conditions in which $Zn^{+2}$ cannot be supplemented, the designed variant dPTE_m1p0 (SEQ ID No. 9), which contains 19 mutations and exhibits the highest tolerance to heat inactivation, also exhibits a marked increase in metal affinity, restoring it to a value approaching that of wild-type PTE. dPTE_m1p0 (SEQ ID No. 9) showing higher stability has described above is now a promising candidate for further engineering of PTE to catalyze the degradation of nerve agents.

Comparison between the mutations in PTE-S5 (SEQ ID No. 7) and the variants generated by the method shows that out of 3 mutations in PTE-S5 (SEQ ID No. 7), one mutation, (K185R), was independently predicted to be stabilizing by the method provided herewith. K185R appears in the sequence space based on the minimal acceptance threshold of −0.45 r.e.u. (see Table 4, entry No. 20) and in all the alternative designs. The other two mutations in PTE-S5 (SEQ ID No. 7), namely D208G and R319S, do not appear in the sequence space and therefore do not appear in any of the alternative designs (stabilized variants). One explanation to this can be that PTE-S5 (SEQ ID No. 7) was developed by directed evolution experiments as a combination of three mutations. The effect of each mutation alone was not measured, and it might be that most of the stabilization effect comes from K185R and not from the other two mutations, which may be neutral or insignificant. Assuming however, that both D208G and R319S are stabilizing mutations, their positive position specific stability score (i.e. $\Delta\Delta G_{calc}>0$) given by the method presented hereinabove can be explained by the various restrictions imposed by the method such as energy penalty for introducing less favored amino acid according to the PSSM, relatively strong coordinate constraint and the like.

Example 5

Design for Stabilization of DNA Methyltransferase 3

The family of mammalian DNA methyltransferase 3 (Dnmt3) comprises three members, Dnmt3a and Dnmt3b are active methyltransferases, and Dnmt3L is a regulatory factor of Dnmt3a. Dnmt3a is indispensable for embryonic development; hence, Dnmt3a knockout animals are runts and die shortly after birth. Dnmt3L knockout mice are viable; however, males are sterile. Dnmt3a-L complex is involved in genomic imprinting. The enzyme has very low in-vitro activity, and the hypothesis is that most of the protein is misfolded, resulting in a very levels of active protein.

The present example attempts to increase the fractional occupancy of the DNA binding conformation, i.e., the active conformation, relative to competing conformations by lowering $\Delta G_{folded-misfolded}$.

The method presented herein was implemented, according to some embodiments thereof, without using context-specific sub-MSA, to stabilize the catalytic Dnmt3a domain (original protein having PDB ID 2QRV, chain A).

The PSSM scores were derived from a MSA comprising 83 Dnmt3a qualifying homologous sequences. Residues surrounding the ligand and the DNA chains, and residues in the homodimer and heterodimer (a-L) interfaces were identified as key residues and fixed.

Forty three (43) amino acid substitutions in 27 positions passed single position scanning step, imposing the minimal acceptance threshold. Inspection of the contribution of each energy term to the total energy revealed some trends. Forty percent (40%) of all amino acid substitutions had exceptionally high contributions from the Rosetta energy terms for omega angle and Ramachandran angles (the two torsion angles of the polypeptide chain). Changes in these terms were in some cases two orders of magnitude higher compared to standard values. It was hypothesized that this trend stems from the exceptionally low quality of the input structure.

The PDB structure has a relatively low resolution of 2.89 Å and a large number of poor outliers (see, full wwPDB X-ray Structure Validation Report for PDB ID 2QRV at the Protein Data Bank). Since RosettaDesign software, used for the structure refinement procedure, according to some embodiments of the present invention, works in torsion space and not in Cartesian space, it does not change bond lengths and angles. If many of these are outliers, the refinement process would not relieve these outliers and Rosetta might solve such strains by changing the dihedral omega or Ramachandran angles, yielding artificial mutations. Hence, it was suggested that all substitutions that had significant contributions (below −1 r.e.u) of the omega and Ramachandran terms, would be removed.

Seventeen (17) substitutions in 14 positions were removed from the designed sequence, setting the input to the combinatorial step on 26 mutations in 18 positions. As this starting point the final combinatorial step yielded a designed sequence having 15 substitutions; 4 substitutions were on adjacent positions on a protein loop, suggesting that this loop is a stability weak spot.

Figure 5:
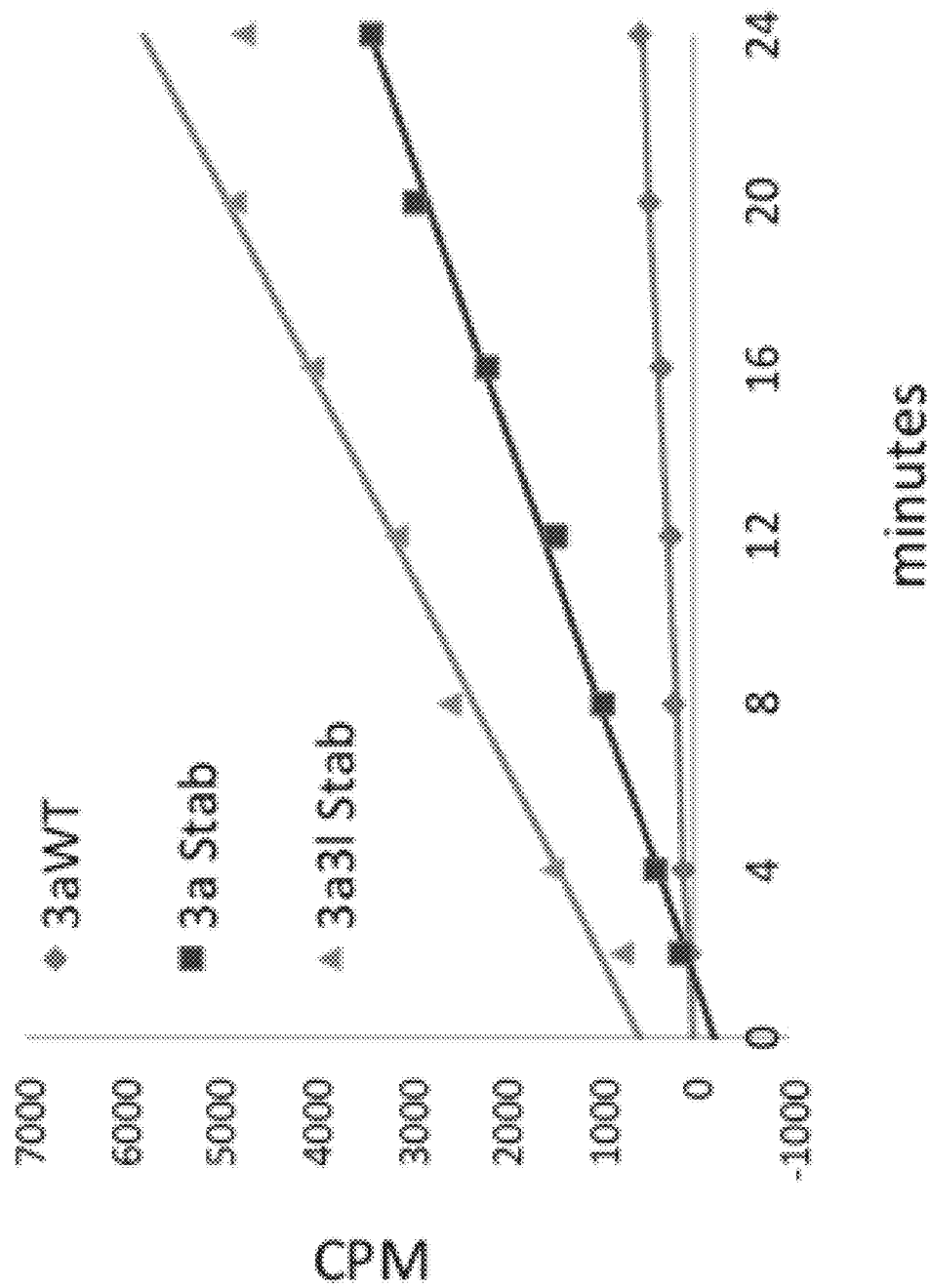
FIG. 5 presents the results of the DNA methylation activity assays conducted for the purified fractions of WT Dnmt3a (denoted "3aWT" and marked by diamonds), Dnmt3a variant (denoted "3a Stab" and marked by squares) designed using the method presented herein according to some embodiments of the invention, and designed-Dnmt3a-WT-Dnmt3L complex (denoted "3a31 Stab" and marked by triangle)

The activity of purified WT Dnmt3a, a designed Dnmt3a_Stab (SEQ ID No. 11) variant and a construct of Dnmt3a_Stab-(WT)Dnmt3L with a linker connecting the two domains, were compared and the results are presented in FIG. 5. The DNA methylation activity assay was based on methylation of a DNA substrate with a radioactive methyl group.

FIG. 5 presents the results of the DNA methylation activity assays conducted for the purified fractions of WT Dnmt3a (denoted "3aWT" and marked by diamonds), Dnmt3a variant (denoted "3a Stab" and marked by squares) designed using the method presented herein according to some embodiments of the invention, and Dnmt3a_Stab-(WT)Dnmt3L complex (denoted "3a31 Stab" and marked by triangle).

As can be seen in FIG. 5, the activity of the designed variant is about 7 fold higher than the WT Dnmt3a, indicating an increase of about 7 fold in the fraction of the folded active state. Consistent with that was the activity of Dnmt3a in complex with its regulatory unit, Dnmt3L, exhibiting higher activity compared to the activity of Dnmt3a alone. Activity was highest for the Dnmt3a_Stab-WT-Dnmt3L complex; however, there was no comparison to a (WT) Dnmt3a-(WT)Dnmt3L complex.

These results indicate an increase in the fraction of correctly folded and active enzyme, implying that the method provided herein effectively optimized the active conformation, and indeed lowers the energy term $\Delta G_{folded-misfolde}$, by providing an variant sequence designed for higher stability.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of producing a non-naturally occurring designed protein having an improved stability compared to the stability of the corresponding wild-type protein, wherein the designed protein comprises at least one modified polypeptide chain having at least six amino acid substitutions relative to an original polypeptide chain in the wild-type protein, the method comprising:

A: providing a protein expression vector suitable for use in a protein expression system, said vector comprises protein sequence data obtained by computationally designing said modified polypeptide chain starting from said original polypeptide chain, wherein said computationally designing comprises the steps of:
   (i) determining unsubstitutable positions and substitutable positions in an amino acid sequence of said original polypeptide chain;
   (ii) determining at least one position-specific amino acid alternative for each of said substitutable positions, and determining a position-specific stability scoring for each of said amino acid alternative;
   (iii) combinatorially generating a plurality of designed sequences, each of said designed sequences corresponds to a modified polypeptide chain and comprises at least six amino acid substitutions each being one of said at least one position-specific amino acid alternative, and threading each of said designed sequences on a template structure of said original polypeptide chain, to thereby generate a plurality of designed structures;
   (iv) sorting said plurality of designed structures according to a minimized energy scoring, said minimized energy scoring is determined by subjecting each of said designed structures to an energy minimization; and
   (v) selecting at least one of said plurality of designed structures, corresponding to said modified polypeptide chain, based on said minimized energy scoring,
   thereby obtaining an amino acid sequence of said modified polypeptide chain for use as sequence data input for providing said protein expression vector;

B: expressing the designed protein in said protein expression system using said protein expression vector, thereby producing the designed protein in said system, wherein said substitutions improved the stability of the designed protein relative to the corresponding wild-type protein, as determined by at least one of:
   a thermal denaturation temperature of the designed protein being equal or higher than a thermal denaturation temperature of the wild type protein;

a solubility of the designed protein being equal or higher than a solubility of the wild type protein;

a degree of misfolding of the designed protein being equal or lower than a degree of misfolding of the wild type protein;

a half-life of the designed protein being equal or longer than a half-life of the wild type protein;

a specific activity of the designed protein being equal or higher than a specific activity of the wild type protein; and a recombinant expression level of the designed protein being equal or higher than a recombinant expression level of the wild type protein.

2. The method of claim 1, wherein said original polypeptide chain comprises at least 100 amino acids.

3. The method of claim 1, wherein a selected modified polypeptide chain corresponds to designed structure having a minimal value for said minimized energy scoring.

4. The method of claim 3, wherein said energy minimization is a global energy minimization.

5. The method of claim 1, wherein said plurality of designed sequences is combinatorially generated under an acceptance threshold based on said stability scoring.

6. The method of claim 1, wherein determining said unsubstitutable positions and said substitutable positions is based on a sequence alignment of a plurality of amino acid sequences homologous to the original polypeptide chain.

7. The method of claim 6, wherein, for loop regions, said sequence alignment comprises amino acid sequences having sequence length equal to a corresponding loop in the original polypeptide chain.

8. The method of claim 6, at least one of said unsubstitutable positions is determined based on said sequence alignment.

9. The method of claim 6, wherein said sequence alignment is based on a non-redundant database of sequences.

10. The method of claim 9, wherein said plurality of amino acid sequences comprises sequences having less than 30% sequence identity with respect to said original polypeptide chain.

11. The method of claim 10, wherein said plurality of amino acid sequences is clustered using a threshold of 90-100%.

12. The method of claim 11, wherein amino acid sequences having a coverage of less than 40% and a sequence identity of less than 15% are excluded from said plurality of amino acid sequences.

13. The method of claim 12, wherein amino acid sequences having more than 5% gaps (INDELs) are excluded from said plurality of amino acid sequences.

14. The method of claim 1, wherein at least one of said unsubstitutable positions is selected from the group consisting of a highly conserved position, an active-site position, a metal binding position, a ligand binding position, a substrates binding position, a DNA/RNA binding position, a structure stabilizing position and an antigenic determinant position.

15. The method of claim 1, wherein determining said position-specific amino acid alternative is dictated by rules.

16. The method of claim 15, wherein said rules comprise a position-specific scoring matrix (PSSM).

17. The method of claim 1, wherein said position-specific stability scoring is determined based on an energy minimization.

18. The method of claim 17, wherein said energy minimization is a local energy minimization.

19. The method of claim 18, wherein said local energy minimization is effected for amino acid residues of the modified polypeptide chain having at least one atom being less than about 5 Å from at least one atom of said position-specific amino acid alternative.

20. The method of claim 1, wherein said template structure is subjected to global energy minimization prior to said threading.

21. The method of claim 20, wherein said template structure is an experimentally determined structure.

22. The method of claim 20, wherein said template structure is computationally determined based on an experimentally determined structure of a naturally occurring homolog of the original polypeptide chain.

23. The method of claim 1, wherein said energy minimization comprises at least one operation selected from the group consisting of bond length optimization, bond angle optimization, backbone dihedral angles optimization, amino acid side-chain packing optimization and rigid-body optimization of the modified polypeptide chain.

24. The method of claim 1, wherein a shortest distance of Cα of at least one of said amino acid substitutions is at least 6 Å from a water-accessible surface of the designed protein.

\* \* \* \* \*

SEQUENCE LISTING

```
<160> NUMBER OF SEQ ID NOS: 12

<210> SEQ ID NO 1
<211> LENGTH: 542
<212> TYPE: PRT
<213> ORGANISM: Homo sapiens

<400> SEQUENCE: 1

Gly Arg Glu Asp Ala Glu Leu Leu Val Thr Val Arg Gly Gly Arg Leu
1               5                   10                  15

Arg Gly Ile Arg Leu Lys Thr Pro Gly Pro Val Ser Ala Phe Leu
            20                  25                  30

Gly Ile Pro Phe Ala Glu Pro Pro Met Gly Pro Arg Arg Phe Leu Pro
            35                  40                  45

Pro Glu Pro Lys Gln Pro Trp Ser Gly Val Val Asp Ala Thr Thr Phe
        50                  55                  60

Gln Ser Val Cys Tyr Gln Tyr Val Asp Thr Leu Tyr Pro Gly Phe Glu
65                  70                  75                  80

Gly Thr Glu Met Trp Asn Pro Asn Arg Glu Leu Ser Glu Asp Cys Leu
                85                  90                  95

Tyr Leu Asn Val Trp Thr Pro Tyr Pro Arg Pro Thr Ser Pro Thr Pro
            100                 105                 110

Val Leu Val Trp Ile Tyr Gly Gly Gly Phe Tyr Ser Gly Ala Ser Ser
            115                 120                 125

Leu Asp Val Tyr Asp Gly Arg Phe Leu Val Gln Ala Glu Arg Thr Val
    130                 135                 140

Leu Val Ser Met Asn Tyr Arg Val Gly Ala Phe Gly Phe Leu Ala Leu
145                 150                 155                 160

Pro Gly Ser Arg Glu Ala Pro Gly Asn Val Gly Leu Leu Asp Gln Arg
                165                 170                 175

Leu Ala Leu Gln Trp Val Gln Glu Asn Val Ala Ala Phe Gly Gly Asp
            180                 185                 190

Pro Thr Ser Val Thr Leu Phe Gly Glu Ser Ala Gly Ala Ala Ser Val
            195                 200                 205

Gly Met His Leu Leu Ser Pro Pro Ser Arg Gly Leu Phe His Arg Ala
    210                 215                 220

Val Leu Gln Ser Gly Ala Pro Asn Gly Pro Trp Ala Thr Val Gly Met
225                 230                 235                 240

Gly Glu Ala Arg Arg Ala Thr Gln Leu Ala His Leu Val Gly Cys
                245                 250                 255

Pro Pro Gly Gly Thr Gly Gly Asn Asp Thr Glu Leu Val Ala Cys Leu
            260                 265                 270

Arg Thr Arg Pro Ala Gln Val Leu Val Asn His Glu Trp His Val Leu
        275                 280                 285
```

```
Pro Gln Glu Ser Val Phe Arg Phe Ser Phe Val Pro Val Val Asp Gly
    290                 295                 300

Asp Phe Leu Ser Asp Thr Pro Glu Ala Leu Ile Asn Ala Gly Asp Phe
305                 310                 315                 320

His Gly Leu Gln Val Leu Val Gly Val Val Lys Asp Glu Gly Ser Tyr
                325                 330                 335

Phe Leu Val Tyr Gly Ala Pro Gly Phe Ser Lys Asp Asn Glu Ser Leu
            340                 345                 350

Ile Ser Arg Ala Glu Phe Leu Ala Gly Val Arg Val Gly Val Pro Gln
        355                 360                 365

Val Ser Asp Leu Ala Ala Glu Ala Val Val Leu His Tyr Thr Asp Trp
370                 375                 380

Leu His Pro Glu Asp Pro Ala Arg Leu Arg Glu Ala Leu Ser Asp Val
385                 390                 395                 400

Val Gly Asp His Asn Val Val Cys Pro Val Ala Gln Leu Ala Gly Arg
                405                 410                 415

Leu Ala Ala Gln Gly Ala Arg Val Tyr Ala Tyr Val Phe Glu His Arg
            420                 425                 430

Ala Ser Thr Leu Ser Trp Pro Leu Trp Met Gly Val Pro His Gly Tyr
        435                 440                 445

Glu Ile Glu Phe Ile Phe Gly Ile Pro Leu Asp Pro Ser Arg Asn Tyr
450                 455                 460

Thr Ala Glu Glu Lys Ile Phe Ala Gln Arg Leu Met Arg Tyr Trp Ala
465                 470                 475                 480

Asn Phe Ala Arg Thr Gly Asp Pro Asn Glu Pro Arg Asp Pro Lys Ala
                485                 490                 495

Pro Gln Trp Pro Pro Tyr Thr Ala Gly Ala Gln Gln Tyr Val Ser Leu
            500                 505                 510

Asp Leu Arg Pro Leu Glu Val Arg Arg Gly Leu Arg Ala Gln Ala Cys
        515                 520                 525

Ala Phe Trp Asn Arg Phe Leu Pro Lys Leu Leu Ser Ala Thr
530                 535                 540

<210> SEQ ID NO 2
<211> LENGTH: 544
<212> TYPE: PRT
<213> ORGANISM: Artificial sequence
<220> FEATURE:
<223> OTHER INFORMATION: Amino Acid sequence encoding RhAChE_m0p9

<400> SEQUENCE: 2

Met Glu Gly Arg Glu Asp Ala Glu Leu Leu Val Thr Thr Arg Gly Gly
1               5                   10                  15

Arg Leu Arg Gly Ile Arg Leu Met Thr Pro Gly Gly Pro Val Ser Ala
            20                  25                  30

Phe Leu Gly Ile Pro Phe Ala Glu Pro Pro Val Gly Pro Arg Arg Phe
        35                  40                  45

Arg Pro Pro Glu Pro Lys Gln Pro Trp Ser Gly Val Trp Asp Ala Thr
    50                  55                  60

Thr Phe Gln Asn Val Cys Tyr Gln Tyr Val Asp Thr Leu Tyr Pro Gly
65                  70                  75                  80

Phe Glu Gly Thr Glu Met Trp Asn Pro Asn Arg Asn Leu Ser Glu Asp
                85                  90                  95

Cys Leu Tyr Leu Asn Val Trp Thr Pro Tyr Pro Arg Pro Lys Asn Pro
            100                 105                 110
```

```
Ala Pro Val Met Val Trp Ile Tyr Gly Gly Phe Tyr Ser Gly Ser
            115                 120                 125

Ser Ser Leu Asp Val Tyr Asp Gly Arg Phe Leu Val Arg Thr Glu Arg
        130                 135                 140

Val Val Leu Val Ser Met Asn Tyr Arg Val Gly Ala Phe Gly Phe Leu
145                 150                 155                 160

Ala Leu Pro Gly Ser Arg Glu Ala Pro Gly Asn Val Gly Leu Leu Asp
                165                 170                 175

Gln Arg Leu Ala Leu Gln Trp Val Gln Glu Asn Ile Ala Ala Phe Gly
                180                 185                 190

Gly Asp Pro Thr Ser Val Thr Leu Phe Gly Glu Ser Ala Gly Ala Ala
                195                 200                 205

Ser Val Gly Met His Leu Leu Ser Pro Pro Ser Arg Gly Leu Phe His
            210                 215                 220

Arg Ala Ile Leu Gln Ser Gly Ala Pro Asn Ala Pro Trp Ala Thr Val
225                 230                 235                 240

Ser Met Glu Glu Ala Arg Arg Arg Ala Thr Gln Leu Ala Lys Leu Val
                245                 250                 255

Gly Cys Pro Pro Gly Gly Thr Gly Gly Asn Asp Thr Glu Leu Val Ala
                260                 265                 270

Cys Leu Arg Thr Arg Pro Pro Gln Glu Leu Val Asn His Glu Trp His
            275                 280                 285

Val Leu Pro Gln Glu Ser Val Phe Arg Phe Ser Phe Val Pro Val Val
            290                 295                 300

Asp Gly Asp Phe Leu Pro Asp Thr Pro Glu Ala Leu Ile Asn Asn Gly
305                 310                 315                 320

Asp Phe Lys Gly Leu Asp Val Leu Val Gly Val Asn Lys Asp Glu Gly
                325                 330                 335

Ser Tyr Phe Leu Val Tyr Gly Ala Pro Gly Phe Ser Lys Asp Asn Glu
                340                 345                 350

Ser Leu Ile Ser Arg Glu Glu Phe Leu Ala Gly Val Arg Val Gly Val
                355                 360                 365

Pro Gln Val Ser Asp Leu Ala Ala Glu Ala Val Val Leu His Tyr Thr
    370                 375                 380

Asp Trp Leu His Pro Glu Asp Pro Ala Arg Leu Arg Glu Ala Leu Ser
385                 390                 395                 400

Asp Val Val Gly Asp His Asn Val Ile Cys Pro Val Ala Gln Phe Ala
                405                 410                 415

Gln Arg Tyr Ala Ala Asn Gly Ala Arg Val Tyr Met Tyr Val Phe Glu
                420                 425                 430

His Arg Ser Ser Thr Leu Pro Trp Pro Glu Trp Met Gly Val Pro His
            435                 440                 445

Gly Tyr Glu Ile Glu Phe Ile Phe Gly Ile Pro Leu Asp Pro Ser Arg
            450                 455                 460

Asn Tyr Thr Glu Glu Glu Lys Ile Phe Ala Arg Arg Leu Met Arg Tyr
465                 470                 475                 480

Trp Ala Asn Phe Ala Arg Thr Gly Asp Pro Asn Glu Pro Arg Asp Pro
                485                 490                 495

Lys Ala Pro Gln Trp Pro Pro Tyr Thr Ala Asp Ala Gln Lys Tyr Val
                500                 505                 510
```

Ser Leu Asp Leu Arg Pro Leu Glu Val Arg Arg Gly Leu Arg Ala Gln
            515                 520                 525

Ala Cys Ala Phe Trp Asn Arg Phe Leu Pro Lys Leu Leu Ser Ala Thr
530                 535                 540

<210> SEQ ID NO 3
<211> LENGTH: 544
<212> TYPE: PRT
<213> ORGANISM: Artificial sequence
<220> FEATURE:
<223> OTHER INFORMATION: Amino Acid sequence encoding RhAChE_m0p45

<400> SEQUENCE: 3

Met Glu Gly Arg Glu Asp Ala Glu Leu Ile Val Thr Thr Arg Gly Gly
1               5                   10                  15

Lys Ile Arg Gly Ile Arg Leu Thr Thr Ile Gly Gly Pro Val Ser Ala
            20                  25                  30

Phe Leu Gly Ile Pro Phe Ala Glu Pro Pro Val Gly Pro Arg Arg Phe
        35                  40                  45

Arg Pro Pro Glu Pro Lys Arg Pro Trp Ser Gly Val Trp Asp Ala Thr
    50                  55                  60

Thr Phe Gln Asn Val Cys Tyr Gln Tyr Val Asp Thr Leu Tyr Pro Gly
65                  70                  75                  80

Phe Pro Gly Thr Glu Met Trp Asn Pro Asn Arg Pro Leu Ser Glu Asp
                85                  90                  95

Cys Leu Tyr Leu Asn Val Trp Thr Pro Tyr Pro Arg Pro Lys Asn Pro
            100                 105                 110

Ala Pro Val Met Val Trp Ile Tyr Gly Gly Gly Phe Tyr Ser Gly Ser
        115                 120                 125

Ser Ser Leu Asp Val Tyr Asp Gly Arg Phe Leu Val Arg Glu Glu Arg
130                 135                 140

Val Val Leu Val Ser Met Asn Tyr Arg Val Gly Ala Phe Gly Phe Leu
145                 150                 155                 160

Ala Leu Pro Gly Ser Arg Glu Ala Pro Gly Asn Val Gly Leu Leu Asp
                165                 170                 175

Gln Arg Leu Ala Leu Gln Trp Val Gln Glu Asn Ile Ala Ala Phe Gly
            180                 185                 190

Gly Asp Pro Thr Asn Val Thr Leu Phe Gly Glu Ser Ala Gly Ala Ala
        195                 200                 205

Ser Val Gly Met His Leu Leu Ser Pro Pro Ser Arg Gly Leu Phe His
    210                 215                 220

Arg Ala Ile Leu Gln Ser Gly Ala Pro Asn Ala Pro Trp Ala Tyr Val
225                 230                 235                 240

Ser Arg Glu Glu Ala Arg Arg Ala Leu Gln Leu Ala Lys Leu Val
                245                 250                 255

Gly Cys Pro Pro Gly Gly Thr Gly Gly Asn Asp Thr Glu Leu Val Ala
            260                 265                 270

Cys Leu Arg Asn Arg Pro Ala Gln Glu Leu Val Asn His Glu Trp His
        275                 280                 285

Val Leu Pro Gln Glu Ser Val Phe Arg Phe Ser Phe Val Pro Val Val
    290                 295                 300

Asp Gly Ser Phe Leu Pro Asp Thr Pro Glu Ala Leu Ile Asn Asn Gly
305                 310                 315                 320

Asp Phe Lys Gly Leu Gln Val Leu Val Gly Val Asn Lys Asp Glu Gly
                325                 330                 335

Ser Tyr Phe Leu Val Tyr Gly Ala Pro Gly Phe Ser Lys Asp Asn Glu
            340                 345                 350

Ser Leu Ile Ser Arg Glu Glu Phe Leu Glu Gly Val Arg Val Gly Val
            355                 360                 365

Pro Asn Val Ser Asp Leu Ala Ala Glu Ala Ile Val Leu His Tyr Thr
370                 375                 380

Asp Trp Leu His Pro Asp Asp Pro Glu Lys Asn Arg Asp Ala Leu Ala
385                 390                 395                 400

Asp Val Val Gly Asp His Asn Val Ile Cys Pro Val Ala Gln Phe Ala
                405                 410                 415

Glu Arg Tyr Ala Ala Asn Gly Ala Arg Val Tyr Ala Tyr Phe Phe Glu
            420                 425                 430

His Arg Ser Ser Thr Leu Pro Trp Pro Glu Trp Met Gly Val Pro His
            435                 440                 445

Gly Tyr Glu Ile Glu Phe Val Phe Gly Ile Pro Leu Asp Pro Ser Lys
            450                 455                 460

Asn Tyr Thr Lys Glu Glu Lys Ile Phe Ala Arg Arg Met Met Arg Tyr
465                 470                 475                 480

Trp Ala Asn Phe Ala Arg Thr Gly Asp Pro Asn Glu Pro Arg Asp Pro
                485                 490                 495

Lys Ala Pro Gln Trp Pro Pro Tyr Thr Ala Asp Glu Gln Lys Tyr Val
            500                 505                 510

Ser Leu Asp Leu Arg Pro Leu Glu Val Arg Arg Gly Leu Arg Ala Gln
            515                 520                 525

His Cys Ala Phe Trp Asn Arg Phe Leu Pro Lys Leu Leu Ser Met Thr
530                 535                 540

<210> SEQ ID NO 4
<211> LENGTH: 544
<212> TYPE: PRT
<213> ORGANISM: Artificial sequence
<220> FEATURE:
<223> OTHER INFORMATION: Amino Acid sequence encoding RhAChE_m0p7

<400> SEQUENCE: 4

Met Glu Gly Arg Glu Asp Ala Glu Leu Leu Val Thr Thr Arg Gly Gly
1               5                   10                  15

Arg Leu Arg Gly Ile Arg Leu Thr Thr Pro Gly Gly Pro Val Ser Ala
            20                  25                  30

Phe Leu Gly Ile Pro Phe Ala Glu Pro Pro Val Gly Pro Arg Arg Phe
        35                  40                  45

Arg Pro Pro Glu Pro Lys Gln Pro Trp Ser Gly Val Trp Asp Ala Thr
    50                  55                  60

Thr Phe Gln Asn Val Cys Tyr Gln Tyr Val Asp Thr Leu Tyr Pro Gly
65                  70                  75                  80

Phe Glu Gly Thr Glu Met Trp Asn Pro Asn Arg Asn Leu Ser Glu Asp
                85                  90                  95

Cys Leu Tyr Leu Asn Val Trp Thr Pro Tyr Pro Arg Pro Lys Asn Pro
            100                 105                 110

Ala Pro Val Met Val Trp Ile Tyr Gly Gly Gly Phe Tyr Ser Gly Ser
        115                 120                 125

Ser Ser Leu Asp Val Tyr Asp Gly Arg Phe Leu Val Arg Thr Glu Arg
    130                 135                 140

Val Val Leu Val Ser Met Asn Tyr Arg Val Gly Ala Phe Gly Phe Leu
145                 150                 155                 160

Ala Leu Pro Gly Ser Arg Glu Ala Pro Gly Asn Val Gly Leu Leu Asp
              165                 170                 175

Gln Arg Leu Ala Leu Gln Trp Val Gln Glu Asn Ile Ala Ala Phe Gly
        180                 185                 190

Gly Asp Pro Thr Ser Val Thr Leu Phe Gly Glu Ser Ala Gly Ala Ala
    195                 200                 205

Ser Val Gly Met His Leu Leu Ser Pro Pro Ser Arg Gly Leu Phe His
210                 215                 220

Arg Ala Ile Leu Gln Ser Gly Ala Pro Asn Ala Pro Trp Ala Tyr Val
225                 230                 235                 240

Ser Arg Glu Glu Ala Arg Arg Arg Ala Leu Gln Leu Ala Lys Leu Val
                245                 250                 255

Gly Cys Pro Pro Gly Thr Gly Gly Asn Asp Thr Glu Leu Val Ala
                260                 265                 270

Cys Leu Arg Asn Arg Pro Pro Gln Glu Leu Val Asn His Glu Trp His
            275                 280                 285

Val Leu Pro Gln Glu Ser Val Phe Arg Phe Ser Phe Val Pro Val Val
        290                 295                 300

Asp Gly Asp Phe Leu Pro Asp Thr Pro Glu Ala Leu Ile Asn Asn Gly
305                 310                 315                 320

Asp Phe Lys Gly Leu Asp Val Leu Val Gly Val Asn Lys Asp Glu Gly
                325                 330                 335

Ser Tyr Phe Leu Val Tyr Gly Ala Pro Gly Phe Ser Lys Asp Asn Glu
            340                 345                 350

Ser Leu Ile Ser Arg Glu Glu Phe Leu Glu Gly Val Arg Val Gly Val
        355                 360                 365

Pro Gln Val Ser Asp Leu Ala Ala Glu Ala Ile Val Leu His Tyr Thr
370                 375                 380

Asp Trp Leu His Pro Glu Asp Pro Ala Lys Asn Arg Asp Ala Leu Ser
385                 390                 395                 400

Asp Val Val Gly Asp His Asn Val Ile Cys Pro Val Ala Gln Phe Ala
                405                 410                 415

Gln Arg Tyr Ala Ala Asn Gly Ala Arg Val Tyr Ala Tyr Val Phe Glu
            420                 425                 430

His Arg Ser Ser Thr Leu Pro Trp Pro Glu Trp Met Gly Val Pro His
        435                 440                 445

Gly Tyr Glu Ile Glu Phe Ile Phe Gly Ile Pro Leu Asp Pro Ser Arg
    450                 455                 460

Asn Tyr Thr Lys Glu Glu Lys Ile Phe Ala Arg Arg Leu Met Arg Tyr
465                 470                 475                 480

Trp Ala Asn Phe Ala Arg Thr Gly Asp Pro Asn Glu Pro Arg Asp Pro
                485                 490                 495

Lys Ala Pro Gln Trp Pro Pro Tyr Thr Ala Asp Glu Gln Lys Tyr Val
            500                 505                 510

Ser Leu Asp Leu Arg Pro Leu Glu Val Arg Arg Gly Leu Arg Ala Gln
        515                 520                 525

Ala Cys Ala Phe Trp Asn Arg Phe Leu Pro Lys Leu Leu Ser Ala Thr
530                 535                 540

<210> SEQ ID NO 5
<211> LENGTH: 544
<212> TYPE: PRT
<213> ORGANISM: Artificial sequence
<220> FEATURE:
<223> OTHER INFORMATION: Amino Acid sequence encoding RhAChE_m1p2

<400> SEQUENCE: 5

```
Met Glu Gly Arg Glu Asp Ala Glu Leu Leu Val Thr Thr Arg Gly Gly
1               5                   10                  15
Arg Leu Arg Gly Ile Arg Leu Lys Thr Pro Gly Gly Pro Val Ser Ala
            20                  25                  30
Phe Leu Gly Ile Pro Phe Ala Glu Pro Pro Val Gly Pro Arg Arg Phe
        35                  40                  45
Arg Pro Pro Glu Pro Lys Gln Pro Trp Ser Gly Val Trp Asp Ala Thr
    50                  55                  60
Thr Phe Gln Asn Val Cys Tyr Gln Tyr Val Asp Thr Leu Tyr Pro Gly
65                  70                  75                  80
Phe Glu Gly Thr Glu Met Trp Asn Pro Asn Arg Glu Leu Ser Glu Asp
                85                  90                  95
Cys Leu Tyr Leu Asn Val Trp Thr Pro Tyr Pro Arg Pro Thr Ser Pro
            100                 105                 110
Val Pro Val Met Val Trp Ile Tyr Gly Gly Gly Phe Tyr Ser Gly Ser
        115                 120                 125
Ser Ser Leu Asp Val Tyr Asp Gly Arg Phe Leu Val Arg Ala Glu Arg
    130                 135                 140
Val Val Leu Val Ser Met Asn Tyr Arg Val Gly Ala Phe Gly Phe Leu
145                 150                 155                 160
Ala Leu Pro Gly Ser Arg Glu Ala Pro Gly Asn Val Gly Leu Leu Asp
                165                 170                 175
Gln Arg Leu Ala Leu Gln Trp Val Gln Glu Asn Ile Ala Ala Phe Gly
            180                 185                 190
Gly Asp Pro Thr Ser Val Thr Leu Phe Gly Glu Ser Ala Gly Ala Ala
        195                 200                 205
Ser Val Gly Met His Leu Leu Ser Pro Pro Ser Arg Gly Leu Phe His
    210                 215                 220
Arg Ala Ile Leu Gln Ser Gly Ala Pro Asn Ala Pro Trp Ala Thr Val
225                 230                 235                 240
Ser Met Glu Glu Ala Arg Arg Arg Ala Thr Gln Leu Ala Lys Leu Val
                245                 250                 255
Gly Cys Pro Pro Gly Gly Thr Gly Gly Asn Asp Thr Glu Leu Val Ala
            260                 265                 270
Cys Leu Arg Thr Arg Pro Pro Gln Val Leu Val Asn His Glu Trp His
        275                 280                 285
Val Leu Pro Gln Glu Ser Val Phe Arg Phe Ser Phe Val Pro Val Val
    290                 295                 300
Asp Gly Asp Phe Leu Pro Asp Thr Pro Glu Ala Leu Ile Asn Asn Gly
305                 310                 315                 320
Asp Phe Lys Gly Leu Gln Val Leu Val Gly Val Asn Lys Asp Glu Gly
                325                 330                 335
Ser Tyr Phe Leu Val Tyr Gly Ala Pro Gly Phe Ser Lys Asp Asn Glu
            340                 345                 350
Ser Leu Ile Ser Arg Glu Glu Phe Leu Ala Gly Val Arg Val Gly Val
        355                 360                 365
Pro Gln Val Ser Asp Leu Ala Ala Glu Ala Val Val Leu His Tyr Thr
    370                 375                 380
Asp Trp Leu His Pro Glu Asp Pro Ala Arg Leu Arg Glu Ala Leu Ser
385                 390                 395                 400
Asp Val Val Gly Asp His Asn Val Val Cys Pro Val Ala Gln Phe Ala
                405                 410                 415
```

```
Gln Arg Tyr Ala Ala Gln Gly Ala Arg Val Tyr Met Tyr Val Phe Glu
                420                 425                 430

His Arg Ala Ser Thr Leu Pro Trp Pro Glu Trp Met Gly Val Pro His
            435                 440                 445

Gly Tyr Glu Ile Glu Phe Ile Phe Gly Ile Pro Leu Asp Pro Ser Arg
        450                 455                 460

Asn Tyr Thr Ala Glu Glu Lys Ile Phe Ala Gln Arg Leu Met Arg Tyr
465                 470                 475                 480

Trp Ala Asn Phe Ala Arg Thr Gly Asp Pro Asn Glu Pro Arg Asp Pro
                485                 490                 495

Lys Ala Pro Gln Trp Pro Pro Tyr Thr Ala Asp Ala Gln Gln Tyr Val
            500                 505                 510

Ser Leu Asp Leu Arg Pro Leu Glu Val Arg Arg Gly Leu Arg Ala Gln
        515                 520                 525

His Cys Ala Phe Trp Asn Arg Phe Leu Pro Lys Leu Leu Ser Ala Thr
    530                 535                 540

<210> SEQ ID NO 6
<211> LENGTH: 544
<212> TYPE: PRT
<213> ORGANISM: Artificial sequence
<220> FEATURE:
<223> OTHER INFORMATION: Amino Acid sequence encoding RhAChE_m2p0

<400> SEQUENCE: 6

Met Glu Gly Arg Glu Asp Ala Glu Leu Leu Val Thr Val Arg Gly Gly
1               5                   10                  15

Arg Leu Arg Gly Ile Arg Leu Lys Thr Pro Gly Gly Pro Val Ser Ala
                20                  25                  30

Phe Leu Gly Ile Pro Phe Ala Glu Pro Pro Met Gly Pro Arg Arg Phe
            35                  40                  45

Arg Pro Pro Glu Pro Lys Gln Pro Trp Ser Gly Val Trp Asp Ala Thr
        50                  55                  60

Thr Phe Gln Asn Val Cys Tyr Gln Tyr Val Asp Thr Leu Tyr Pro Gly
65                  70                  75                  80

Phe Glu Gly Thr Glu Met Trp Asn Pro Asn Arg Glu Leu Ser Glu Asp
                85                  90                  95

Cys Leu Tyr Leu Asn Val Trp Thr Pro Tyr Pro Arg Pro Thr Ser Pro
            100                 105                 110

Thr Pro Val Met Val Trp Ile Tyr Gly Gly Gly Phe Tyr Ser Gly Ser
        115                 120                 125

Ser Ser Leu Asp Val Tyr Asp Gly Arg Phe Leu Val Gln Ala Glu Arg
130                 135                 140

Val Val Leu Val Ser Met Asn Tyr Arg Val Gly Ala Phe Gly Phe Leu
145                 150                 155                 160

Ala Leu Pro Gly Ser Arg Glu Ala Pro Gly Asn Val Gly Leu Leu Asp
                165                 170                 175

Gln Arg Leu Ala Leu Gln Trp Val Gln Glu Asn Ile Ala Ala Phe Gly
            180                 185                 190

Gly Asp Pro Thr Ser Val Thr Leu Phe Gly Glu Ser Ala Gly Ala Ala
        195                 200                 205

Ser Val Gly Met His Leu Leu Ser Pro Pro Ser Arg Gly Leu Phe His
    210                 215                 220

Arg Ala Ile Leu Gln Ser Gly Ala Pro Asn Ala Pro Trp Ala Thr Val
225                 230                 235                 240
```

Ser Met Gly Glu Ala Arg Arg Arg Ala Thr Gln Leu Ala Lys Leu Val
            245                 250                 255

Gly Cys Pro Pro Gly Gly Thr Gly Gly Asn Asp Thr Glu Leu Val Ala
        260                 265                 270

Cys Leu Arg Thr Arg Pro Ala Gln Val Leu Val Asn His Glu Trp His
            275                 280                 285

Val Leu Pro Gln Glu Ser Val Phe Arg Phe Ser Phe Val Pro Val Val
    290                 295                 300

Asp Gly Asp Phe Leu Ser Asp Thr Pro Glu Ala Leu Ile Asn Ala Gly
305                 310                 315                 320

Asp Phe His Gly Leu Gln Val Leu Val Gly Val Asn Lys Asp Glu Gly
            325                 330                 335

Ser Tyr Phe Leu Val Tyr Gly Ala Pro Gly Phe Ser Lys Asp Asn Glu
        340                 345                 350

Ser Leu Ile Ser Arg Ala Glu Phe Leu Ala Gly Val Arg Val Gly Val
            355                 360                 365

Pro Gln Val Ser Asp Leu Ala Ala Glu Ala Val Val Leu His Tyr Thr
    370                 375                 380

Asp Trp Leu His Pro Glu Asp Pro Ala Arg Leu Arg Glu Ala Leu Ser
385                 390                 395                 400

Asp Val Val Gly Asp His Asn Val Val Cys Pro Val Ala Gln Phe Ala
            405                 410                 415

Gln Arg Tyr Ala Ala Gln Gly Ala Arg Val Tyr Ala Tyr Val Phe Glu
        420                 425                 430

His Arg Ala Ser Thr Leu Pro Trp Pro Glu Trp Met Gly Val Pro His
            435                 440                 445

Gly Tyr Glu Ile Glu Phe Ile Phe Gly Ile Pro Leu Asp Pro Ser Arg
    450                 455                 460

Asn Tyr Thr Ala Glu Glu Lys Ile Phe Ala Gln Arg Leu Met Arg Tyr
465                 470                 475                 480

Trp Ala Asn Phe Ala Arg Thr Gly Asp Pro Asn Glu Pro Arg Asp Pro
            485                 490                 495

Lys Ala Pro Gln Trp Pro Pro Tyr Thr Ala Gly Ala Gln Gln Tyr Val
        500                 505                 510

Ser Leu Asp Leu Arg Pro Leu Glu Val Arg Arg Gly Leu Arg Ala Gln
            515                 520                 525

Ala Cys Ala Phe Trp Asn Arg Phe Leu Pro Lys Leu Leu Ser Ala Thr
    530                 535                 540

<210> SEQ ID NO 7
<211> LENGTH: 342
<212> TYPE: PRT
<213> ORGANISM: Artificial sequence
<220> FEATURE:
<223> OTHER INFORMATION: Amino Acid sequence encoding PTE-S5 variant of
      PTE

<400> SEQUENCE: 7

Gly Arg Ile Ser Glu Phe Ile Thr Asn Ser Gly Asp Arg Ile Asn Thr
1               5                   10                  15

Val Arg Gly Pro Ile Thr Ile Ser Glu Ala Gly Phe Thr Leu Thr His
            20                  25                  30

Glu His Ile Cys Gly Ser Ser Ala Gly Phe Leu Arg Ala Trp Pro Glu
        35                  40                  45

Phe Phe Gly Ser Arg Lys Ala Leu Ala Glu Lys Ala Val Arg Gly Leu
    50                  55                  60

Arg Arg Ala Arg Ala Ala Gly Val Arg Thr Ile Val Asp Val Ser Thr
65                  70                  75                  80

Phe Asp Ile Gly Arg Asp Val Ser Leu Leu Ala Glu Val Ser Arg Ala
                85                  90                  95

Ala Asp Val His Ile Val Ala Ala Thr Gly Leu Trp Phe Asp Pro Pro
            100                 105                 110

Leu Ser Met Arg Leu Arg Ser Val Glu Glu Leu Thr Gln Phe Phe Leu
        115                 120                 125

Arg Glu Ile Gln Tyr Gly Ile Glu Asp Thr Gly Ile Arg Ala Gly Ile
    130                 135                 140

Ile Lys Val Ala Thr Thr Gly Lys Ala Thr Pro Phe Gln Glu Leu Val
145                 150                 155                 160

Leu Arg Ala Ala Ala Arg Ala Ser Leu Ala Thr Gly Val Pro Val Thr
                165                 170                 175

Thr His Thr Ala Ala Ser Gln Arg Gly Gly Glu Gln Gln Ala Ala Ile
            180                 185                 190

Phe Glu Ser Glu Gly Leu Ser Pro Ser Arg Val Cys Ile Gly His Ser
        195                 200                 205

Asp Asp Thr Asp Asp Leu Ser Tyr Leu Thr Ala Leu Ala Ala Arg Gly
    210                 215                 220

Tyr Leu Ile Gly Leu Asp His Ile Pro His Ser Ala Ile Gly Leu Glu
225                 230                 235                 240

Asp Asn Ala Ser Ala Ser Ala Leu Leu Gly Ile Arg Ser Trp Gln Thr
                245                 250                 255

Arg Ala Leu Leu Ile Lys Ala Leu Ile Asp Gln Gly Tyr Met Lys Gln
            260                 265                 270

Ile Leu Val Ser Asn Asp Trp Leu Phe Gly Phe Ser Ser Tyr Val Thr
        275                 280                 285

Asn Ile Met Asp Val Met Asp Ser Val Asn Pro Asp Gly Met Ala Phe
    290                 295                 300

Ile Pro Leu Arg Val Ile Pro Phe Leu Arg Glu Lys Gly Val Pro Gln
305                 310                 315                 320

Glu Thr Leu Ala Gly Ile Thr Val Thr Asn Pro Ala Arg Phe Leu Ser
                325                 330                 335

Pro Thr Leu Arg Ala Ser
            340

<210> SEQ ID NO 8
<211> LENGTH: 342
<212> TYPE: PRT
<213> ORGANISM: Artificial sequence
<220> FEATURE:
<223> OTHER INFORMATION: Amino Acid sequence encoding dPTE_m0p45

<400> SEQUENCE: 8

Gly Arg Ile Ser Glu Phe Ile Thr Asn Ser Gly Asp Arg Ile Asn Thr
1               5                   10                  15

Val Arg Gly Pro Ile Thr Ile Ser Glu Leu Gly Phe Thr Leu Met His
            20                  25                  30

Glu His Ile Cys Gly Ser Ser Ala Gly Phe Leu Arg Ala Trp Pro Glu
        35                  40                  45

Phe Phe Gly Ser Arg Asp Ala Leu Ala Glu Lys Ala Val Arg Gly Leu
    50                  55                  60

Arg Arg Ala Arg Ala Ala Gly Val Asp Thr Ile Val Asp Val Ser Thr
65                  70                  75                  80

```
Phe Asp Ile Gly Arg Asp Val Glu Leu Leu Ala Glu Val Ala Glu Ala
                85                  90                  95

Ala Asp Val His Ile Val Ala Ala Thr Gly Leu Trp Phe Asp Pro Pro
            100                 105                 110

Leu Ser Met Arg Leu Arg Ser Val Glu Glu Leu Thr Gln Phe Phe Leu
            115                 120                 125

Arg Glu Ile Gln Tyr Gly Ile Glu Asp Thr Gly Ile Arg Ala Gly Ile
130                 135                 140

Ile Lys Val Ala Thr Thr Gly Lys Ala Thr Pro Phe Gln Glu Arg Val
145                 150                 155                 160

Leu Arg Ala Ala Arg Ala Ser Leu Glu Thr Gly Val Pro Val Thr
                165                 170                 175

Thr His Thr Asp Ala Ser Gln Arg Asp Gly Glu Gln Ala Asp Ile
                180                 185                 190

Phe Glu Ser Glu Gly Leu Asp Pro Ser Arg Val Cys Ile Gly His Ala
            195                 200                 205

Asp Asp Thr Asp Leu Asp Tyr Leu Thr Glu Leu Ala Ala Arg Gly
    210                 215                 220

Tyr Leu Ile Gly Leu Asp His Ile Pro His Ser Ala Ile Gly Leu Glu
225                 230                 235                 240

Asp Asn Ala Ser Ala Ala Leu Leu Gly Leu Arg Ser Trp Gln Thr
                245                 250                 255

Arg Ala Leu Leu Ile Lys Ala Leu Ile Asp Gln Gly Tyr Ala Asp Gln
                260                 265                 270

Ile Leu Val Ser Asn Asp Trp Leu Phe Gly Phe Ser Ser Tyr Val Thr
                275                 280                 285

Asn Ile Met Asp Val Met Asp Arg Val Asn Pro Asp Gly Met Ala His
            290                 295                 300

Ile Pro Glu Arg Val Ile Pro Phe Leu Arg Glu Lys Gly Val Pro Asp
305                 310                 315                 320

Glu Thr Leu Asp Thr Ile Met Val Glu Asn Pro Ala Arg Phe Leu Ser
                325                 330                 335

Pro Thr Leu Arg Ala Ser
            340

<210> SEQ ID NO 9
<211> LENGTH: 342
<212> TYPE: PRT
<213> ORGANISM: Artificial sequence
<220> FEATURE:
<223> OTHER INFORMATION: Amino Acid sequence encoding dPTE_m1p00

<400> SEQUENCE: 9

Gly Arg Ile Ser Glu Phe Ile Thr Asn Ser Gly Asp Arg Ile Asn Thr
1               5                   10                  15

Val Arg Gly Pro Ile Thr Ile Ser Glu Ala Gly Phe Thr Leu Met His
                20                  25                  30

Glu His Ile Cys Gly Ser Ser Ala Gly Phe Leu Arg Ala Trp Pro Glu
            35                  40                  45

Phe Phe Gly Ser Arg Asp Ala Leu Ala Glu Lys Ala Val Arg Gly Leu
    50                  55                  60

Arg Arg Ala Arg Ala Ala Gly Val Arg Thr Ile Val Asp Val Ser Thr
65                  70                  75                  80

Phe Asp Ile Gly Arg Asp Val Glu Leu Leu Ala Glu Val Ser Glu Ala
                85                  90                  95
```

Ala Asp Val His Ile Val Ala Ala Thr Gly Leu Trp Phe Asp Pro Pro
            100                 105                 110

Leu Ser Met Arg Leu Arg Ser Val Glu Glu Leu Thr Gln Phe Phe Leu
        115                 120                 125

Arg Glu Ile Gln Tyr Gly Ile Glu Asp Thr Gly Ile Arg Ala Gly Ile
    130                 135                 140

Ile Lys Val Ala Thr Thr Gly Lys Ala Thr Pro Phe Gln Glu Arg Val
145                 150                 155                 160

Leu Arg Ala Ala Arg Ala Ser Leu Ala Thr Gly Val Pro Val Thr
                165                 170                 175

Thr His Thr Asp Ala Ser Gln Arg Asp Gly Glu Gln Gln Ala Asp Ile
            180                 185                 190

Phe Glu Ser Glu Gly Leu Asp Pro Ser Arg Val Cys Ile Gly His Ser
        195                 200                 205

Asp Asp Thr Asp Leu Asp Tyr Leu Thr Ala Leu Ala Ala Arg Gly
    210                 215                 220

Tyr Leu Ile Gly Leu Asp His Ile Pro His Ser Ala Ile Gly Leu Glu
225                 230                 235                 240

Asp Asn Ala Ser Ala Ala Leu Leu Gly Leu Arg Ser Trp Gln Thr
                245                 250                 255

Arg Ala Leu Leu Ile Lys Ala Leu Ile Asp Gln Gly Tyr Ala Asp Gln
            260                 265                 270

Ile Leu Val Ser Asn Asp Trp Leu Phe Gly Phe Ser Ser Tyr Val Thr
        275                 280                 285

Asn Ile Met Asp Val Met Asp Arg Val Asn Pro Asp Gly Met Ala Phe
    290                 295                 300

Ile Pro Leu Arg Val Ile Pro Phe Leu Arg Glu Lys Gly Val Pro Asp
305                 310                 315                 320

Glu Thr Leu Glu Thr Ile Met Val Asp Asn Pro Ala Arg Phe Leu Ser
                325                 330                 335

Pro Thr Leu Arg Ala Ser
            340

<210> SEQ ID NO 10
<211> LENGTH: 342
<212> TYPE: PRT
<213> ORGANISM: Artificial sequence
<220> FEATURE:
<223> OTHER INFORMATION: Amino Acid sequence encoding dPTE_m2p00

<400> SEQUENCE: 10

Gly Arg Ile Ser Glu Phe Ile Thr Asn Ser Gly Asp Arg Ile Asn Thr
1               5                   10                  15

Val Arg Gly Pro Ile Thr Ile Ser Glu Ala Gly Phe Thr Leu Thr His
            20                  25                  30

Glu His Ile Cys Gly Ser Ser Ala Gly Phe Leu Arg Ala Trp Pro Glu
        35                  40                  45

Phe Phe Gly Ser Arg Asp Ala Leu Ala Glu Lys Ala Val Arg Gly Leu
    50                  55                  60

Arg Arg Ala Arg Ala Ala Gly Val Arg Thr Ile Val Asp Val Ser Thr
65                  70                  75                  80

Phe Asp Ile Gly Arg Asp Val Ser Leu Leu Ala Glu Val Ser Glu Ala
                85                  90                  95

Ala Asp Val His Ile Val Ala Ala Thr Gly Leu Trp Phe Asp Pro Pro
            100                 105                 110

Leu Ser Met Arg Leu Arg Ser Val Glu Glu Leu Thr Gln Phe Phe Leu
            115                 120                 125

Arg Glu Ile Gln Tyr Gly Ile Glu Asp Thr Gly Ile Arg Ala Gly Ile
        130                 135                 140

Ile Lys Val Ala Thr Thr Gly Lys Ala Thr Pro Phe Gln Glu Leu Val
145                 150                 155                 160

Leu Arg Ala Ala Arg Ala Ser Leu Ala Thr Gly Val Pro Val Thr
            165                 170                 175

Thr His Thr Asp Ala Ser Gln Arg Asp Gly Gln Gln Ala Ala Ile
            180                 185                 190

Phe Glu Ser Glu Gly Leu Asp Pro Ser Arg Val Cys Ile Gly His Ser
        195                 200                 205

Asp Asp Thr Asp Asp Leu Asp Tyr Leu Thr Ala Leu Ala Ala Arg Gly
        210                 215                 220

Tyr Leu Ile Gly Leu Asp His Ile Pro His Ser Ala Ile Gly Leu Glu
225                 230                 235                 240

Asp Asn Ala Ser Ala Ser Ala Leu Leu Gly Ile Arg Ser Trp Gln Thr
            245                 250                 255

Arg Ala Leu Leu Ile Lys Ala Leu Ile Asp Gln Gly Tyr Val Lys Gln
            260                 265                 270

Ile Leu Val Ser Asn Asp Trp Leu Phe Gly Phe Ser Ser Tyr Val Thr
            275                 280                 285

Asn Ile Met Asp Val Met Asp Arg Val Asn Pro Asp Gly Met Ala Phe
            290                 295                 300

Ile Pro Leu Arg Val Ile Pro Phe Leu Arg Glu Lys Gly Val Pro Gln
305                 310                 315                 320

Glu Thr Leu Ala Thr Ile Thr Val Glu Asn Pro Ala Arg Phe Leu Ser
            325                 330                 335

Pro Thr Leu Arg Ala Ser
            340

<210> SEQ ID NO 11
<211> LENGTH: 287
<212> TYPE: PRT
<213> ORGANISM: Artificial sequence
<220> FEATURE:
<223> OTHER INFORMATION: Amino Acid sequence encoding Dnmt3a_Stab

<400> SEQUENCE: 11

Met Pro Ala Glu Lys Arg Lys Pro Ile Arg Val Leu Ser Leu Phe Asp
1               5                   10                  15

Gly Ile Ala Thr Gly Leu Leu Val Leu Lys Asp Leu Gly Ile Gln Val
            20                  25                  30

Asp Arg Tyr Ile Ala Ser Glu Val Cys Glu Asp Ser Ile Thr Val Gly
        35                  40                  45

Met Val Arg His Gln Gly Asn Ile Met Tyr Val Gly Asp Val Arg Asn
            50                  55                  60

Ile Thr Gln Lys His Ile Asp Glu Trp Gly Pro Phe Asp Leu Val Ile
65                  70                  75                  80

Gly Gly Ser Pro Cys Asn Asp Leu Ser Ile Val Asn Pro Ala Arg Lys
            85                  90                  95

Gly Leu Tyr Glu Gly Thr Gly Arg Leu Phe Phe Glu Phe Tyr Arg Leu
            100                 105                 110

Leu His Asp Ala Arg Pro Lys Glu Gly Asp Asp Arg Pro Phe Phe Trp
        115                 120                 125

```
Leu Phe Glu Asn Val Val Ala Met Arg Val Asn Asp Lys Arg Asp Ile
    130                 135                 140

Ser Arg Phe Leu Glu Cys Asn Pro Val Met Ile Asp Ala Lys Glu Val
145                 150                 155                 160

Ser Ala Ala His Arg Ala Arg Tyr Phe Trp Gly Asn Leu Pro Gly Met
                165                 170                 175

Asn Arg Pro Leu Cys Pro Ser Lys Asn Asp Lys Leu Glu Leu Gln Glu
            180                 185                 190

Cys Leu Glu His Gly Arg Gln Ala Lys Phe Ser Lys Val Arg Thr Ile
            195                 200                 205

Thr Thr Arg Ser Asn Ser Ile Lys Gln Gly Lys Asp Gln His Phe Pro
    210                 215                 220

Val Phe Met Asn Gly Lys Glu Asp Ile Leu Trp Cys Thr Glu Met Glu
225                 230                 235                 240

Arg Val Phe Gly Phe Pro Asp His Tyr Thr Asp Val Ser Asn Met Ser
                245                 250                 255

Arg Leu Ala Arg Gln Arg Leu Leu Gly Arg Ser Trp Ser Val Pro Val
            260                 265                 270

Ile Arg His Leu Phe Ala Pro Leu Lys Asp Tyr Phe Ala Cys Val
            275                 280                 285

<210> SEQ ID NO 12
<211> LENGTH: 48
<212> TYPE: PRT
<213> ORGANISM: Artificial Sequence
<220> FEATURE:
<223> OTHER INFORMATION: exemplary amino acid sequence

<400> SEQUENCE: 12

Ala Phe Tyr His Pro Val Tyr Pro Thr Leu Ser Arg Thr Lys Val Thr
1               5                   10                  15

Gly Met Ala Asp Phe Gly Pro Ala Ser Phe Trp Lys Ile Tyr Val Asn
            20                  25                  30

Arg Lys Thr Cys Phe Asp Gly Trp Asn Met Leu Arg Lys Val Ala Cys
            35                  40                  45
```